United States Patent [19]
McEver et al.

[11] Patent Number: 6,124,267
[45] Date of Patent: Sep. 26, 2000

[54] O-GLYCAN INHIBITORS OF SELECTIN MEDIATED INFLAMMATION DERIVED FROM PSGL-1

[75] Inventors: Rodger P. McEver, Oklahoma City; Richard D. Cummings, Edmond; Kevin L. Moore, Oklahoma City, all of Okla.

[73] Assignee: Southpac Trust Internationals, Inc.

[21] Appl. No.: 09/063,237

[22] Filed: Apr. 20, 1998

Related U.S. Application Data

[63] Continuation of application No. 08/649,802, May 17, 1996, abandoned, which is a continuation-in-part of application No. 08/510,920, Aug. 3, 1995, which is a continuation-in-part of application No. 08/278,551, Jul. 21, 1994, Pat. No. 5,464,778, which is a continuation of application No. 07/976,552, Nov. 16, 1992, abandoned, which is a continuation-in-part of application No. 07/650,484, Feb. 5, 1991, abandoned.

[51] Int. Cl.[7] ................................................. A61K 31/70
[52] U.S. Cl. ........................ 514/25; 514/54; 514/62; 536/17.2; 536/18.7
[58] Field of Search ................... 536/17.2, 18.7; 514/25, 54, 62

[56] References Cited

U.S. PATENT DOCUMENTS

| | | | |
|---|---|---|---|
| 3,625,214 | 12/1971 | Higichi | 128/260 |
| 3,995,444 | 12/1976 | Clark et al. | 62/306 |
| 4,494,385 | 1/1985 | Kuraoka et al. | 62/306 |
| 4,783,330 | 11/1988 | Furie et al. | 424/1.1 |
| 4,849,513 | 7/1989 | Smith et al. | 536/27 |
| 4,906,474 | 3/1990 | Langer et al. | 424/428 |
| 4,925,673 | 5/1990 | Steiner et al. | 424/455 |
| 5,114,842 | 5/1992 | Plow et al. | 424/85.8 |
| 5,135,916 | 8/1992 | Sims et al. | 514/21 |
| 5,211,936 | 5/1993 | Brandley et al. | 424/1.1 |
| 5,240,833 | 8/1993 | Nudelman et al. | 435/70.21 |
| 5,464,778 | 11/1995 | Cummings et al. | 436/503 |

FOREIGN PATENT DOCUMENTS

| | | |
|---|---|---|
| 9106632 | 5/1991 | WIPO. |
| 9107993 | 6/1991 | WIPO. |
| 91/19502 | 12/1991 | WIPO. |
| 9119501 | 12/1991 | WIPO. |
| 9201718 | 2/1992 | WIPO. |
| 9305803 | 4/1993 | WIPO. |
| 9410309 | 5/1994 | WIPO. |
| 9411498 | 5/1994 | WIPO. |
| 9530001 | 11/1995 | WIPO. |

OTHER PUBLICATIONS

Bowen, B.R., et al., "Characterization of a Human Homologue of the Murine Peripheral Lymph Node Homing Receptor", *J. Cell Bio.* 109, 421–427 (Jul. 1989).

Buerke, et al. "Sialyl Lewis[x]–containing Oligosaccharide Attenuates Myocardial Reperfusion Injury in Cats" *J. Clin. Invest.* 93, 1140–1148 (1994).

Carlsson et al., "Structural Variations of O–Linked Oligosaccharides Present in Leukosialin Isolated from Erythroid, Myeloid, and T–Lymphoid Cells Line" *J. Biol. Chem.,* 261(27), 12787–95, (1986).

Carlsson et al., "Isolation and Characterization of Leukosialin, a Major Sialoglycoprotein on Human Leukocytes", *J. Biol. Chem.,* 261(22), 12779–86 (1986).

Fukuda et al., "Structures of Sialyiated Fucosyl Polylactosaminoglycans Isolated from Chronic Myelogenous Leukemia Cells", *J. Biol. Chem.,* 260(24), 12957–12967 (1985).

Fukushi et al., "Novel Fucolipids Accumulating in Human Adenocarcinoma", *J. Biol. Chem.* 259(16): 10511–10517 (1984).

Gahmberg.et al. "Major O–Glycosylated Sialoglycoprotons of Human Hematopoietic Cells: Differentiation Antigens with Poorly Understood Functions" *J. Cell Biology* 37(1), 91–105 (May 1988).

(List continued on next page.)

*Primary Examiner*—Gary L. Kunz
*Attorney, Agent, or Firm*—Dunlap, Coddings & Rogers, P.C.

[57] ABSTRACT

Tyrosine sulfate on PSGL-1, particularly at least one of residues 46, 48 and 51, functions in conjunction with sialylated and fucosylated glycans, most preferably Thr-57, to mediate high affinity binding to P-selectin. PSGL-1 O-glycans have been determined to consist of disialylated or neutral forms of the core-2 tetrasaccharide Galβ1→4GlcNAcβ1→6(Galβ1→3)GalNAcOH. A minority of the O-glycans are α1,3 fucosylated that occur as two major species containing the sialyl Lewis x antigen—one species is a disialylated monofucosylated glycan:

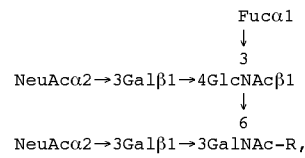

and the other is a monosialylated, trifucosylated glycan having a polylactosamine backbone:

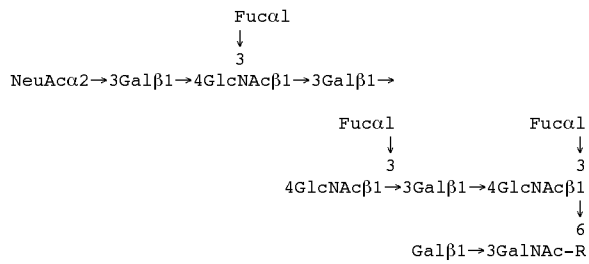

wherein R=H, OH, another sugar or an aglycone such as an amino acid, peptide, or polypeptide. The O-glycans defined herewith can be used to inhibit inflammation mediated by P-selectin.

3 Claims, 7 Drawing Sheets

OTHER PUBLICATIONS

Goelz, S.E., et al., "ELFT: A Gene That Directs the Expression of an ELAM–1 Ligand", *Cell* 63, 1349–1356 (Dec. 21, 1990).

Granert, et al., "Inhibition of Leukocyte Rolling with Polysaccharide Fucoidin Prevents Pleocytosis in Experimental Meningitis in the Rabbit", *J. Clin Invest.* 93, 929–936 (1994).

Korrel et al., "Identification of a tetrasialylated monofucosylated tetraantennary N–linked carbohydrate chain in human platelet glycocalicin" *FEBS Lett.*, 228(2), 321–326 (Feb. 1988).

Larsen, et al., in "PADGEM Protein: A Receptor that Mediates the Interaction of Activated Platelets with Neutrophils and Monocytes" *Cell* 59, 305–312 (Oct. 1989).

Lasky, et al., "Cloning of a Lymphocyte Homing Receptor Reveals a Lectin Domain", *Cell* 56, 1045–1055 (1989).

Lefer, et al., "A Novel Sialyl Lewis$^x$ Analog Attenuates Neurtrophic Accumulation and Myocardial Necrosis after Ischemia and Reperfusion" *Basic Science Reports* (1994).

Ley, et al., "Sulfated polysaccharides inhibit leukocyte rolling in rabbit mesentery venules" *J. Amer. Physiol. Soc.* (1991).

Ley, et al., "Fucoidin, But Not Yeast Polyphosphomannan PPME, Inhibits Leukocyte Rolling in Venules of the Rat Mesentery" *Blood* 81(1), 177–185 (1993).

Lowe, J.B., et al., "ELAM–1–Dependent Cell Adhesion to Vascular Endothelium Determined by a Transfected Human Fucosyltransferase cDNA", *Cell* 63, 475–484 (Nov. 2, 1990).

McEver, et al., The Platelet 2–Granule Membrane Protein GMP–140 is Also Synthesized by Human Vascular Endothelial Cells, *Blood* 70(5) Suppl. 1:355a, Abstract No. 1274 (1987).

McEver, R., et al., "GMP–140, a Platelet –/Granule Membrane Protein, is also Synthesized by Vascular Endothelial Cells and is Localized in Weibel–Palade Bodies", *J. Clin. Invest.* 84, 92–99 (Jul. 1989).

Mulligan, et al., "Protective Effects of Sialylated Oligosaccharides in Immune Complex–induced Acute Lung Injury" *J. Exp. Mec.* 178, 623–631 (1993).

Ord, et al., "Structure of the Gene Encoding the Human Leukocyte Adhesion Molecule–1 (TQ1, Leu–8) of Lymphocytes and Neutrophils", *J. Biol. Chem.* 265(14): 7760–7767 (1990).

Patel, K.D., et al., "Oxyten Radicals Induce Human Endothelial Cells to Express GMP–140 and Bind Neutrophils", *J. Cell. Biol.* 112(4), 749–759 (Feb. 1991).

Rosen, "The LEC–CAMs: An Emerging Family of Cell–Cell Adhesion Receptors Based upon Carbohydrate Recognition", *Am. J. Respir. Cell Mol. Biol.* 3:397–402 (1990).

Ruoslahti et al., "New Perspectives in Cell Adhesion: RGD and Integrins", *Science* 238:491–497 (1987).

Siegelman, M.H., et al., "Mouse Lymph Node Homing Receptor cDNA Clone Encodes a Glycoprotein Revealing Tandem Interaction Domains", *Science* 243, 1165–1172 (Mar. 3, 1989).

Siegelman, M.H., et al., "Human homologue of mouse lymph node homing receptor: Evolutionary conservation at tandem cell interaction domains", *Proc. Natl. Acad. Sci. USA* 86, 5562–5566 (1989).

Skinner, M.P., et al., "Characterization of Human Platelet GMP–140 as a Heparin–Binding Protein" *Biochem. Biophys. Res. Comm.* 164, 1373–1379 (1989).

Skurk, et al., "Sialyl Lewis$^x$–containing oligosaccharide exerts beneficial effects in murine traumatic shock" *J. Am. Physiol. Soc.* (1994).

Spooncer et al., "Isolation and Characterization of Polyfucosylated Lactosaminoglycan from Human Granulocytes", *J. Biol. Chem.* 259(8), 4792–4801 (1984).

Springer, "Adhesion receptors of the immune system", *Nature* 346, 425–434 (Aug. 2, 1990).

Springer, T.A., et al., "Sticky sugars for selectins", *Nature* 349, 196–197 (Jan. 17, 1991).

Stanley et al., "The LEC11 Chinese Hamster Ovary Mutant Synthesizes N–Linked Carbohydrates Containing Sialylated, Fucosylated Lactosamine Units", *J. Biol. Chem.*, 263(23), 11374–11381 (Aug. 15, 1988).

Stenberg, P., et al., "A Platelet Alpha–Granule Membrane Protein (GMP–140) is Expressed on the Plasma Membrane after Activation", *J. Cell. Biol.* 101, 880–886 (1985).

Tangelder and Arfors, "Inhibition of Leukocyte Rolling in Venules by Protamine and Sulfated Polysaccharides" *Blood* 77(7), 1555–1571 (1991).

Tedder, T., et al., "Isolation and Chromosomal Localization of cDNAs Enclding a Novel Human Lymphocyte Cell Surface Molecule, LAM–1", *J. Exp. Med.* 170, 123–133 (1989).

Watson, M.L., et al., "Genomic Organization of the Selectin Family of Leukocyte Adhesion Molecules on Human and Mouse Chromosome 1", *J. Exp. Med.* 172, 263–271 (Jul. 1990).

Aruffo et al., "CD62/P–Selectin Recognition and Myeloid and Tumor Cell Sulfatides", *Cell*, 67:35–44 (Oct. 1991).

Aulabaugh et al., "Conformational Analysis of Bombesin Analogues", *Peptides*, 526–528 (1990).

Battistutta et al. "Circular Dichroism and $^1$H NMR Studies on Bombolitin–related Peptides in Aqueous Solution Containing SDS Micelles", *Peptides* 525–526 (1992).

Beckstead et al., "Immunohistochemical Localization of Membrane and α–Granule Proteins in Human Megacaryocytes: Application to Plastic–Embedded Bone Marrow Biopsy Specimens", *Blood*, 67:285–293 (Feb. 1986).

Bevilacqua et al., "Identification of an Inducible Endothelial Leukocyte Adhesion Molecule", *Proc. Natl. Acad. Sci. USA*, 84:9238–9242 (Dec. 1987).

Bevilacqua et al., "Endothelial Leukocyte Adhesion Molecule 1: An Inducible Receptor for Neutrophils Related to Complement Regulatory Proteins and Lectins", *Science*, 243:1160–1165 (Mar. 3, 1989).

Bienvenu et al., "Molecular Determinants of Shear Rate–Dependent Leukocyte Adhesion in Postcapillary Venule", *The American Physiology Society*, H1504–H1508 (1993).

Bierhuizen et al., "Expression of a Differentiation Antigen and Poly–N–acetyll actosaminly O–glycans Directed by a Cloned Core 2 β–1,6–N–Acetylglucosaminyltransferase", *The Journal of Biological Chemistry* 269(6):4473–4479 (Feb. 1994).

Bonfanti et al., "PADGEM (GMP140) Is a Component of Weibel–Palade Bodies of Human Endothellial Cells", *Blood* 73:1109–1112 (Apr. 1989).

Borman S., "Glycotechnology Drugs Begin to Emerge from the Lab", *C&EN* 27–34 (Jun. 28, 1993).

Brandley et al., "Carbohydrate Ligands of the LEC Cell Adhesion Molecules", *Cell*, 63:861–863 Nov. 1990.

Brockmeyer et al., "Distribution of Cell Adhesion Molecules (ICAM–1, VCAM–1, ELAM–1 in Renal Tissue During Allograft Rejection", *Transplantation* 55:610–615 (Mar. 1993).

Burgen et al., "Binding of Flexible Ligands to Macromolecules", *Nature*, 253:753–755 (Feb. 1975).

Buttrum et al., "Selectin–Mediated Rolling of Neutrophils on Immobilized Platelets", *Blood*, 83:1165–1174 (Aug. 1993).

Colman et al., "Three–Dimensional Structure of a Complex of Antibody with Influenza Virus Neuraminidase", *Nature*, 326:358–363 (Mar. 1987).

Corral et al., "Requirement for Sialic Acid on Neutrophils in a GMP–140 (PADGEM) Mediated Adhesive Interaction with Activated Platelets", *Biochemical and Biophysical Research Communications*, 172:1349–1356 (Nov. 1990).

Cummings R., Untitled paper prepared at the University of Oklahoma Health Sciences Center, Mar. 23, 1995.

Damle et al., "GMP–140 (P–selectin/CD62) Binds to Chronically Stimulated but not Resting CD4$^+$T Lymphocytes and Regulates Their Production of Proinflammatory Cytokines", *Eur. J. Immunol.*, 22:1789–1793 (1992).

Dawson et al., "The Monoclonal Antibody MEL–14 Can Block Lymphocyte Migration Into a Site of Chronic Inflammation", *Eur. J. Immunol.*, 1647–1650 (1992).

Doré et al., "P–Selectin Mediates Spontaneous Leukocyte Rolling In Vivo", *Blood*, 82:1308–1316 (Aug. 1993).

Dorfman et al., "Human Transcription Factor GATA–2", *J. Biol. Chem.*, 267:1279–1285 (Jan. 1992).

Dunlop et al., "Characterization of GMP–140 (P–selectin) as a Circulating Plasman Protein", *J. Exp. Med.*, 175:1147–1150 (Apr. 1992).

Edwards et al, "The Role of Leukocytes in the Activation of Blood Coagulation", *Seminars in Hematology*, 29:202–212 (Jul. 1992).

Engleberts et al., "Generalized Inflammation During Peritonitis Evidenced by Intracutaneous E–Selectin Expression", *Clinical Immunology and Immunopathology*, 65:330–334 (Dec. 1992).

Engleberts et al., "A Role for ELAM–1 in the Pathogenesis of MOF during Septic Shock", *Journal of Surgical Research*, 53:136–144 (1992).

Franklin T., "Binding Energy and the Activation of Hormone Receptors", *Pharmacology*, 29:853–856 (1980).

Fuggle et al., "Variation in Expression of Endothelial Adhesion Molecules in Pretransplant and Transplanted Kidneys–Correlation with Intragraft Events", *Transplantation*, 55:117–123 (Jan. 1993).

Gamble et al., "Prevention of Activated Neutrophil Adhesion to Endothelium by Soluble Adhesion Protein GMP140", *Science*, 249:414–417 (Jul. 1990).

Geng et al., "Lectin Domain Peptides from Selectins Interact with Both Cell Surface Ligands and Ca$^{2+}$ Ions", *J. Biol. Chem.*, 267:19846–19853 (Oct. 1992).

Geng et al., "Rapid Neutrophil Adhesion to Activated Endothelium Mediated by GMP–140", *Nature* 343:757–760 (Feb. 1990).

Gibbons et al., "New Mechanisms and Intermediates in the Folding and Unfolding of Peptides and Proteins: Bioactive solution Conformation of Linear Peptides", *Peptides*, 508–509 (1990).

Grober et al., "Monocyte–Endothelial Adhesion in Chronic Rheumatoid Arthritis", *J. Clin. Invest.*, 91:2609–2619 (Jun. 1993).

Hakomori S., "Aberrant Glycosylation in Cancer Cell Membranes as Focused on Glycolipids: Overview and Perspectives", *Cancer Research*, 45:2405–2414 (Jun. 1985).

Hamburger et al., "GMP–140 Mediates Adhesion of Stimulated Platelets to Neutrophils", *Blood*, 75:550–554 (Feb. 1990).

Handa et al., "Selectin GMP–140 (CD62; PADGEM) Binds to Sialosyl–Le$^x$, and Sulfated Glycans Modulate this Binding", *Biochemical and Biophysical Research Communications*, 181:1223–1230 (Dec. 1991).

Hard et al., "The Carbohydrate Chains of the β Subunit of Human Chorionic Gonadotropin Produced by the Choriocarcinoma Cell Line BeWo", *Eur. J. Biochem*, 205:785–798 (1992).

Hattori et al., "Complement Proteins C5b–9 Induce Secretion of High Molecular Weight Multimers of Endothelial von Willebrand Factor and Translocation of Granule Membrane Protein GMP–140 to the Cell Surface", *J. Biol. Chem.*, 264:9053–9060 (May 1989).

Hattori et al., "Stimulated Secretion of Endothelial von Willebrand Factor is Accompanied by Rapid Redistribution to the Cell Surface of the Intracellular Granule Membrane Protein GMP–140", *J. Biol. Chem.* 264:7768–7771 (May 1989).

Hemmerich et al., "Structure of the O–Glycans in Bly-CMA–1, and Endothelial–derived Ligand for L–selectin", *The Journal of Biological Chemistry* 270(20):12035–12047 (May 1995).

Hoff et al., "Increased Expression of Sialyl–Dimeric Le$^x$ Antigen in Liver Metastases of Human Colorectal Carcinoma", *Cancer Research*, 49:6883–6888 (Dec. 1989).

Hollengaugh et al., "Interaction of P–Selectin (CD62) and Its Cellular Ligand: Analysis of Critical Residues" *Biochemistry*, 32:2960–2966 (1993).

Huang et al., "A Lymphocyte Homing Receptor (L–Selectin) Mediates the In Vitro Attachment of Lymphocytes to Myelinated Tracts of the Central Nervous System", *J. Clin. Invest.*, 88:1778–1783 (Nov. 1991).

Jewell et al., "Cytokine Induction of Leucocyte Adhesion Molecules–1 (LAM–1) Expression on Chronic Lymphocytic Leukaemia Cells", *Leukemia* 6(5):400–404 May 1992).

Johnston et al., "Cloning of GMP–140: Chromosomal Localization, Molecular Heterogeneity and Identification of cDNAs Predicting Both Membrane Bound and Soluble Proteins", *Blood Suppl.*, 72:327a (Nov. 1988).

Johnston et al., "Cloning of GMP–140, a Granule Membrane Protein of Platelets and Endothelium: Sequence Similarity to Proteins Involved in Cell Adhesion and Inflammation", *Cell*, 56:1033–1044 (Mar. 1989).

Johnston et al., "Structural and Biosynthetic Studies of the Granule Membrane Protein, GMP–140, from Human Platelets and Endothelial Cells", *The Journal of Biological Chemistry*, 264:1–8 (Jan. 1989).

Johnston et al., Structure and Biosynthesis of the Platelet α–Granule Membrane Protein, GMP–140, *Blood Suppl.* p. 352a, abstract # 1264 Nov. 1987.

Johnston et al., "Structure of the Human Gene Encoding Granule Membrane Protein–140, a member of the Selectin Family of Adhesion Receptors for Leukocytes", The Journal of Biological Chemistry 265(34):21381–21385 (Dec. 1990).

Jungi et al., "Platelet–Leukocyte Interaction: Selective Binding of Thrombin–Stimulated Platelets to Human Monocytes, Polymorphonuclear Leukocytes, and Related Cell Lines", *Blood* 67(3):629–636 (Mar. 1986).

Kojima et al., "Inhibition of Selectin–Dependent Tumor Cell Adhesion to Endothelial Cells and Platelets by Blocking O–Glycosylation of These Cells", *Biochemical and Biophysical Research Communication*, 182(3):1288–1295 (Feb. 1992).

Laiken et al., "A New Model for the Binding of Flexible Ligands to Proteins", *Biochemistry*, 10:2101–2106 (1971).

Larsen et al., "PADGEM–Dependent Adhesion of Platelets to Monocytes and Neutrophils Is Mediated by a Lineage–Specific Carbohydrate, LNF III (CD15)", *Cell*, 63:467–474 (Nov. 1990).

Lawrence et al., "Leukocytes Roll on a Selectin at Physiologic Flow Rates: Distinction from and Prerequisite for Adhesion through Integrins", *Cell*, 65:1–20 (May 1991).

Levinovitz et al., "Identification of a Glycoprotein Ligand for E–Selectin on Mouse Myeloid Cells", *The Journal of Cell Biology*, 121(2):449–459 (Apr. 1993).

Ley et al., "Lectin–Like Cell Adhesion Molecule 1 Mediates Leukocyte Rolling in Mesenteric Venules In Vivo", *Blood*, 77(12):2553–2555 (Jun. 1991).

Li et al., "T Cells Expressing Both L–Selectin and CD44 Molecules Increase in Number in Peritoneal Exudate Cells and In Vitro–Stimulated Spleen Cells from Mice Immunized Intraperitoneally with Listeria Monocytogenes", *Immunology*, 78:28–34 (1993).

Liao et al, "Oxidized Lipoproteins, Elicit Leukocyte–Endothelial Cell Adhesion in Mesenteric Venules", *The FASEB Journal*, 7(3):1986 (1993).

Lo–Guidice et al., "Sialylation and Sulfation of the Carbohydrate Chains in Respiratory Mucins from a Patient with Cystic Fibrosis", *The Journal of Biological Chemistry*, 269(29):18794–18813 (Jul. 1994).

Lowe et al., "A Transfected Human Fucosyltransferase cDNA Determines Biosynthesis of Oligosaccharide Ligand(s) for Endothelial–Leukocyte Adhesion Molecule 1", *Biochemical Society Transaction*, 19:649–653 (1991).

Maemura et al, "Poly–N–Acetyllactosaminly O–Glycans Attached to Leukosialin", *The Journal of Biological Chemistry*, 267(34):24379–24386 (Dec. 1992).

Majuri et al., "Recombinant E–selectin–protein Mediates Tumor Cell Adhesion via Sialyl–Lea and Sialyl–Lex", *Biochemical and Biophysical Research Communications*, 182(3):1376–1382 (Feb. 1992).

Mayadas et al., "Leukocyte Rolling and Extravasation Are Severely Compromised in P Selectin–Deficient Mice", *Cell*, 74:541–554 (Aug. 1993).

McEver R., "Leukocyte–Endothelial Cell Interactions", *Current Opinion in Cell Biology*, 4:840–849 (1992).

McEver et al., "A Monoclonal Antibody to a Membrane Glycoprotein Binds Only to Activated Platelets", *The Journal of Biological Chemistry*, 259(15):9799–9804 (Aug. 1984).

McEver R., "Properties of GMP–140, an Inducible Granule Membrane Protein of Platets and Endothelium", *Blood Cells*, 16:73–83 (1990).

McEver R., "Selectins: Novel Receptors that Mediate Leukocyte Adhesion During Inflammation", *Thrombosis and Haemostasis*, 65(3):223–228 (1991).

Moore et al., "GMP–140 Binds to a Glycoprotein Receptor on Human Neutrophils: Evidence for a Lectin–Like Interaction", *The Journal of Cell Biology*, 112(3):491–499 (Feb. 1991).

Moore et al., "Identification of a Specific Glycoprotein Ligand for P–Selectin (CD62) on Myeloid Cells", *The Journal of Cell Biology*, 118(2):445–456 (Jul. 1992).

Moore et al., "P–Selectin (CD62 Binds to Subpopulations of Human Memory T Lymphocytes and Natural Keller Cells", *Biochemical and Biophysical Research Communications*, 186(1):173–181 (Jul. 1992).

Mulligan et al., "Protective Effects of Oligosaccharides in P–Selectin–Dependent Lung Injury", *Nature* 364:149–151 (Jul. 1993).

Munroe et al., "Expression of Sialyl–Lewis X, an E–Selectin Ligand, IN Inflammation, Immune Processes, and Lymphoid Tissues", *American Journal of Pathology*, 141(6):12397–1408 (Dec. 1992).

Nelson et al., "Higher–Affinity Oligosaccharide Ligands for E–Selectin", *J. Clin. Invest.*, 91:1157–1166 (Mar. 1993).

Norgard et al., "Characterization of a Specific Ligand for P–Selectin on Myeloid Cells: A Minor Glycoprotein With Sialylated O–linked Oligosaccharides", *The Journal of Biological Chemistry*, 268(18):12764–12774 (Jun. 1993).

Phillips et al, "ELAM–1 Mediates Cell Adhesion by Recognition of a Carbohydrate Ligand, Sialyl–Le$^x$", *Science* 250:1130–1132 (Nov. 1990).

Polley et al., "CD62 and Endothelial Cell–Leukocyte Adhesion Molecule 1 (ELAM–1) Recognize the Same Carbohydrate Ligand, Sialyl–Lewis x", *Proc. Natl. Acad. Sci. USA*, 88:6224–6228 (Jul. 1991).

Simmons et al., "Sialyl Ligands Facilitate Lymphocyte Accumulation During Inflammation of the Central Nervous System", *Journal of Neuroimmunology*, 41:123–130 (1992).

Skinner et al, "GMP–140 Binding to Neutrophils Is Inhibited by Sulfated Glycans", *The Journal of Biological Chemistry*, 266(9):5371–5374 (Mar. 1991).

Takada et al., Adhesion of Human Cancer Cells to Vascular Endothelium Mediated, *Biochemical and Biophysical Research Communications*, 179(2):713–719 (Sep. 1991).

Tiemeyer et al., "Carbohydrate Ligands for Endothelial–Leukocyte Adhesion Molecule 1", *Proc. Natl. Acad. Sci. USA*, 88:1138–1142 (Feb. 1991).

Walz et al., "Recognition by ELAM–1 of the Sialyl–Le$^x$ Determinant on Myeloid and Tumor Cells", *Science*, 250:1132–1135 (Nov. 1990).

Winn et al., "Anti–P–Selectin Monoclonal Antibody attenuates Reperfusion Injury to the Rabbit Ear", *J. Clin. Invest.*, 92:2042–2047 (Oct. 1993).

Winn et al., "Monoclonal Antibodies to P–Selectin Are Effective in Preventing Reperfusion Injury to Rabbit Ears", *Supplement I Circulation*, 86(4):0316 (Oct. 1992).

Zhou et al., "The Selectin GMP–140 Binds to Sialylated, Fucosylated Lactosaminoglycans on Both Myeloid and Nonmyeloid Cells", *The Journal of Cell Biology*, 115(2):557–564 (Oct. 1991).

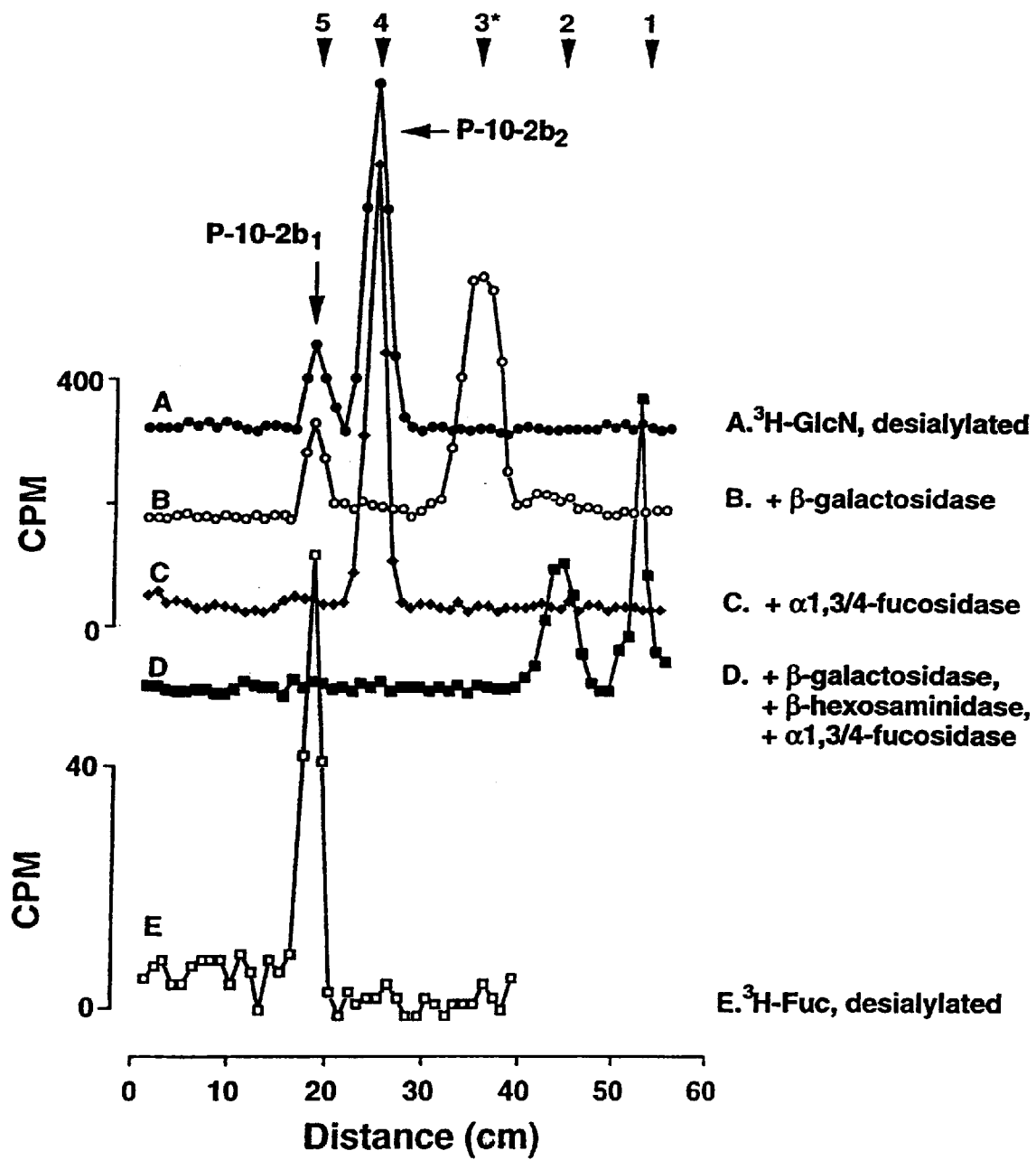
FIGURES 4A-E

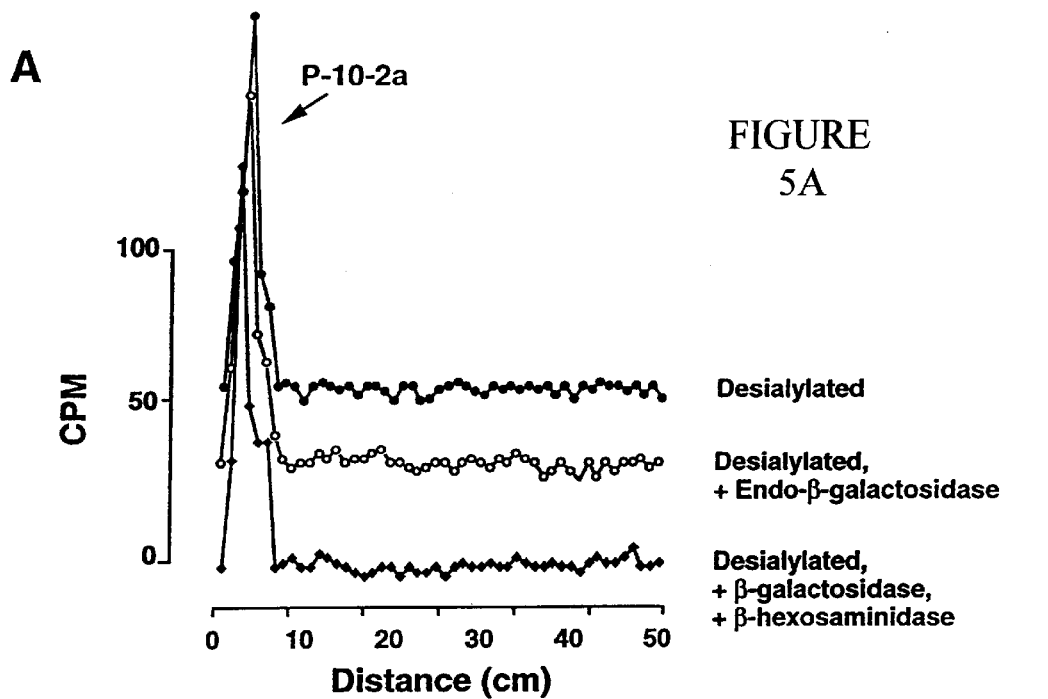
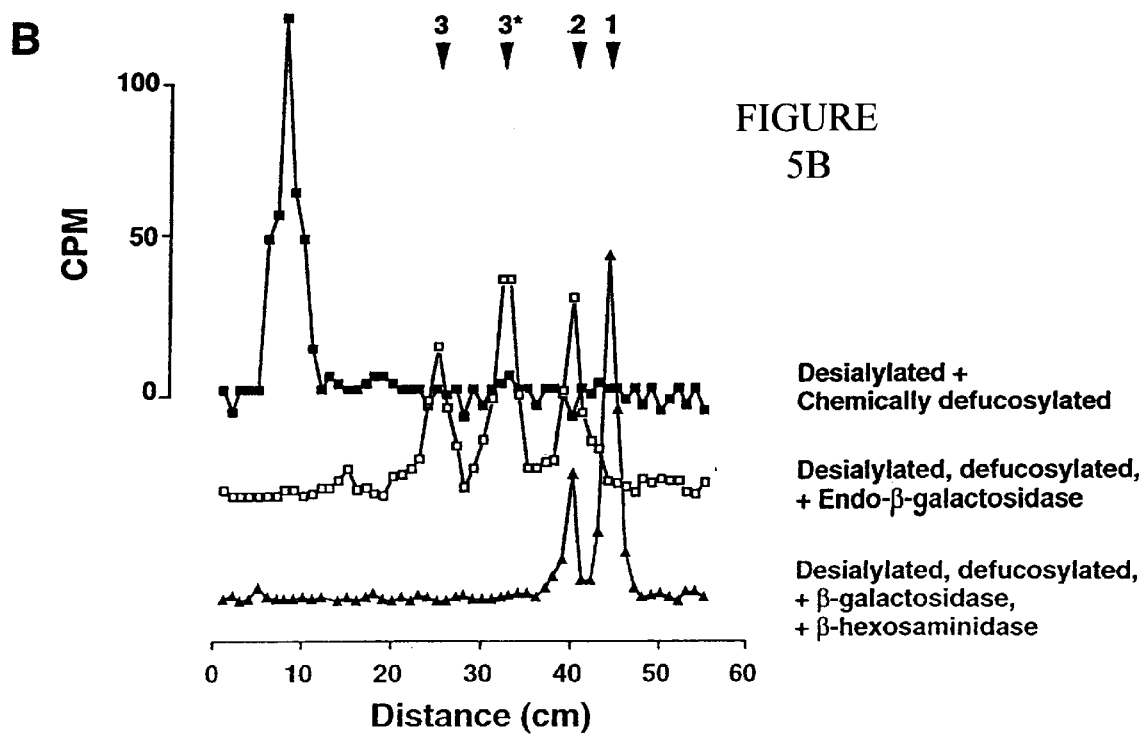

| O-Glycan Structures | Fraction | % |
|---|---|---|
| Gal $\xrightarrow{\beta 1,3}$ GalNAcOH | P-10-3 | 14 |
| Gal $\xrightarrow{\beta 1,4}$ GlcNAc $\downarrow \beta 1,6$<br>Gal $\xrightarrow{\beta 1,3}$ GalNAcOH | P-10-3 | 52 |
| NeuAc $\xrightarrow{\alpha 2,3}$ { Gal $\xrightarrow{\beta 1,4}$ GlcNAc $\downarrow \beta 1,6$ , Gal $\xrightarrow{\beta 1,3}$ GalNAcOH } | P-10-3 | 6 |
| NeuAc $\xrightarrow{\alpha 2,3}$ Gal $\xrightarrow{\beta 1,4}$ GlcNAc $\downarrow \beta 1,6$<br>NeuAc $\xrightarrow{\alpha 2,3}$ Gal $\xrightarrow{\beta 1,3}$ GalNAcOH | P-10-2b$_2$ | 14 |
| Fuc $\downarrow \alpha 1,3$<br>NeuAc $\xrightarrow{\alpha 2,3}$ Gal $\xrightarrow{\beta 1,4}$ GlcNAc $\downarrow \beta 1,6$<br>NeuAc $\xrightarrow{\alpha 2,3}$ Gal $\xrightarrow{\beta 1,3}$ GalNAcOH | P-10-2b$_1$ | 2 |
| NeuAc $\xrightarrow{\alpha 2,3}$ Gal $\xrightarrow{\beta 1,4}$ GlcNAc $\xrightarrow{\beta 1,3}$ Gal $\xrightarrow{\beta 1,4}$ GlcNAc $\xrightarrow{\beta 1,3}$ Gal $\xrightarrow{\beta 1,4}$ GlcNAc (with Fuc $\alpha 1,3$ on each GlcNAc) $\downarrow \beta 1,6$<br>Gal $\xrightarrow{\beta 1,3}$ GalNAcOH | P-10-2a | 12 |

FIGURE 7

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

```
Met Pro Leu Gln Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
            115                 120                 125

Thr Glu Ala Gln Thr Thr Pro Leu Ala Ala Thr Glu Ala Gln Thr Thr
    130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
            180                 185                 190

Thr Thr Ala Pro Ala Ala Met Glu Ala Gln Thr Thr Pro Pro Ala Ala
            195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Thr Gln Pro Thr Ala Thr Glu
225                 230                 235                 240

Ala Gln Thr Thr Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
            260                 265                 270

Phe Ile Pro Phe Ser Val Ser Val Thr His Lys Gly Ile Pro Met
    275                 280                 285

Ala Ala Ser Asn Leu Ser Val Asn Tyr Pro Val Gly Ala Pro Asp His
    290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
                325                 330                 335

Arg Lys Gly His Met Tyr Pro Val Arg Asn Tyr Ser Pro Thr Glu Met
            340                 345                 350

Val Cys Ile Ser Ser Leu Leu Pro Asp Gly Gly Glu Gly Pro Ser Ala
            355                 360                 365

Thr Ala Asn Gly Gly Leu Ser Lys Ala Lys Ser Pro Gly Leu Thr Pro
    370                 375                 380

Glu Pro Arg Glu Asp Arg Glu Gly Asp Asp Leu Thr Leu His Ser Phe
385                 390                 395                 400

Leu Pro
```

(2) INFORMATION FOR SEQ ID NO:2:

(i) SEQUENCE CHARACTERISTICS:
        (A) LENGTH: 2042 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
AGGAAACCTG CCATGGCCTC CTGGTGAGCT GTCCTCATCC ACTGCTCGCT GCCTCTCCAG      60
ATACTCTGAC CCATGGATCC CCTGGGTGCA GCCAAGCCAC AATGGCCATG GCGCCGCTGT     120
CTGGCCGCAC TGCTATTTCA GCTGCTGGTG CTGTGTGTT TCTTCTCCTA CCTGCGTGTG      180
TCCCGAGACG ATGCCACTGG ATCCCCTAGG GCTCCCAGTG GGTCCTCCCG ACAGGACACC     240
ACTCCCACCC GCCCCACCCT CCTGATCCTG CTATGGACAT GGCCTTTCCA CATCCCTGTG     300
GCTCTGTCCC GCTGTTCAGA GATGGTGCCC GGCACAGCCG ACTGCCACAT CACTGCCGAC     360
CGCAAGGTGT ACCCACAGGC AGACACGGTC ATCGTGCACC ACTGGGATAT CATGTCCAAC     420
CCTAAGTCAC GCCTCCCACC TTCCCCGAGG CCGCAGGGGC AGCGCTGGAT CTGGTTCAAC     480
TTGGAGCCAC CCCCTAACTG CCAGCACCTG GAAGCCCTGG ACAGATACTT CAATCTCACC     540
ATGTCCTACC GCAGCGACTC CGACATCTTC ACGCCCTACG GCTGGCTGGA GCCGTGGTCC     600
GGCCAGCCTG CCCACCCACC GCTCAACCTC TCGGCCAAGA CCGAGCTGGT GGCCTGGGCG     660
GTGTCCAACT GGAAGCCGGA CTCAGCCAGG GTGCGCTACT ACCAGAGCCT GCAGGCTCAT     720
CTCAAGGTGG ACGTGTACGG ACGCTCCCAC AAGCCCCTGC CCAAGGGGAC CATGATGGAG     780
ACGCTGTCCC GGTACAAGTT CTACCTGGCC TTCGAGAACT CCTTGCACCC CGACTACATC     840
ACCGAGAAGC TGTGGAGGAA CGCCCTGGAG GCCTGGGCCG TGCCCGTGGT GCTGGGCCCC     900
AGCAGAAGCA ACTACGAGAG GTTCCTGCCA CCCGACGCCT TCATCCACGT GGACGACTTC     960
CAGAGCCCCA AGGACCTGGC CCGGTACCTG CAGGAGCTGG ACAAGGACCA CGCCCGCTAC    1020
CTGAGCTACT TTCGCTGGCG GGAGACGCTG CGGCCTCGCT CCTTCAGCTG GGACTGGATT    1080
TCTGCAAGGC CTGCTGGAAA CTGCAGCAGG AATCCAGGTA CCAGACGGTG CGCAGCATAG    1140
CGGCTTGGTT CACCTGAGAG GCCGGCATGG TGCCTGGGCT GCCGGGAACC TCATCTGCCT    1200
GGGGCCTCAC CTGCTGGAGT CCTTTGTGGC CAACCCTCTC TCTTACCTGG ACCTCACAC     1260
GCTGGGCTTC ACGGCTGCCA GGAGCCTCTC CCCTCCAGAA GACTTGCCTG CTAGGGACCT    1320
CGCCTGCTGG GGACCTCGCC TGTTGGGGAC CTCACCTGCT GGGACCTCA CCTGCTGGGG     1380
ACCTTGGCTG CTGGAGGCTG CACCTACTGA GGATGTCGGC GGTCGGGGAC TTTACCTGCT    1440
GGGACCTGCT CCCAGAGACC TTGCCACACT GAATCTCACC TGCTGGGGAC CTCACCCTGG    1500
AGGGCCCTGG GCCCTGGGGA ACTGGCTTAC TTGGGGCCCC ACCCGGGAGT GATGGTTCTG    1560
GCTGATTTGT TTGTGATGTT GTTAGCCGCC TGTGAGGGGT GCAGAGAGAT CATCACGGCA    1620
CGGTTTCCAG ATGTAATACT GCAAGGAAAA ATGATGACGT GTCTCCTCAC TCTAGAGGGG    1680
TTGGTCCCAT GGGTTAAGAG CTCACCCCAG GTTCTCACCT CAGGGGTTAA GAGCTCAGAG    1740
TTCAGACAGG TCCAAGTTCA AGCCCAGGAC CACCACTTAT AGGGTACAGG TGGGATCGAC    1800
TGTAAATGAG GACTTCTGGA ACATTCCAAA TATTCTGGGG TTGAGGGAAA TTGCTGCTGT    1860
CTACAAAATG CCAAGGGTGG ACAGGCGCTG TGGCTCACGC CTGTAATTCC AGCACTTTGG    1920
GAGGCTGAGG TAGGAGGATT GATTGAGGCC AAGAGTTAAA GACCAGCCTG GTCAATATAG    1980
```

```
CAAGACCACG TCTCTAAATA AAAAATAATA GGCCGGCCAG GAAAAAAAAA AAAAAAAAAA    2040

AA                                                                  2042
```

(2) INFORMATION FOR SEQ ID NO:3:

(i) SEQUENCE CHARACTERISTICS:
        (A) LENGTH: 2102 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
GTGAAGTGCT CAGAATGGGG CAGGATGTCA CCTGGAATCA GCACTAAGTG ATTCAGACTT      60

TCCTTACTTT TAAATGTGCG CTCTTCATTT CAAGATGCCG TTGCAGCTCT GATAAATGCA     120

AACTGACAAC CTTCAAGGCC ACGACGGAGG GAAAATCATT GGTGCTTGGA GCATAGAAGA     180

CTGCCCTTCA CAAAGGAAAT CCCTGATTAT TGTTTGAAAT GCTGAGGACG TTGCTGCGAA     240

GGAGACTTTT TTCTTATCCC ACCAAATACT ACTTTATGGT TCTTGTTTTA TCCCTAATCA     300

CCTTCTCCGT TTTAAGGATT CATCAAAAGC CTGAATTTGT AAGTGTCAGA CACTTGGAGC     360

TTGCTGGGGA GAATCCTAGT AGTGATATTA ATTGCACCAA AGTTTTACAG GGTGATGTAA     420

ATGAAATCCA AAAGGTAAAG CTTGAGATCC TAACAGTGAA ATTTAAAAAG CGCCCTCGGT     480

GGACACCTGA CGACTATATA AACATGACCA GTGACTGTTC TTCTTTCATC AAGAGACGCA     540

AATATATTGT AGAACCCCTT AGTAAAGAAG AGGCGGAGTT TCCAATAGCA TATTCTATAG     600

TGGTTCATCA CAAGATTGAA ATGCTTGACA GGCTGCTGAG GGCCATCTAT ATGCCTCAGA     660

ATTTCTATTG CGTTCATGTG GACACAAAAT CCGAGGATTC CTATTTAGCT GCAGTGATGG     720

GCATCGCTTC CTGTTTTAGT AATGTCTTTG TGGCCAGCCG ATTGGAGAGT GTGGTTTATG     780

CATCGTGGAG CCGGGTTCAG GCTGACCTCA ACTGCATGAA GGATCTCTAT GCAATGAGTG     840

CAAACTGGAA GTACTTGATA AATCTTTGTG GTATGGATTT TCCCATTAAA ACCAACCTAG     900

AAATTGTCAG CAAGCTCAAG TTGTTAATGG GAGAAAACAA CCTGGAAACG GAGAGGATGC     960

CATCCCATAA AGAACAAAGG TGGAAGAAGC CCTATGAGGT CGTTAATCGA AAGCTGACAA    1020

ACACAGGGAC TGTCAAAATG CTTCCTCCAC TCGAAACACC TCTCTTTTCT GGCAGTGCCT    1080

ACTTCGTGCT CAGTAGGGAC TATGTGGGGT ATGTACTACA GAATGAAAAA ATCCAAAAGT    1140

TGATGGAGTG GGCACAAGAC ACATACAGCC CTGATGAGTA TCTCTGCGCC ACCATCCAAA    1200

GGATTCCTGA AGTCCCGGCC TCACTCCCTG CCAGCCATAA GTATGATCTA TGTGACATGC    1260

AAGCAGTTGC CAGGTTTGTC AAGTGGCACT ACTTCAGGG TGATGTTTCC AAGGGTGCTC     1320

CCTACCCGCC CTGCGATGGA GTCCATGTGC GCTCAGTGTG CATTTTCGGA GCTGGTGACT    1380

TGAACTGGAT GCTGCGCAAA CACCACTTGT TTGCCAATAA CTTTGACGTG CATGTTGACC    1440

TCTTTGCCAT CCAGTGTTTG CATGAGCATT TGAGACACAA AGCTTTGCAG ACATTAAAAC    1500

ACTGACCATT ACGGGCAATT TTATGAACAA GAAGAAGGAT ACACAAAACG TACCTTATCT    1560

GTTTCCCCTT CCTTGTCAGC GTCGGGAAGA TGGTATGAAG TCCTCTTTGG GGCAGGGACT    1620

CTAGTAGATC TTCTTGTAGA GAAGCTGCAT GGTTTCTGCA GAGCACAGTT AGCTAGAAAG    1680

GTGATAGCAT TAAATGTTCA TCTAGAGTTA ATAGTGGGAG GAGTAAAGGT AGCCTTGAGG    1740

CCAGAGCAGG TAGCAAGGCA TTGTGCAAAG AGGGGACCAG GGTGGCTGGG CAAGAGGCCG    1800

ATGCATAAAG TCAGCCTGTT CCAAGTGCTC AGGGACTTAG CAAAATGAGA AGATGTGACC    1860
```

-continued

```
TGTGCCAAAA CTATTTTGAC AATTTTAAAT GTGACCATTT TTCTGGTATG AATAAACTTA    1920

CAGCAACAAA TAATCAAAGA TACAATTAAT CTGATATTAT ATTTGTTGAA ATAGAAATTT    1980

GATTGTACTA TAAATGATTT TTGTAAATAA TTTATATTCT GCTCTAATAC TGTACTGTGT    2040

AGTCTGTCTC CGTATGTCAT CTCAGGGAGC TTAAAATGGG CTTGATTTAA CATTGAAAAA    2100

AA                                                                  2102
```

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
GTCCCTCTAG ACCACCATGA TTGCTTCACA GTTT                                34
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
TCCCGGTCGA CTTAGGGAGC TTCACAGGT                                      29
```

O-GLYCAN INHIBITORS OF SELECTIN MEDIATED INFLAMMATION DERIVED FROM PSGL-1

This is a continuation of copending application Ser. No. 08/649,802 filed on May 17, 1996, ABN, which is a CIP of Ser. No. 08/510,920 filed on Aug. 3, 1995, which is a CIP of Ser. No. 08/278,551 filed on Jul. 21, 1994, now U.S. Pat. No. 5,464,778, which is a CON of Ser. No. 07/976,552 filed on Nov. 16, 1992, ABN, which is a CIP of 07/650,484 filed on Feb. 5, 1991, ABN.

BACKGROUND OF THE INVENTION

The present invention is directed to inhibitors of selectin mediated inflammation and is particularly directed to inhibitors derived from PSGL-1, the ligand for P-selectin, and novel oligosaccharides derived from PSGL-1.

The United States government has rights in this invention by virtue of National Institutes of Health Grant PO1 HL54804 and RO1 HL 43510 to Richard D. Cummings and Rodger P. McEver.

The selectins are a family of three $Ca^{2+}$-dependent membrane-bound lectins that initiate adhesion of leukocytes to platelets or endothelial cells under the shear forces found in the venular circulation (Laskey, (1992) Science 258, 964–969; Bevilacqua, et al., (1993) J. Clin. Invest. 91, 379–387; McEver (1994) Curr. Opin. Immunol. 6, 75–84). L-selectin, expressed on leukocytes, binds to constitutive or inducible ligands on endothelial cells. E-selectin, expressed by cytokine-activated endothelial cells, and P-selectin, expressed by thrombin-activated platelets and endothelial cells, bind to ligands on myeloid cells and subsets of lymphocytes.

P-selectin is a calcium-dependent carbohydrate-binding protein that is expressed on the surfaces of activated platelets and endothelium in response to thrombin and other agonists (McEver, et al. (1995) J. Biol. Chem., 270, 11025–11028; Varki, A. (1994) Proc. Natl. Acad. Sci., U.S.A. 91, 7390–7397; Springer, T. A. (1995) Annu. Rev. Physiol. 57, 827–872). Through its binding to glycoconjugate-based counterreceptors on leukocytes, P-selectin mediates rolling adhesion of these cells on activated platelets and endothelium (Lawrence and Springer (1991) Cell 65, 852–873; Moore, et al. (1995) J. Cell. Biol. 128, 661–671). Both sialic acid and fucose are components of the P-selectin counterreceptors on leukocytes (Corral, et al. (1990) Biochem. Biophys. Res. Comm. 172, 1349–1356; Moore, et al. (1992) J. Cell. Biol. 118, 445–456; Sako, et al. (1993) Cell 75, 1179–1186).

Although the selectins interact weakly with small sialylated, fucosylated oligosaccharides such as sialyl Lewis x (sLe$^x$; NeuAcα2-3Galβ1-4[Fucα1-3]GlcNAc) (Foxall, et al., (1992) J. Cell Biol. 117, 895–902; Varki, (1992) Curr. Opin. Cell Biol. 257, 257–266), they bind with higher affinity to glycans displayed on a limited number of glycoproteins (Moore, et al., (1992) J. Cell Biol. 118, 445–456; Lasky, et al., (1992) Cell 69, 927–938; Levinovitz, et al. (1993) J. Cell Biol. 121, 449–459; Walcheck, et al., (1993) J. Exp. Med. 178, 853–863; Baumhueter, et al., (1993) Science 262, 436–438; Berg, et al., (1993) Nature 366, 695–698) or proteoglycans (Norgard-Sumnicht, et al., (1993) Science 261, 480–483). Oligosaccharides containing sialyl Lewis x (sLe$^x$), NeuAcα2-3Galβ1-4[Fucα1-3] GlcNAcβ1-R, a determinant present on leukocyte surfaces, inhibit adhesion of leukocytes to P-selectin (Polley, et al., (1991) Proc. Natl. Acad. Sci. USA 88, 6224–6228; Foxall, et al. (1992) J. Cell Biol. 117, 895–902). However, expression of slex on cell surfaces is not sufficient for high affinity binding of cells to P-selectin, since non-myeloid cells that express high levels of sLe$^x$ bind poorly to P-selectin compared to myeloid cells (Zhou, et al. (1991) J. Cell Biol. 115, 557–564). The high affinity ligands are potentially important as physiologic mediators of selectin-mediated leukocyte adhesion during inflammation. Thus, understanding the structural basis for high affinity recognition of these glycoconjugates by the selectins has attracted increasing interest.

A subset of the high affinity selectin ligands consists of mucin-like glycoproteins (McEver, et al. (1995)). One sialomucin ligand for P-selectin is expressed by human neutrophils and the human promyelocytic HL-60 cell line (Moore, et al., (1992); (Moore, et al., (1994) J. Biol. Chem. 269, 23318–23327). Leukocytes express a single high affinity ligand for P-selectin, termed P-selectin glycoprotein ligand-1 (PSGL-1) (Moore, et al., (1995); Moore, et al., (1992); Sako, et al., (1993); Norgaard, et al. (1993) J. Biol. Chem. 268, 12764–127748; Moore, et al. (1994) J. Biol. Chem. 269, 23318–23327). Binding of P-selectin to the ligand is $Ca^{2+}$ dependent and is abolished by treatment of the ligand with sialidase.

PSGL is a homodimer with two disulfide-linked subunits with relative molecular masses of approximately 120,000 as assessed by SDS-PAGE (Moore, et al., 1992). Each subunit has no more than three N-glycans, but has many clustered, sialylated O-glycans (Moore, et al. (1992); Norgard, et al. (1993) J. Biol. Chem. 268, 12764–12774). The extracellular domain of PSGL-1 is highly extended, a characteristic feature of mucin-like proteins. PSGL-1 is a type 1 membrane protein with an extracellular domain containing many serines, threonines, and prolines, including a series of decameric repeats (15 in human promyelocytic HL-60 cells and 16 in human leukocytes) (Sako, et al. (1993) Cell 75, 1179–1186; Moore, et al. (1995) J. Cell Biol. 128, 661–671; Veldman, et al. (1995) J. Biol. Chem. 270, 16470–16475). Following an 18-residue signal peptide, there is a propeptide spanning residues 19–41 that is removed from PSGL-1 following its synthesis in leukocytes (Sako, et al. (1993); Vachino, et al. (1995) J. Biol. Chem. 270, 21966–21974). The extracellular domain of the processed mature protein extends from residues 42 to 318, and is followed by a 25-residue transmembrane domain at a 69-residue cytoplasmic tail. It carries many unmodified sialic residues as well as the sLe$^x$ antigen. The ligand contains at least one PNGaseF-sensitive N-linked glycan that P-selectin does not require for recognition. In contrast, it has clustered, sialylated, O-linked oligosaccharides that render the polypeptide backbone sensitive to cleavage by the enzyme O-sialoglycoprotease. Treatment of intact HL-60 cells with this enzyme eliminates the high affinity binding sites of P-selectin (Ushiyama, et al., (1993) J. Biol. Chem. 268, 15229–15237) and prevents cell adhesion to immobilized P-selection (Norgard, et al., (1993) J. Biol. Chem. 268, 12764–12774; Steininger, et al., Biochem. Biophys. Res. Commun. (1992) 188, 760–766), without affecting the overall surface expression of sLe$^x$. These data suggest that this sialomucin, which carries only a small portion of the cell surface sLe$^x$, corresponds to functionally important, high affinity binding sites for P-selectin on human myeloid cells.

Sako et al. (1993) isolated a cDNA derived from human HL-60 cells that encodes PSGL-1. The cDNA-derived sequence for each subunit of PSGL1 predicts a type 1 transmembrane protein of 402 amino acids. The extracellular domain has an N-terminal signal peptide from residues 1 to 18 and a putative propeptide from residues 19–41. Assuming cleavage of the ipropeptide, the extracellular domain of the mature protein begins at residue 42 and extends to residue 308. The sequence concludes with a 25-residue transmembrane domain and a 69 residue cytoplasmic tail. The extracellular domain is rich in serines and threonines that are potential sites of O-glycosylation. The extracellular domain contains three potential sites for addition of N-linked oligosaccharides as well as a single cysteine that might promote dimerization and three potential tyrosine sulfation sites at residues 46, 48 and 51.

Although previous studies have shown that sialylation and fucosylation of PSGL-1 are required for its binding to P-selectin, other post-translational modifications of PSGL-1 may also be important. PSGL-1 is highly O-glycosylated and contains sialylated and fucosylated O-linked poly-N-acetyllactosamine, including some glycans that terminate in sLe$^x$ (Moore, et al. (1994) *J. Biol. Chem.* 269, 23318–23327). sLe$^x$ or related glycans are not sufficient for high affinity binding of PSGL-1 to P-selectin. For example, sulfated compounds lacking either sialic acid or fucose can inhibit adhesion of leukocytes to P-selectin (Norgaard-Sumnicht, et al. (1993) *Science* 261, 480–483; Nelson, et al. (1993) *Blood* 82, 3253–3258; Cecconi, et al. (1994) *J. Biol. Chem.* 269, 15060–15066; Skinner, et al. (1989) *Biochem. Biophys. Res. Comm.* 164, 1373–1379). These data suggest that sulfation of PSGL-1 may be required for its high affinity binding to P-selectin. Recombinant PSGL-1 expressed in COS cells with a fucosyltransferase interacts with P-selectin in cell adhesion experiments (Sako, et al., 1993). However, the degree to which the oligosaccharides on recombinant PSGL-1 resemble those on the native glycoprotein ligand is unknown.

Although carbohydrates on PSGL-1 are critical for binding to selectins, no detailed chemical structures of the glycans are available. Much of the information about the glycosylation of the molecule has been obtained by enzymatic treatments of the native ligand and by studies on recombinant forms of PSGL-1 expressed in various cell types. While these indirect methods can provide valuable information about critical determinants on the ligand, detailed structural information on O-glycans from native PSGL-1 is essential to identify glycans that are important for ligand function and to provide a clearer understanding of why PSGL-1 is a ligand for P-and E-selectin, whereas other mucins such as CD43 are not.

It is therefore an object of the present invention to provide a method for making PSGL-1 which is normally glycosylated and sulfated.

It is another object of the present invention to provide a method and reagents for inhibiting binding of PSGL-1 to P-selectin and to other selectins.

It is a further object of the present invention to provide novel O-glycans, which are useful for modifying binding to P-selectin.

SUMMARY OF THE INVENTION

Sulfated, glycosylated peptides and the O-glycan structures uniquely present on PSGL-1 which bind to P-selectin have been developed using studies which identified the critical amino acid residues in the N-terminal region of PSGL-1, the importance of sulfation of the tyrosine residues, and the structure and role of the O-glycan carbohydrate structures coupled to threonine in the N-terminal region.

The examples demonstrate that PSGL-1 is sulfated, primarily on one or more of the tyrosine at residues 46, 48 and 51 which are required for high affinity binding to P-selectin. Studies demonstrate that PSGL-1 synthesized in human HL-60 cells can be metabolically-labeled with [$^{35}$S]sulfate that is incorporated primarily into tyrosine sulfate and that treatment of PSGL-1 with a bacterial arylsulfatase releases sulfate from tyrosine, resulting in a concordant decrease in binding to P-selectin. Moreover, the binding of PSGL-1 to P-selectin is blocked by antiserum directed against a synthetic peptide encompassing the three putative tyrosine sulfation sites near the N-terminus of PSGL-1.

Studies also demonstrate that the expression of PSGL-1 in a recombinantly engineered mammalian cell expressing two enzymes is required for proper glycosylation of PSGL-1: a fucosyltransferase (FTIII) and a core 2 β1-6-N-acetylglucosaminyltransferase. Comparative tests demonstrate that the glycosylation of PSGL-1 expressed in cells expressing these enzymes is more similar to the glycosylation of native PSGL-1 than the glycosylation of recombinant PSGL-1 expressed in COS or CHO cells not expressing the core 2 β1-6-N-acetylglucosaminyltransferase. The structures of the Ser/Thr-linked O-glycans of PSGL-1 synthesized by HL-60 cells were then metabolically-radiolabeled with $^3$H-sugar precursors. In control studies, the O-glycans on CD43 (leukosialin), a mucin-like glycoprotein also expressed by HL-60 cells, were analyzed and compared to those of PSGL-1. O-glycans were released from Ser/Thr residues by mild base/borohydride treatment of purified glycoproteins, and glycan structures were determined by a combination of techniques. In contrast to expectations, PSGL-1 is not heavily fucosylated; a majority of the O-glycans are disialylated or neutral forms of the core-2 tetrasaccharide Galβ1→4GlcNAcβ1→6(Baβ1→3)GalNAcOH. A minority of the O-glycans are α1,3 fucosylated that occur as two major species containing the sialyl Lewis x antigen—one species is a disialylated, monofucosylated glycan:

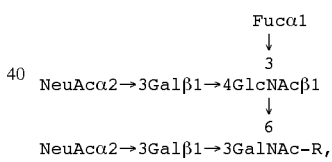

and the other is a monosialylated, trifucosylated glycan having a polylactosamine backbone:

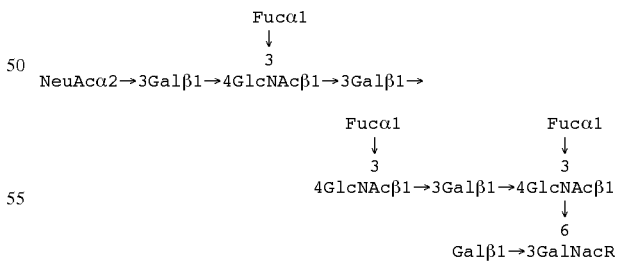

wherein R=H, OH, another sugar or an aglycone such as an amino acid. These results demonstrate that PSGL-1 contains unique fucosylated O-glycans that are involved in high affinity interactions between PSGL-1 and selectins.

BRIEF DESCRIPTION OF THE DRAWINGS

Figures 1A, 1B, 1C:
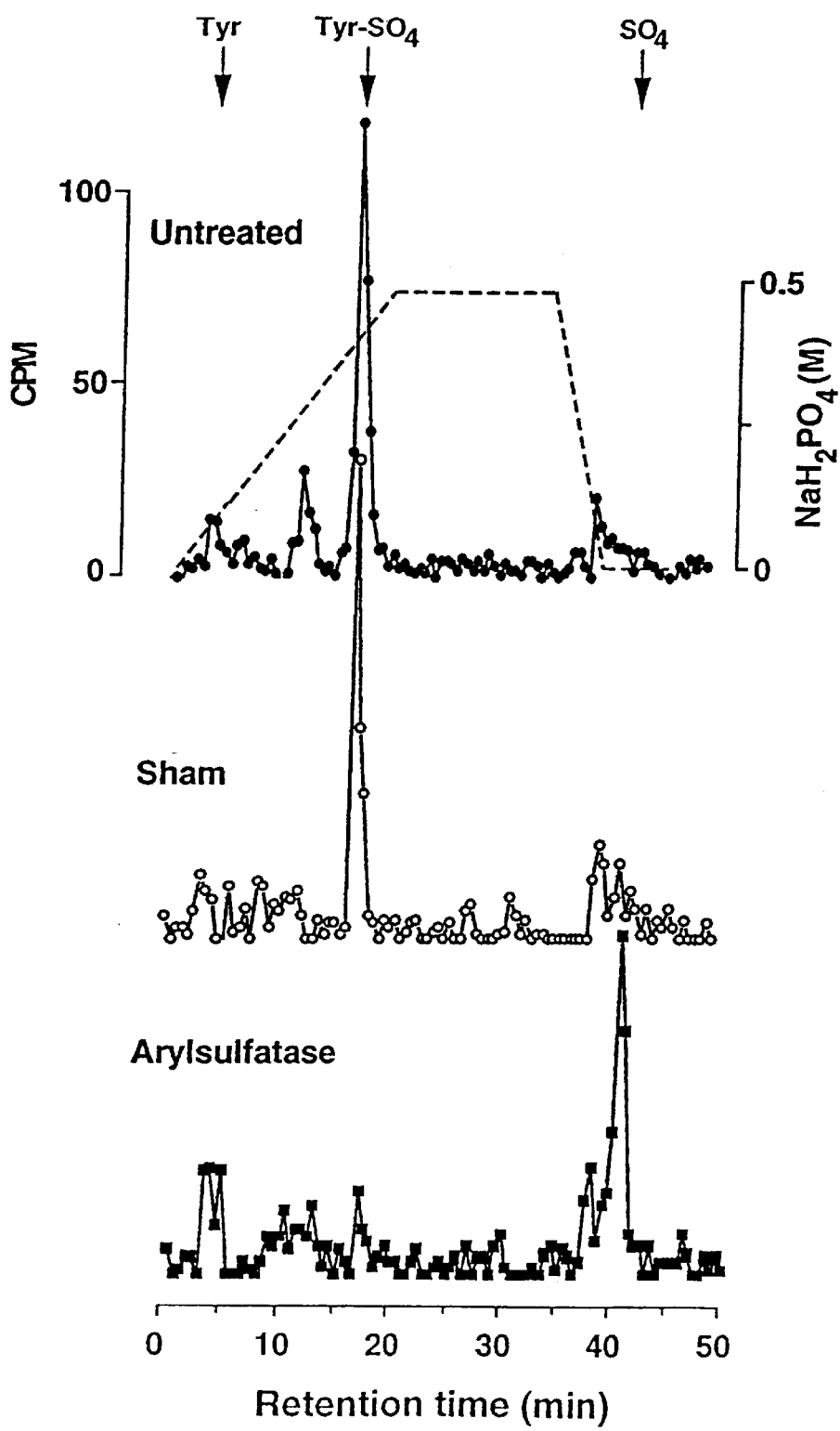

FIGS. 1A, 1B, and 1C are graphs of the retention time for anion exchange chromatography using a NaH$_2$PO$_4$, pH 3.0 gradient (dashed line) for enzymatically digested PSGL-1 demonstrating that PSGL-1 contains tyrosine sulfate that is sensitive to arylsulfatase. $^{35}$S-PSGL-1 hydrolyzed with strong base is shown in FIG. 1A; $^{35}$S-PSGL-1 hydrolyzed with strong base and sham-treated with 1000 mU of boiled arylsulfatase is shown in FIG. 1B; and $^{35}$S-PSGL-1 hydrolyzed with strong base and treated with 1000 mU of active enzyme is shown in FIG 1C. The retention times of tyrosine, tyrosine sulfate, and free sulfate are indicated. Free sulfate eluted at 40.0 min. Sulfated monosaccharides (Gal-6-sulfate, GIcNAc-6-sulfate, GalNAc-6-sulfate, and GalNAc-4-sulfate) eluted with similar retention times between 14 and 15 min.

Figure 2:
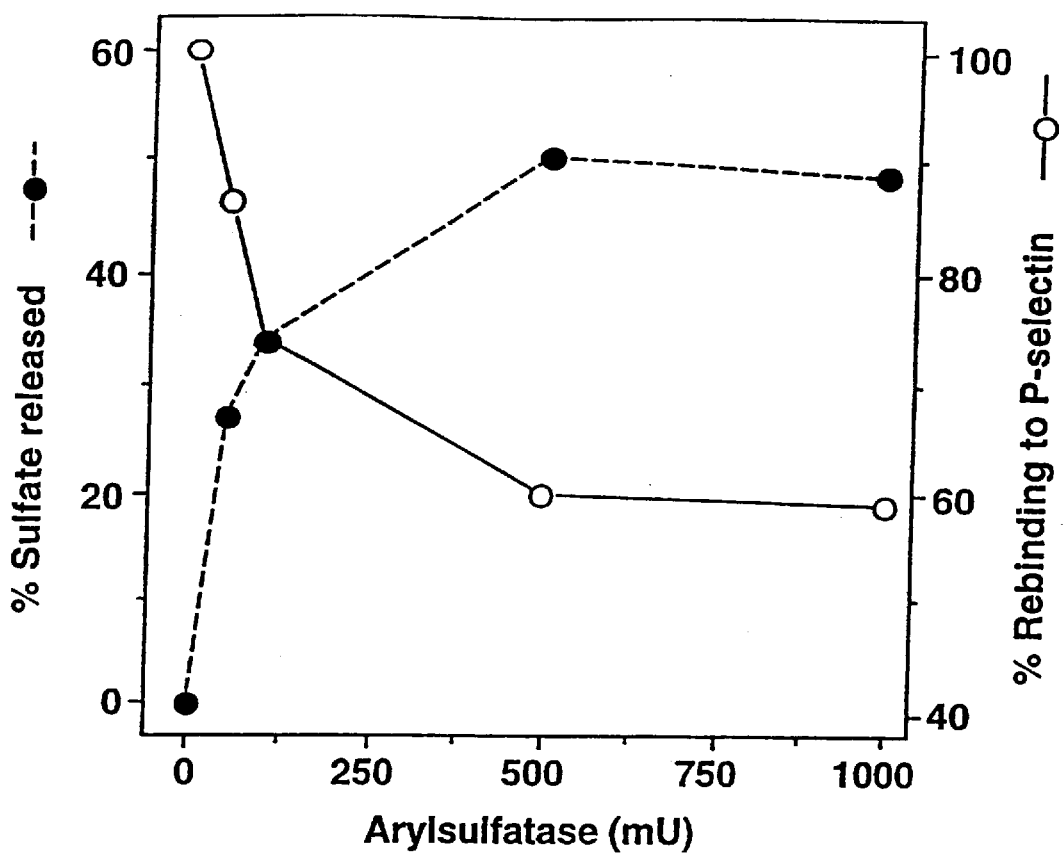

FIG. 2 is a graph of arylsulfatase release of [35S]sulfate from intact $^{35}$S-PSGL-1 and percent decrease in Ca$^{2+}$-dependent binding of $^{125}$-PSGL-1 to P- selectin, showing that tyrosine sulfate is important for P-selectin binding.

Figure 3A:
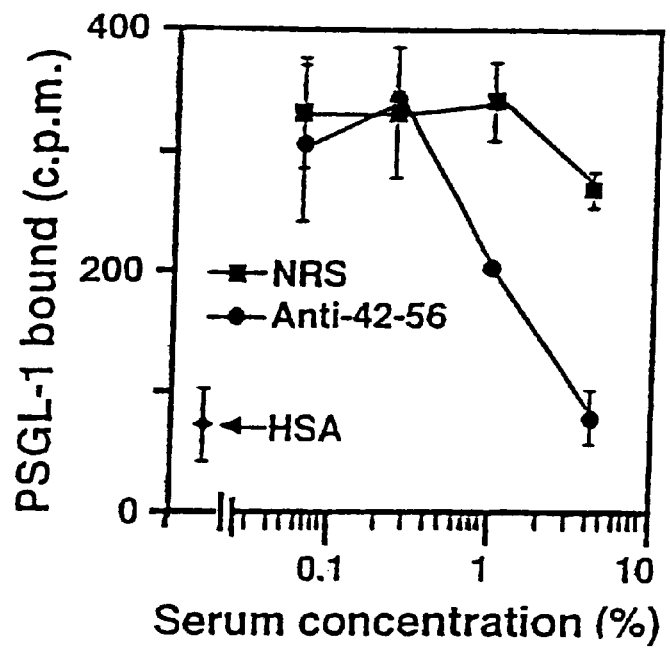
Figure 3B:
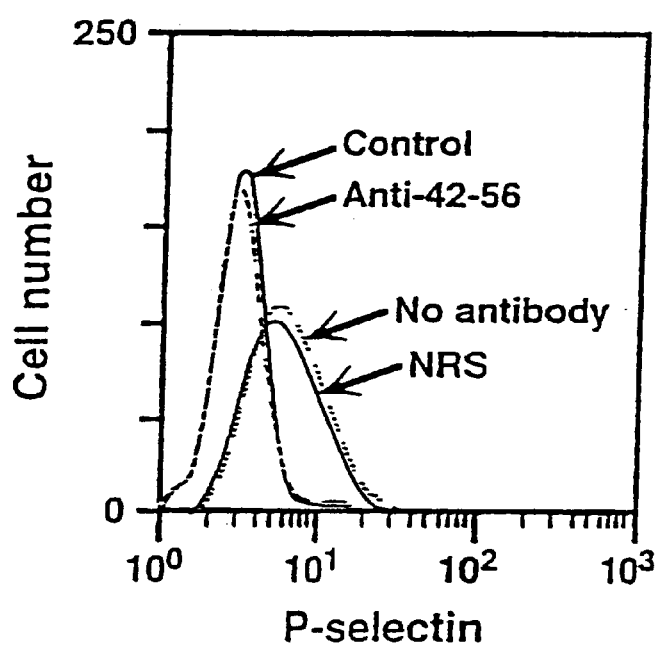

FIGS. 3A and 3B are graphs showing that a specific anti-peptide serum to PSGL-1 blocks binding of PSGL-1 to P-selectin. $^{125}$I-PSGL-1 was incubated in the presence of normal rabbit serum (NRS) or the antiserum directed against residues 42–56 of PSGL-1 (anti-42–56 amino acids) in microtiter plates containing immobilized recombinant soluble P-selectin or human serum albumin (HSA), and binding measured as a function of serum concentration, as shown in FIG. 3A. Platelet-derived P-selectin was incubated with HL-60 cells in the presence of 20% NRS or anti-42–56 amino acids serum. Binding of P-selectin was assayed by indirect immunofluorescence and flow cytometry, and cell number plotted against P-selectin binding, as shown in FIG. 3B.

FIGS. 4A–E, show that PSGL-1 fraction P-10-2b contains a minimum-sized glycan carrying the sLeX determinant. Fraction P-10-2b derived from $^3$H-GlcN-PSGL-1 was treated with exoglycosidases and analyzed by descending paper chromatography for 24 h. The β-eliminated glycans were first desialylated with neuraminidase and the neutral glycans were separated from released sialic acid by ion-exchange chromatography. (A) Chromatography of desialylated glycans; (B) desialylated glycans treated with β-galactosidase; (C) desialylated glycans treated with Streptomyces α1,3/4-fucosidase; (D) desialylated glycans treated with a combination of β-galactosidase, β-N-acetylhexosaminidase and Streptomyces α1,3/4-fucosidase. (E) β-eliminated glycans derived. from $^3$H-Fuc-PSGL-1 fraction P-10-2b were enzymatically desialylated and co-chromatographed in the same experiment. Migration of authentic standards is indicated: 5, Galβ1→4(Fucα1→3)GlcNAcβ1→6(Galβ1→3)GalNAcOH; 4, Galβ1→4 GlcNAβ1→6(Galβ1→3)GalNAcOH; 3*, GlcNAcβ1→6(Galβ1→3)GalNAcOH; 2, Galβ1→3 GalNAcOH; 1, GlcNAc.

FIGS. 5A and B, show that PSGL-1 fraction P-10-2a consists of a sialyjated, polylactosamine-containing O-glycan that is trifucosylated. Fraction P-10-2a derived from $^3$H-GlcN-PSGL-1 was treated with exoglycosidase and analyzed by descending paper chromatrography for 24 h. The β-eliminated glycans were first desialylated with neuraminidase, and the released sialic acid was separated from neutral glycans before and after treatments with either endo-β-galactosidase, or a combination of β-galactosidase and β-N-acetylhexosaminidase. (B) Desialylated glycans were chemically defucosylated and analyzed before and after treatments with either endo-β-galactosidase or a combination of β-galactosidase plus β-N-acetylhexosaminidase. Migration of authentic standards is indicated: 3, Galβ1→3GlcNAcβ1→3Galβ1; 3*, GlcNAcβ1→6(Galβ1→3)GalNAcOH; 2, Galβ1→4GlcNAc; 1, GlcNAc.

Figure 6:
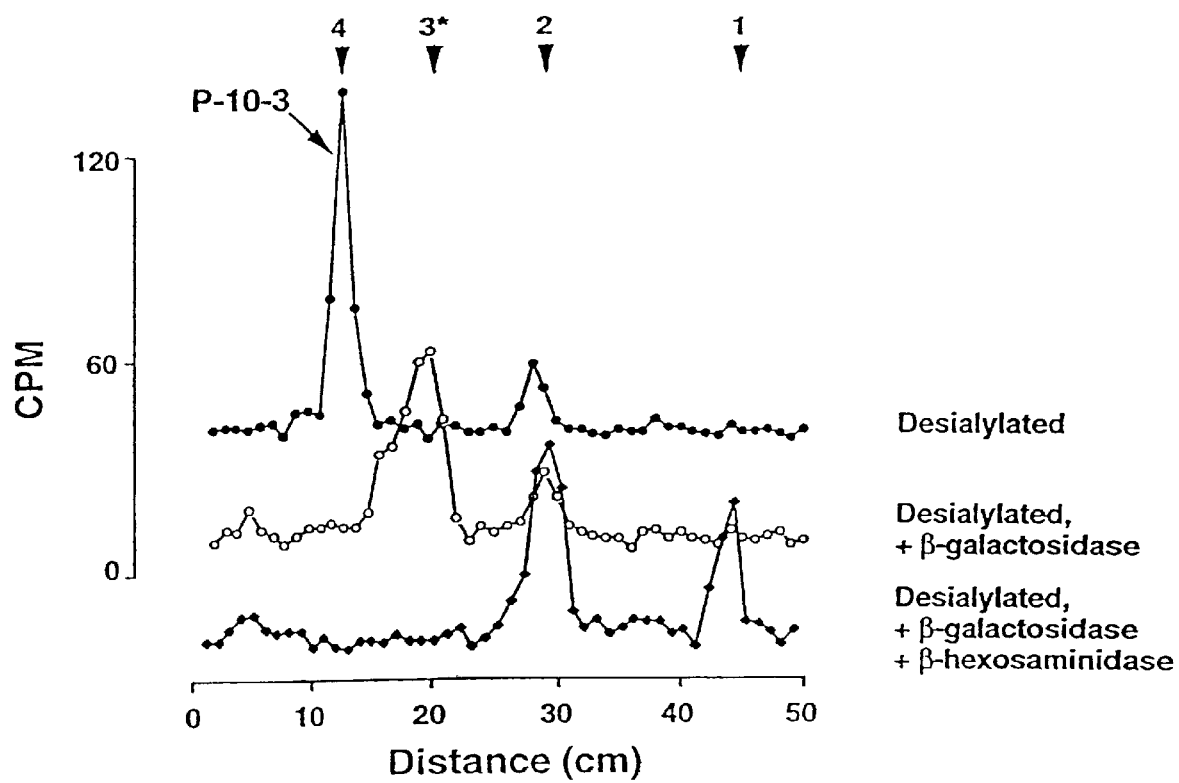

FIG. 6 shows that P-10-3 glycans contain the neutral core-2 tetrasaccharide. $^3$H-GlcN-P-10-3 was treated with neuraminidase and the released sialic acid separated from neutral glycans by QAE-Sephadex chromatography. The desialylated glycans were analyzed by descending paper chromatography for 18 h before and after treatment with either β-galactosidase alone, or β-galactosidase plus β-N-acetylhexosaminidase. Migration of authentic standards is indicated: 4, Galβ1→4GlcNAcβ1→6(Galβ1→3)GalNAcOH; e*, GlcNAcβ1→6(Galβ1→3) GalNAcOH; 2, Galβ1→4GlcNAc; 1,GlcNAc.

FIG. 7 are structures and relative percentages of the O-glycans in PSGL-1.

DETAILED DESCRIPTION OF THE INVENTION

Pharmaceutical and Diagnostic Peptides

Based on the information obtained from the examples described below, one can synthesize using recombinant techniques or peptide synthesizers followed by chemical or enzymatic sulfation and glycosylation, peptides which are useful for inhibiting binding of P-selectin and other selectins to PSGL-1, as described by the foregoing general formula and reference to the figures and examples below. The peptides preferably include at a minimum one of the three tyrosines at the amino terminus of the protein (residues 46, 48, and 51 of Sequence Listing ID No. 1), at least one of which is sulfated (—SO$_4$), and preferably include at least one threonine or serine which is suitable for O-linked glycosylation, for example, the threonine residue at amino acid residue 57 of Sequence Listing ID No. 1. An example of a minimum useful peptide corresponds to residues 48 to 57 of Sequence ID No. 1, as well as peptides having conservative substitutions which do not alter binding of the peptide to P-selectin. As demonstrated by the examples, it is important that the peptide include a core-2, sialylated, fucosylated O-glycan, as demonstrated in the following examples.

Amino acid sequence modifications fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis. Amino acid substitutions are typically of single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions

| Original Residue | Exemplary Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | Leu; ile |
| Phe | met; leu; tyr |
| Ser | thr |
| Thr | ser |
| Trp | tyr |
| Tyr | trp; phe: |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W. H. Freeman & Co., San Francisco pp 79–86 [1983]), acetylation of the N-terminal amine and, in some instances, amidation of the C-terminal carboxyl.

Methods of Preparation of Peptides

The peptides can generally be prepared following known techniques, as described for example in the cited publications, the teachings of which are specifically incorporated herein. Since the preferred peptides are both glycosylated and sulfated, it is preferable to express the peptides in appropriate mammalian host cells as described below.

Chemical Synthesis

In a preferred synthetic method, the peptides are prepared following the solid-phase synthetic technique initially described by Merrifield in *J. Amer. Chem. Soc.*, 85, 2149–2154 (1963). Other techniques may be found, for example, in M. Bodanszky, et al., *Peptide Synthesis*, second edition, (John Wiley & Sons, 1976), as well as in other reference works known to those skilled in the art.

Appropriate protective groups usable in such syntheses and their abbreviations will be found in the above text, as well as in J. F. W. McOmie, Protective Groups in Organic Chemistry, (Plenum Press, New York, 1973). The common protective groups used herein are t-butyloxycarbonyl (Boc), fluorenylmethoxycarbonyl (FMOC), benzyl (Bzl), tosyl (Tos), o-bromophenylmethoxycarbonyl (BrCBZ or BrZ), phenylmethoxycarbonyl (CBZ or Z), 2-chlorophenylmethoxycarbonyl, (2-Cl-CBZ or Cl-Z), 4-methoxy-2,3,6-trimethylbenzenesulfonyl (Mtr), formyl (CHO), and tertiary butyl (t-Bu). Trifluoroacetic acid (TFA), Methylene chloride ($CH_2Cl_2$), N,N-Diisopropylethylamine (DIEA), N-Methylpyrrolidone (NMP), 1-Hydroxybenzotriazole (HOBT), Dimethylsulfoxide DMSO, Acetic anhydride ($Ac_2O$).

General synthetic procedures for the synthesis of peptides by solid phase peptide synthesis using $N^\alpha$-Boc protection.

| | REPETITIONS | TIME |
|---|---|---|
| 1. 25% TFA in $CH_2Cl_2$ | 1 | 3 min |
| 2. 50% TFA in $CH_2Cl_2$ | 1 | 16 min |

-continued

| | REPETITIONS | TIME |
|---|---|---|
| 3. CH$_2$Cl$_2$ | 5 | 3 min |
| 4. 5% DIEA in NMP | 2 | 4 min |
| 5. NMP | 6 | 5 min |
| 6. Coupling step | 1 | 57 min |
|    a. Preformed BOC-Amino Acid-HOBT active ester in NMP | | 36 min |
|    b. DMSO | | 16 min |
|    c. DIEA | | 5 min |
| 7. 10% Ac$_2$O, 5% DIEA in NMP | 1 | 9 min |
| 8. CH$_2$Cl$_2$ | 5 | 3 min |

General synthetic procedures for solid phase peptide synthesis using N$^\alpha$-FMOC protection.

| | REPETITIONS | TIME |
|---|---|---|
| 1. 20% piperidine in NMP | 1 | 3 min |
| 2. 20% piperidine in NMP | 1 | 15 min |
| 3. NMP | 6 | 9 min |
| 4. Coupling Preformed FMOC-Amino Acid-HOBT active ester in NMP | 1 | 71 min |
| 5. NMP | 6 | 7 min |

N-terminal acetylation on the deprotected N$^\alpha$-amino group of peptides synthesized using either Boc or FMOC strategies is accomplished with 10% Ac$_2$O and 5% DIEA in NMP, followed by washing of the peptide resin with NMP and/or CH$_2$Cl$_2$.

Expression Systems

As demonstrated by the following examples, the sulfated, glycosylated PSGL-1 peptides described herein which bind to P-selectin are those having at least one sulfate bound to a tyrosine residue and appropriate glycosylation. Comparative studies of recombinant PSGL-1 expressed in mammalian cells (COS cells) which express a fucosyltransferase with purified native PSGL-1 demonstrated that the glycosylation was substantially different. A new expression system has therefore been developed which results in more natural glycosylation of PSGL-1. The expression system is based on a mammalian expression system which expresses at least two glycosyltransferases: fucosyltransferase III (FTIII) and core 2 β1-6-N-acetylglucosaminyltransferase. In a preferred embodiment, the cell line is based on a well characterized expression line such as COS or CHO cells which are transfected with the cDNA encoding the two enzymes. The cDNAs are shown below as Sequence Listing ID Nos. 2 and 3, respectively. Sequence Listing ID No. 2 encodes a human α(1,3/1,4)fucosyltransferase (FTIII) described by Kukowska-Latallo, et al., Genes & Devel. 4, 1288–1303 (1990). Sequence Listing ID No. 3 encodes Core 2 β1- 6-N-acetylglucosaminyltransferase (EC 2.4.1.102), as reported by Bierhuizen and Fukuda, Proc. Natl. Acad. Sci. USA 89, 9326–9330 (1992). Prior studies had failed to recognize the importance of the core 2 6-N-acetylglucosyaminyltransferase for modification of PSGL-1 to confer binding to P-selectin. Alternatively, the expression system can be selected based on expression of either or both enzymes naturally, with the second enzyme being provided by transfection if necessary.

The cDNAs are introduced into the cells under the control of appropriate promoters and, optionally, enhancers and selection sequences.

Preferred promoters controlling transcription from vectors in mammalian host cells may be obtained from various sources, for example, the genomes of viruses such as: Simian Virus 40 (SV40), adenovirus, retroviruses, hepatitis-B virus and most preferably cytomegalovirus, or from heterologous mammalian promoters, e.g. beta actin promoter. The early and is late promoters of the SV40 virus are conveniently obtained as an SV40 restriction fragment which also contains the SV40 viral origin of replication. Fiers et al., Nature, 273: 113 (1978). The immediate early promoter of the human-cytomegalovirus is conveniently obtained as a HindIII restriction fragment. Greenaway, P. J. et al., Gene 18 355–360 (1982). Of course, promoters from the host cell or related species also are useful.

Transcription of a DNA encoding a desired protein by higher eukaryotes is increased by inserting an enhancer sequence into the vector. Enhancers are cis-acting elements of DNA, usually from about 10 to 300 bp,. that act on a promoter to increase its transcription initiation capability. Enhancers are relatively orientation and position independent having been found 5' (Laimins, L. et al., Proc. Natl. Acad. Sci. 78: 993) and 3' (Lusky, M. L., et al., Mol. Cell Bio. 3: 1108 (1983)) to the transcription unit, within an intron (Banerji, J. L. et al., Cell 33: 729 (1983)) as well as within the coding sequence itself (Osborne, T. F., et al., Mol. Cell Bio. 4 1293 (1984)). Many enhancer sequences are now known from mammalian genes (globin, elastase, albumin, α-fetoprotein and insulin). Typically, however, one will use an enhancer from an eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding the desired protein. The 3' untranslated regions also include transcription termination sites.

Expression vectors may contain a selection gene or selectable marker. Examples of suitable selectable markers for mammalian cells are dihydrofolate reductase (DHFR), thymidine kinase or neomycin. When the. selectable markers are successfully transferred into a mammalian host cell, the transformed mammalian host cell survives when placed under selective pressure. There are two widely used distinct categories of selective regimes. The first category is based on a cell's metabolism and the use of a mutant cell line which lacks the ability to grow independent of a supplemented media. Two examples are: DHFR-minus CHO cells and mouse LTK cells. These cells lack the ability to grow without the addition of such nutrients as thymidine or hypoxanthine. Since these cells lack certain genes necessary. for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec, Appl. Genet.* 1: 327 (1982), mycophenolic acid, Mulligan, R. C. and Berg, P. *Science* 209: 1422 (1980) or hygromycin, Sugden, B. et al., *Mol. Cell. Biol*, 5 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the vectors in higher eukaryotes include: monkey kidney CVI line transformed by SV40 (COS-7, ATCC CRL 1651); human embryonic kidney line (293, Graham, F. L. et al. *J. Gen Virol.* 36: 59 (1977)); baby hamster kidney cells (BHK, ATCC CCL 10); chinese hamster ovary-cells-DHFR (CHO, Urlaub and Chasin, *Proc. Natl. Acad. Sci. USA* 77 4216, (1980)); mouse sertoli cells (TM4, Mather, J. P., *Biol. Reprod.* 23: 243–251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL51); and, TRI cells (Mather, J. P. et al., *Annals N. Y. Acad. Sci* 383; 44–68 (1982)). Host cells can be transformed with the expression vectors and cultured in conventional nutrient media modified as is appropriate for inducing promoters, selecting transformants or amplifying genes. The culture conditions, such as temperature and pH, are those previously used with the host cell selected for expression.

Preparation of Diagnostic and Therapeutic Agents Derived from the Protein or Carbohydrate Components of the Glycoprotein Ligand for P-selectin.

The glycoprotein ligand for P-selectin described above has a variety of applications as diagnostic reagents and, potentially, in the treatment of numerous inflammatory and thrombotic disorders.

Diagnostic Reagents.

Antibodies to the ligand can be used for the detection of human disorders in which P-selectin ligands might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, immunoperoxidase or immunogold analysis, or other methods known to those skilled in the arts.

Antibodies directed specifically to protein or carbohydrate components of the ligand can be used to distinguish defects in expression of the core protein or in glycosyltransferases and/or modifying enzymes that construct the proper oligosaccharide chains on the protein. The antibodies can also be used to screen cells and tissues other than leukocytes for expression of the protein or carbohydrate components of the ligand for P-selectin.

Complementary DNA clones encoding the protein component of the ligand can be isolated and sequenced. These cDNA probes can be used as diagnostic reagents to examine expression of RNA transcripts for the ligand in leukocytes and other tissues by standard procedures such as Northern blotting of RNA isolated from cells and in situ hybridization of tissue sections.

A similar approach can be used to determine qualitative or quantitative disorders of P-selectin itself. The glycoprotein ligand, carbohydrates, or appropriate derivatives thereof, is labeled and tested for its ability to bind to P-selectin on activated platelets from patients with disorders in which P-selectin might be defective.

The ligand, or components thereof, can also be used in assays of P-selectin binding to screen for compounds that block interactions of P-selectin with the ligand.

Clinical Applications.

Since P-selectin has several functions related to leukocyte adherence, inflammation, tumor metastases, and coagulation, clinically, compounds which interfere with binding of P-selectin and/or the other selecting, including E-selectin and L-selectin, such as the carbohydrates, can be used to modulate these responses. These compounds include PSGL-1 or fragments thereof, antibodies to PSGL-1 or fragments thereof. For example, the glycoprotein ligand, or components thereof, particularly the carbohydrate moieties, can be used to inhibit leukocyte adhesion by competitively binding to P-selectin expressed on the surface of activated platelets or endothelial cells. Similarly, antibodies to the ligand can be used to block cell adhesion mediated by P-selectin by competitively binding to the P-selectin ligand on leukocytes or other cells. These therapies are useful in acute situations where effective, but transient, inhibition of leukocyte-mediated inflammation is desirable. In addition, treatment of chronic disorders may be attained by sustained administration of agents, for example, by subcutaneous or oral administration.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. Specifically, certain carcinoma cells have been demonstrated to bind to both E-selectin, as reported by Rice and Bevilacqua. *Science* 246:1303–1306 (1991), and P-selectin, as reported by Aruffo, et al., *Proc. Natl. Acad. Sci. USA* 89:2292–2296 (1992), Stone and Wagner, *I. Clin. Invst*. 92:804–813 (1992). The association of platelets with. metastasizing tumor cells has been well described, suggesting a role for platelets in the spread of some cancers. Since P-selectin is expressed on activated platelets, it is believed to be involved in association of platelets with at least some malignant tumors.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia. P-selectin is also inappropriately expressed on the surface of endothelial cells overlying atheromas, where it may mediate the initial attachment of monocytes that then migrate into the atheroma (Johnson-Tidey, et al., *Am. J. Path*. 144:952–961, 1994).

Another area of potential application is in the treatment of rheumatoid arthritis and other autoimmune or inflammatory disorders.

In these clinical applications, the peptides or isolated O-glycan, or fragments thereof, described herein, can be administered to block selectin-dependent interactions by binding competitively to P-selectin expressed on activated cells. In addition, antibodies to the protein and/or carbohydrate components of the ligand, or fragments thereof, can be administered. The antibodies are preferably of human origin or modified to delete those portions most likely to cause an immunogenic reaction.

Peptides as described herein can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Carbohydrate components (the O-glycan structures or components thereof) of the ligand or the antibodies, in an appropriate pharmaceutical carrier, are preferably administered intravenously where immediate relief is required. The carbohydrate(s) can also be administered intramuscularly, intraperitoneally, subcutaneously, orally, as the carbohydrate, conjugated to a carrier molecule, or in a drug delivery device. The carbohydrate can be modified chemically to increase its in vivo half-life.

The carbohydrate can be isolated from cells expressing the carbohydrate, either naturally or as a result of genetic engineering as described in the transfected mammalian cell examples, or, preferably, by synthetic means. These methods are known to those skilled in the art. In addition, a large number of additional glycosyltransferases have been cloned (J. C. Paulson and K. J. Colley, *J. Biol. Chem*. 264:17615–17618, 1989). Accordingly, workers skilled in the art can use a combination of synthetic chemistry and enzymatic synthesis to make pharmaceuticals or diagnostic reagents.

Carbohydrates that are biologically active are those which inhibit binding of leukocytes to P-selectin. Suitable pharmaceutical vehicles for administration to a patient are known to those skilled in the art. For parenteral administration, the carbohydrate will usually be dissolved or suspended in sterile water or saline. For enteral administration, the carbohydrate will be incorporated into an inert carrier in tablet, liquid, or capsular form. Suitable carriers may be starches or sugars and include lubricants, flavorings, binders, and other materials of the same nature. The carbohydrate can also be administered locally at a wound or inflammatory site by topical application of a solution or cream.

Alternatively, the carbohydrate may be administered in, on or as part of, liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the carbohydrate can be incorporated and the microspheres, or composite of microspheres, implanted for slow release over a period of time, ranging from days to months. See, for example, U.S. Pat. No. 4,906,474, 4,925,673, and 3,625,214.

The carbohydrates should be active when administered parenterally in amounts above about 1 μg/kg of body weight. For treatment of most inflammatory disorders, the dosage range will be between 0.1 to 30 mg/kg of body weight. A dosage of 70 mg/kg may be required for some of the carbohydrates characterized in the examples.

The criteria for assessing response to therapeutic modalities employing antibodies or carbohydrate is dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

The present invention will be further understood by reference to the following non-limiting examples.

EXAMPLE 1

Determination of the Structure and Function of the Oligosaccharides Attached to PSGL-1

The effects of various glycosidases on the structure and function of PSGL-1 from human neutrophils was determined. This molecule, unlike recombinant PSGL-1 expressed in COS cells with FTIII, is largely resistant to treatment with endo-α-N-acetylgalactosaminidase, suggesting that it has few simple core 1 Galβ1-3GalNAc disaccharides linked to serine or threonine. Human neutrophil PSGL-1 displays sLe$^x$ and its nonsialylated counterpart, Le$^x$, primarily on O-linked poly-N-acetyllactosamine. These data suggest that PSGL-1 on human neutrophils presents an array of sialylated, fucosylated, O-linked poly-N-acetyllactosamine that P-selectin preferentially recognizes as compared to recombinant PSGL-1 expressed in COS cells with FTIII.

The effects of glycosidases on purified, radioiodinated PSGL-1 from human neutrophils were examined to further characterize the structure and function of the attached oligosaccharides. PSGL-1 was found to have poly-N-acetyllactosamine, only some of which could be removed with endo-β-galactosidase. The majority of the Le$^x$ and sLe$^x$ structures were on endo-β-galactosidase-sensitive chains. Peptide: N-glycosidase F (PNGaseF) treatment removed at least two of the three possible N-linked oligosaccharides from PSGL-1. Expression of Le$^x$ and sLe$^x$ was not detectably altered by PNGaseF digestion, indicating that these structures were primarily on O-linked poly-N-acetyllactosamine. Endo-β-galactosidase-treated PSGL-1 retained the ability to bind to P-selectin, suggesting that some of the oligosaccharides recognized by P-selectin were either on enzyme-resistant poly-N-acetyllactosamine or on chains which lack poly-N-acetyllactosamine. PNGaseF treatment did not affect the ability of PSGL-1 to bind to P-selectin, demonstrating that the oligosaccharides required for P-selectin recognition are O-linked. These data demonstrate that PSGL-1 from human neutrophils displays complex, sialylated, and fucosylated O-linked poly-N-acetyllactosamine that promote high affinity binding to P-selectin.

Materials and Methods

The abbreviations used are: CHO, Chinese hamster ovary; Con A, Concanavalin A; HSA, human serum albumin; Le$^x$, Lewis x; PBS, phosphate-buffered saline; PAGE, polyacrylamide gel electrophoresis; PNGaseF, peptide:N-glycosidase F; PSGL-1, P-Selectin Glycoprotein Ligand 1; sLe$^x$, sialyl Lewis x; tES, truncated soluble E-selectin; tPS, truncated soluble P-selectin; WGA, wheat germ agglutinin.

Materials—Triton X-100, Brij-58, and sialidase from *Arthrobacter ureafaciens* (75 U/mg, EC 3.2.1.18) were obtained from CalBioChem-Behring Corp. (La Jolla, Calif.). Iodobeads®, 3M Emphaze® Biosupport Medium, and Protein A Sepharose CL4B were from Pierce Chemical Co. (Rockford, Ill.). Endo-β-galactosidase from *Escherichia freundii* (5 U/mg, EC 3.2.1.103) was obtained from V-Labs, Inc. (Covington, La.). Streptomyces sp.142 α1,3/4-L-fucosidase (EC 3.2.1.51) was obtained from PanVera Corp. (Madison, Wis.) and β-N-acetylglucosaminidase from Jack Bean (EC 3.2.1.30, 53 U/mg) was from Sigma Chemical Co. (St. Louis, Mo.). Recombinant peptide:N-glycosidase F (EC 3.2.2.18, 25,000 U/mg, PNGase F), and endo-α-N-acetylgalactosaminidase from *Diplococcus pneumoniae* (EC 3.2.1.97, O-glycanase®) were purchased from Genzyme Corp. (Cambridge, Mass.). Concanavalin A Sepharose (Con A, 10 mg/ml resin) was from Pharmacia/LKB (Uppsala, Sweden). Wheat germ agglutinin (WGA) agarose (7.6 mg/ml resin) and tomato lectin were from Vector Laboratories, Inc. (Burlingame, Vt.). Tomato lectin was coupled to cyanogen bromide-activated Sepharose to a density of 2 mg/ml resin in the presence of 7.5 mg/ml chitotriose.

Antibodies—The anti-human P-selectin mAbs S12 and G1 were prepared and characterized as previously described by McEver and Martin (1984), Geng, et al., (1990). The anti-human E-selectin mAbs CL2 and CL37 (Mulligan, et al., *J. Clin. Invest.* 88, 1396–1406 (1991)) were provided by C. Wayne Smith (Baylor College of Medicine, Houston, Tex.). LeuM1 (CD15, IgM) was purchased from Becton-Dickinson & Co. (San Jose, Calif.) The CSLEX-1 hybridoma (HB 8580) was purchased from the American Type Culture Collection and the IgM mAb was purified from ascites fluid by boric acid precipitation and gel filtration on Sepharose CL4B in PBS, pH 7.4 as described by Shattil, et al., *J. Biol. Chem.* 260, 11107–11114 (1985). Goat anti-mouse μ-chain specific IgG and MOPC104E (IgM) were purchased from Cappel-Organon Technika (Durham, N.C.).

Peptide Antisera Production and Immunoprecipitations. Peptides corresponding to residues 42–56 (QATEYEYLDYDFLPEC) (Sequence ID No. 1) and 354–376 (CISSLLPDGGEGPSATANGGLSK) (Sequence ID No. 1) of the cDNA-derived amino acid sequence of PSGL-1 were synthesized on an Applied Biosystems Model 431 peptide synthesizer. Peptide 42–56 was coupled to maleimide-activated keyhole limpet hemocyanin (Pierce Chemical Co.) through the added cysteine and injected into New Zealand white rabbits (Montana State University Animal Resources Center). Immune sera were collected and used to immunoprecipitate $^{125}$I-PSGL-1. Protein A beads (25 μl, 50% suspension) were preincubated with 1 μl of a 1:4 dilution of either normal or immune rabbit serum for 90 min at 37° C. The beads were washed once with 0.1 M NaCl, 20 mM MOPS, pH 7.5, 0.1% Triton X-100 (MBS/0.1% Triton). Purified $^{125}$I-PSGL-1 or radioiodinated-WGA eluate was then incubated with the beads in the presence or absence of 0.2 mg/ml of either the immunizing peptide or PSGL-1 peptide 354–376 which served as a negative control. After a 90 min incubation at 37° C. the beads were washed five times with MBS/0.1% Triton and the eluted by boiling for 5 min with SDS sample buffer (Laemmli, *Nature* 227, 680–685 (1970)). Immunoprecipitates were analyzed by SDS-PAGE, followed by autoradiography.

Generation of CHO D⁻ cells Stably Expressing a Soluble Form of E-selectin. An expression plasmid (ELAM-1:BBG 57, obtained from British BioTechnology Products, Ltd.) containing the full-length cDNA for human E-selectin was used as a template in the polymerase chain reaction to modify the 5' and 3' ends of E-selectin for high level production of recombinant soluble E-selectin in CHO D⁻ cells. The oligonucleotide pair (5' GTC CCT CTA GAC CAC CAT GAT TGC TTC ACA GTT T+5' TCC CGG TCG ACT TAG GGA GCT TCA CAG GT) (Sequence Listing ID Nos. 4 and 5, respectively) used in the polymerase chain reaction was designed to introduce an Xba I site and a perfect Kozak sequence (Kozak, *Nucleic Acids Res.* 9, 5233–5252 (1981)) preceding the E-selectin initiator codon, and to introduce a Sal I site following the stop codon introduced after amino acid 550 located between the sixth consensus repeat and the transmembrane domain of full-length E-selectin. DNA sequence analysis verified the changes generated by the polymerase chain reaction as well as the integrity of the remainder of the E-selectin cDNA. The truncated E-selectin (tES) gene was then introduced as an Xba I-Sal I fragment into the mammalian expression vector pDSRα2 (European patent application A20398753) that was modified to include unique Xba I and Sal I restriction sites. The tES expression vector was transfected into a CHO cell line deficient in dihydrofolate reductase (DHFR-minus CHO) (Urlaub, et al., *Proc. Natl. Acad. Sci. USA* 77, 4216–4220 (1980)), and transfectants were selected in medium lacking hypoxanthine and thymidine (Bourdrel, et al., *Protein Exp. Purif.* 4, 130–140 (1993)). An RNase protection assay was used to screen for transfectants that had high levels of E-selectin-specific mRNA (Turner, et al., *Blood* 80, 374–381 (1992)).

Protein Purification. PSGL-1 was purified from human neutrophil membranes prepared as described by Moore, et al., (1992), with the following modifications. Neutrophil membranes extracted with 5% Triton X-100 in 0.1 M NaCl, 20 mM MOPS, pH 7.5, 0.02% NaN$_3$ were applied to WGA-agarose, and bound proteins were eluted with 0.5 M N-acetylglucosamine (WGA eluate). After extensive dialysis against 0.1 M NaCl, 20 mM MOPS, pH 7.5, 0.02% NaN$_3$, 0.02% Brij-58, 2 mM CaCl$_2$, 2 mM MgCl$_2$ (equilibration buffer), the WGA eluate was loaded on a truncated P-selectin (tPS)-Emphaze column (10 mg lectin/ml resin). The column was extensively washed with equilibration buffer and eluted with 5 mM EDTA. Ligand-containing fractions were pooled and loaded on a Mono Q PC 1.6/5 column equilibrated with 0.1 M NaCl, 20 mM MOPS, pH 7.5, 2 mM EDTA, 0.02% NaN$_3$, 0.02% Brij-58 using a SMART® Micro Separation System (Pharmacia/LKB). The column was developed with a 2-ml linear gradient (0.1–1.0 M NaCl) at 50 μml/min. Aliquots of the fractions were iodinated with Na$^{125}$I using Iodobeads® according to the instructions of the manufacturer. The purity of the fractions was assessed by SDS-PAGE and autoradiography of the iodinated fractions.

A recombinant soluble form of P-selectin (tPS) truncated after the ninth consensus repeat was immunoaffinity purified from conditioned medium of permanently transfected 293 cells as described by Ushiyama, et al., (1993). As determined by sedimentation velocity and equilibrium analysis, tPS is an asymmetric monomer with a molecular weight of 103,600 Da. The $E_{280}^{1\%}$ for tPS is 12.3.

Recombinant soluble truncated E-selectin (tES) was immunoaffinity purified from conditioned medium of CHO D⁻ cells stably secreting tES. Cells were cultured in equal parts of Dulbecco's modified Eagle's medium (DMEM) and Ham's F-12 nutrient mixture, supplemented with 10% fetal bovine serum, 10 U/ml penicillin, and 10 mg/ml streptomycin. At confluence, the cells were shifted to serum-free medium, and conditioned medium was harvested every 7 days. Conditioned medium was clarified, sterile-filtered, using two Sartorius filters (10 μm and 0.2 μm) connected in series, and then concentrated 50-fold (Filtron Maximate, 10 kDa MW$_{co}$). The anti-E-selectin mAb H18/7 (Bevilacqua, et al., *Proc. Nati. Acad. Sci. USA* 84, 9238–9242 (1987)) was coupled to cyanogen bromide-activated Sepharose to a density of 6 mg/ml resin. The H18/7-Sepharose column was equilibrated at 4° C. with PBS, pH 7.5, containing 1 mM CaCl$_2$ and 1 mM MgCl$_2$ and 500 ml of concentrated medium was loaded on the column (V$_T$=200 ml) at a flow rate of 10 cm/h. The column was eluted with 0.1 M glycine, pH 2.7 and the fractions were rapidly neutralized by addition of Tris-HCl, pH 7.5 to a final concentration of 0.1 M. The eluate was dialyzed against 25 mM sodium phosphate, pH 7.5, and loaded on a Q-High Performance anion-exchange column (V$_T$=200 ml, Pharmacia) equilibrated in the same buffer. The column was developed with a linear gradient of NaCl (0.17–0.22 M). Purity was assessed by SDS-PAGE and by N-terminal sequence analysis. Protein concentration was determined using an $E_{280}^{1\%}$=12.5 that was calculated using the method of Gill, and von Hippel, *Anal. Biochem.* 182, 319–326 (1989). The yield was 250 mg of tES per approximately 500 ml of concentrated conditioned medium.

Sedimentation Equilibrium Analysis of Soluble tES. Sedimentation equilibrium experiments were conducted using a 4-hole titanium rotor, short column kel-f centerpieces, and sapphire windows in a Beckman Optima XLA analytical ultracentrifuge equipped with on-line Rayleigh interference optics. Data were acquired at rotor speeds of 10,000, 15,000, 20,000, and 25,000 rpm at 20° C. using a television-based camera and an on-line acquisition and analysis system (Laue, T. M. (1981) Ph.D. Dissertation, University of Connecticut, Storres, CT; Laue, et al., (1992) in *Analytical Ultracentrifugation in Biochemistry and Polymer Science* (Harding, S., Rowe, A., and Horton, J. C., eds) pp. 90–125, Royal Society of Chemistry, London). Samples were loaded at concentrations of approximately 1.0, 0.5, 0.25, and 0.13 mg/ml in PBS, pH 7.4. Data were collected at intervals after the estimated time to equilibrium and tested for equilibrium by subtracting successive scans (Yphantis, D. A. (1964) *Biochemistry* 3, 297–317)). The data within the optical window were selected using the program REEDIT (provided by David Yphantis). Data were analyzed to estimate the monomer molecular weight of tES using the NONLIN program (Yphantis, D. A. (1964) *Biochemistry* 3, 297–317). Three or more channels of sedimentation equilibrium data obtained at different loading concentration of tES, radial positions, and angular velocities were fit by simultaneous nonlinear least-squares analysis. For molecular weight calculations, the partial specific volume of tES was estimated to be 0.688 ml/g with an inaccuracy of ±0.03 ml/g to account for uncertainty in the carbohydrate composition of tES (Laue, et al. (1992)).

Sedimentation Velocity Analysis of Soluble tES. Sedimentation velocity experiments were conducted in the Beckman Optima XLA analytical ultracentrifuge using Rayleigh interference optics. Experiments were conducted at 60,000 rpm and 20° C., using a 4-hole titanium rotor, two-channel, charcoal-filled, epon centerpieces, and sapphire windows. Sample was loaded at a concentration of 0.5 mg/ml in PBS, pH 7.4. Sedimentation coefficients were determined from the time derivative of the concentration profile as described by. Stafford, W. (1992) *Anal. Biochem.* 203, 295–301.

Protein Iodinations. The mAbs G1 and CL2 (200 μg) were iodinated with 400 μCi carrier-free Na$^{125}$I (ICN Biomedical, Inc., Costa Mesa, Calif.) using Iodobeads®. Free $^{125}$I was removed by gel filtration through a Sephadex G-25 column (PD-10, Pharmacia) equilibrated in 0.1 M NaCl, 20 mM MOPS, pH 7.5, 0.1% Triton X-100. The labeled antibodies were then centrifuged for 30 min at 90,000×g in a TL-100 ultracentrifuge (Beckman, Palo Alto, Calif.). The concentration of labeled proteins was determined with a Micro BCA protein assay kit (Pierce) using the respective unlabeled proteins as standards. The specific activity of the labeled antibodies ranged from 0.5–1.0 μCi/μg protein.

PSGL-1 (approximately 0.5 μg) or WGA eluate (approximately 100 μg) was iodinated with 400 μCi Na$^{125}$I and desalted as described above. Radioabeled PSGL-1 was concentrated to approximately 200 μl using a Centicon-30® device (Pharmacia/LKB), and gel filtered on a Superose 6 PC 3.2/30 column equilibrated with 0.15 M NaCl, 20 mM MOPS, pH 7.5, 0.02% NaN$_3$, 0.1% Brij-58 using a SMART® Micro Separation System (Pharnacia/LKB). The specific activity of the radiolabeled ligand ranged from 14–30 μCi/μg protein. Labeled proteins were routinely greater than 95% trichloroacetic acid precipitable.

Binding of $^{125}$I-PSGL-1 to Immobilized tPS or tES. tPS or tES (50 μl, 10 μg/ml) in HBSS, 0.02% NaN$_3$ (HBSS/Az) were incubated overnight at 4° C. in microtiter plates (Immulon I Removawell® Strips, Dynatech Laboratories, Inc., Chantilly, Va.). After three washes with HBSS/Az the wells were blocked with HBSS/Az/1% human serum albumin (HSA) for 2 h at 22° C. The wells were then washed once with HBSS/Az and $^{125}$I-PSGL-1 diluted in HBSS/Az/0.1% HSA was added (50 μl, 5,000–10,000 cpm/well). After 1 h at 22° C. the wells were rapidly washed five times with HBSS/Az using a 12-channel plate washer (Nunc-Immuno Wash 12, Nunc Inc., Naperville, Ill.). The individual wells were then counted in a γ counter. All assays were performed in quadruplicate. In certain assays binding of $^{125}$I-PSGL-1 to immobilized tPS was measured in the presence of increasing concentrations of fluid-phase tPS or tES.

Binding of $^{125}$I-PSGL-1 to Immobilized Anti-Carbohydrate Antibodies. Goat anti-mouse μ-chain specific IgG (50 μl, 5 μg/ml) in HBSS/Az was incubated overnight at 4° C. in Immulon I Removawell® strips. The wells were washed and blocked as described above. Then, either CSLEX-1, LeuM1, or MOPC104E was added (50 μl, 5 μg/ml). After incubation for 1 h at 22° C., the wells were washed three times with HBSS/Az, and $^{125}$I-PSGL-1 in HBSS/Az/0.1% HSA (50 μl, 5,000–10,000 cpm/well) was added. After 1 h the wells were washed as described above, and individual wells were counted in a γ counter. All assays were performed in quadruplicate.

Enyme Digestion of $^{125}$1-PSGL-1. Digestions with sialidase (0.2 U/ml, 15 h), endo-β-galactosidase (2 U/ml, 15 h), and α1,3/4-L-fucosidase (0.32 mU/ml, 15 h) were performed in 0.1 M NaCl, 50 mM sodium acetate, pH 5.5. Digestions with PNGaseF (40 U/ml, 15 h) were done in 0.1 M sodium phosphate, pH 8.6. PSGL-1 was generally not pretreated with SDS because PNGase F had similar effects with or without SDS pretreatment. Sequential digestions with sialidase (0.2 U/ml, 2 h) followed by endo-α-N-acetylgalactosaminidase (0.1 U/ml, 15 h) were performed in 0.1 M NaCl, 50 mM sodium acetate, pH 6.0. All glycosidase digestions were performed at 37° C. in the presence of 20 μM leupeptin, 30 μM antipain, 1 mM benzamidine, and 0.02% NaN$_3$.

Lectin Affinity Chromatography. $^{125}$I-PSGL-1 was applied to a Concanavalin A (Con A) Sepharose column (V$_T$=1 ml) equilibrated in 0.1 M NaCl, 20 mM Tris, pH 7.5, 2 mM CaCl$_2$, 0.1% Brij-58, 0.02% NaN$_3$. The column was washed with five column volumes of equilibration buffer and eluted with 0.5 M α-methylmannoside in equilibration buffer preheated to 65° C. Tomato lectin chromatography was similarly performed except that the column (V$_T$=1 ml) was equilibrated with 0.1 M NaCl, 20 mM MOPS, pH 7.5, 0.1% Brij-58, 0.02% NaN$_3$, and step eluted with 20 mg/ml chitotriose in equilibration buffer. Greater than 85% of the counts loaded on the lectin columns were recovered.

Site Density Determinations. mAbs to P-selectin (G1) or E-selectin (CL2) that inhibit interactions with myeloid cells were used for site density measurements. Wells were coated with tPS or tES (50 μl, 10 μg/ml) and blocked as described above. Saturating concentrations of $^{125}$I-labeled mAb (2 μg/ml) in HBSS/Az/0.1% HSA were added to the wells and incubated for 1 h at 22° C. The wells were washed 5 times and then counted in a γ counter. Specific binding was defined as cpm bound to selectin-coated wells minus cpm bound to HSA-coated wells. Site densities were calculated assuming monovalent binding of antibody at saturation. All assays were performed in quadruplicate.

Neutrophil Adhesion Assay. Human neutrophils were isolated from heparinized blood from consenting volunteer donors by dextran sedimentation, hypotonic lysis, and Ficoll-Hypaque density gradient centrifugation as described by Zimmerman, et al. (1985) *J. Clin. Invest.* 76, 2235–2246. Quantitation of neutrophil adhesion to tPS or tES (50 μl, 10 μg/ml), immobilized on Immulon I Removawell® microtiter plates, was performed as described by Geng, et al., (1990).

Results

An Antiserum to a PSGL-1 Peptide Recognizes the P-selectin Glycoprotein Ligand from Human Areutrophils. To determine whether the polypeptide core of the sialomucin ligand for P-selectin characterized in human neutrophils and HL-60 cells was immunologically related to PSGL-1, a glycoprotein ligand for P-selectin identified by expression cloning from a HL-60 cDNA library, antiserum prepared in rabbits against a peptide corresponding to residues 42–56 of the cDNA-derived amino acid sequence of PSGL-1, was tested to see if this antiserum could recognize the glycoprotein ligand that we isolated by P-selectin affinity chromatography. The radiochemical purity of the $^{125}$I-P-selectin glycoprotein ligand used in this study showed that it exhibited a relative molecular mass of approximately 250,000 under nonreducing conditions and approximately 120,000 under reducing conditions. Thus, the radioiodinated glycoprotein contained two disulfide-linked subunits of M$_r$ 120,000, consistent with previous results using protein blotting or metabolic labeling. As noted previously, a small portion of the dimeric glycoprotein was resistant to reduction under the conditions used. The immune serum, but not normal rabbit serum, precipitated the purified $^{125}$I-P-selectin ligand. Precipitation by the antiserum was specific for the 42–56 peptide sequence, because it was completely inhibited by inclusion of this peptide, but not by a control peptide corresponding to amino acids 354–376 of PSGL-1. The specificity of the antiserum was further demonstrated by its selective immunoprecipitation of the ligand from a crude mixture of radiolabeled neutrophil membrane proteins that were eluted from a WGA column.

Two tryptic peptides were derived from the P-selectin glycoprotein ligand purified from human neutrophils. The sequences of these peptides, His-Met-Tyr-Pro-Val-Arg and Pro-Gly-Lys-Thr-Pro-Glu-Pro, are identical to amino acids 340–345 and 380–386 in the cDNA-derived sequence of PSGL-1 (Sequence ID No. 1). These data and the results from the immunoprecipitation experiments establish the identity of the polypeptide backbones of the P-selectin ligands studied by both groups.

Purified $^{125}$I-PSGL-1 Binds Specifically to P-selectin. $^{125}$I-PSGL-1 isolated from human neutrophils bound in a time-dependent fashion to tPS immobilized on microtiter wells. Binding increased as a function of the amount of tPS coated on the wells. Binding was $Ca^{2+}$-dependent and was abolished by G1, a 'nAb to P-selectin that inhibits leukocyte adhesion to P-selectin, but not by S12, a mAb that does not block adhesion. In addition, 84.6±2.4% (mean±SD, n=4) of the radiolabeled glycoprotein rebound to a column of recombinant, soluble P-selectin (tPS) and was eluted with buffer containing EDTA. This result demonstrates that the function of $^{125}$I-PSGL-1 was not substantially altered by iodination.

PSGL-1 Contains Substituted Poly-N-acetyllactosamine. PSGL-1 from human myeloid cells contains clustered, sialylated O-linked oligosaccharides that are released from the polypeptide backbone by β-elimination (Norgard, et al. 1993). To determine whether these O-linked glycans had simple structures, $^{125}$I-PSGL-1 was treated with sialidase, then with endo-α-N-acetylgalactosaminidase, an enzyme that releases non-sialylated Galβ1-3GalNAc core 1 disaccharides, but not more complex O-linked glycans, from serine or threonine residues (Umemoto, et al., (1977) J. Biol. Chem. 252, 8609–8614). Treatment with sialidase slowed the electrophoretic mobility of PSGL-1, confirming previous results. Subsequent addition of endo-β-N-acetylgalactosaminidase increased the mobility of PSGL-1 only slightly more than sialidase-treated PSGL-1, suggesting that very few of the O-linked oligosaccharides were simple structures that were susceptible to this enzyme.

PSGL-1 is fucosylated, because it contains the sialylated, fucosylated tetrasaccharide antigen, sLe$^x$ (Norgard, et al., (1993)). Treatment of the glycoprotein with α1,3/4 fucosidase, which removes fucose attached to a penultimate GlcNAc, had no effect on electrophoretic mobility, although it did remove fucose residues that were part of the Le$^x$ epitopes on the molecule. The ligand was then treated with endo-β-galactosidase, which hydrolyzes internal β1-4 linkages between galactose and N-acetylglucosamine (Galβ1-4GlcNAc) in extended unbranched poly-N-acetyllactosamine chains (Scudder, et al., (1983) Biochem. J. 213, 485–494; Scudder, et al., (1984) J. Biol. Chem. 259, 6586–6592). This enzyme slightly accelerated the mobility and lessened the electrophoretic heterogeneity of PSGL-1, suggesting that PSGL-1 contained some poly-N-acetyllactosamine.

To confirm the presence of poly-N-acetyllactosamine on PSGL-1, the ability of $^{125}$I-PSGL-1 to bind to a column containing immobilized tomato lectin, which avidly binds to poly-N-acetyllactosamine, was tested. A single poly-N-acetyllactosamine chain is sufficient to confer binding of a glycoprotein to tomato lectin in this system (Merkle, et al. (1987) J. Biol. Chem. 262, 8179–8189). Greater than 95% of the PSGL-1 bound to the column, indicating that essentially every molecule contained at least one poly-N-acetyllactosamine (Table 3). Treatment of PSGL-1 with endo-β-galactosidase modestly reduced to 84% the amount of material binding to the column. This suggests that most, if not all, of the poly-N-acetyllactosamine could be removed from a portion of the PSGL-1 molecules by endo-β-galactosidase. Because substitutions of poly-N-acetyllactosamine with sialic acid and/or fucose inhibit the efficiency of this enzyme, PSGL-1 was pretreated with sialidase and fucosidase before addition of endo-β-galactosidase. Treatment with sialidase and fucosidase had no effect on binding of PSGL-1 to the column, consistent with the fact that substitutions with sialic acid or fucose do not affect binding of poly-N-acetyllactosamine to tomato lectin. However, subsequent addition of endo-β-galactosidase reduced to 69% the portion of the glycoprotein binding to the column. Because tomato lectin binds weakly to terminal GlcNAc residues that are exposed by endo-β-galactosidase treatment (Cummings, (1994) Methods Enzymol. 230, 66–86), β-N-acetylglucosaminidase was added to remove these terminal residues. Only 53% of this material bound to tomato lectin. These data clearly demonstrated that PSGL-1 contained poly-N-acetyllactosamine. Furthermore, at least some of these chains were resistant to endo-β-galactosidase because of substitutions with sialic acid and/or fucose. The inability of sialidase, fucosidase, endo-β-galactosidase, and β-N-acetylglucosaminidase to eliminate binding of all PSGL-1 molecules to tomato lectin may reflect enzyme resistance because of the clustered nature of O-linked glycans, the presence of internal fucose residues, and/or the presence of additional substitutions such as sulfate on the poly-N-acetyllactosamine.

TABLE 3

Effects of Glycosidases on Binding of $^{125}$I-PSGL-1 to a Tomato Lectin Affinity Column

| Enzyme Treatment | Percentage Bound |
| --- | --- |
| Sham | >95 |
| Endo-β-galactosidase | 84 |
| Sialidase + Fucosidase | >95 |
| Sialidase + Fucosidase + Endo-β-galactosidase | 69 |
| Sialidase + Fucosidase + Endo-β-galactosidase + β-N-acetylglucosaminidase | 53 |
| Peptide:N-glycosidase F | >95 |

$^{125}$I-PSGL-1 was treated with the indicated glycosidase(s) and applied to a column of immobilized Tomato lectin (VT = 1 ml, 2 mg lectin/ml resin). After washing, the column was eluted with 20 mg/ml of chitotriose. The percentage of PSGL-1 bound was defined as the radioactivity eluted by chitotriose divided by the sum of the radioactivity in the column flowthrough, wash, and eluate.

PSGL-1 Contains a Limited Number of Heterogeneous N-linked Oligosaccharides. PNGaseF treatment slightly increased the electrophoretic mobility of [$^{125}$I]PSGL-1, consistent with previous studies indicating that all molecules contained a limited number of N-linked glycans sensitive to this enzyme. The cDNA-derived sequence of PSGL-1 indicates that the molecule contains only three potential sites for attachment of N-linked oligosaccharides (Sako, et al., (1993)). To explore possible heterogeneity of the N-linked structures, sham-treated and PNGaseF-treated [$^{125}$I]PSGL-1 was applied to a column of Concanavalin A (Con A), a plant lectin that binds avidly to high mannose N-linked glycans, less avidly to complex biantennary and hybrid N-linked oligosaccharides, and very weakly to complex triantennary and tetraantennary N-linked chains (Ogata, et al. (1975) *J. Biochem.* (Tokyo) 78, 687–696). 41.9±4.2% of the sham-treated ligand bound to Con A, whereas only 3.7±1.0% of the PNGaseF-treated material bound (mean±SD, n=4). Greater than 85% of the counts loaded on the column were recovered. This result demonstrated that PNGaseF removed N-linked glycans recognized by Con A from PSGL-1.

The fraction of PSGL-1 not bound by Con A migrated slightly slower than the fraction bound by Con A. To confirm that the Con A-unbound material also contained N-linked oligosaccharides, both the bound and unbound fractions were treated with PNGaseF. The enzyme decreased the apparent molecular weights of the Con A-unbound and Con A-bound fractions by 14.5 kDa and 13.7 kDa, respectively. Thus, both fractions had PNGaseF-sensitive N-linked glycans. These data suggested that the Con A-unbound fraction contained triantennary and/or tetraantennary N-linked glycans that Con A did not recognize. The largest N-linked glycan to be described on myeloid cells (molecular mass approximately 6,600) is a disialylated tetraantennary structure with poly-N-acetyllactosamine sequences on each antenna and both external and core fucose (Spooncer, et al. (1984) *J. Biol. Chem.* 259, 4792–4801). Therefore, the observed change in electrophoretic mobility after PNGaseF treatment is consistent with the removal of at least two and possibly three complex N-linked glycans. Even after PNGaseF treatment, the Con A-unbound material migrated slightly slower than the Con A-bound material. This may indicate that the Con A-unbound fraction retained a single N-linked chain that was resistant to PNGaseF. Alternatively, there may be other structural differences between the Con-A-bound and Con-unbound fractions, of which the most likely is heterogeneity in O-linked glycosylation.

Treatment with sialidase or endo-β-galactosidase had similar effects on the electrophoretic mobilities of the Con A-unbound and Con A-bound fractions, probably because these enzymes primarily affected the abundant O-linked oligosaccharides. Endo-β-galactosidase produced similar increases in the electrophoretic mobilities of PSGL-1 pretreated with PNGaseF and PSGL-1 that contained all its N-linked oligosaccharides, suggesting that at least some of the poly-N-acetyllactosamine was on the O-linked glycans.

PSGL-1 Expresses Le$^x$ and sLe$^x$ on O-linked Poly-N-acetyllactosamine. To determine whether PSGL-1 expresses Le$^x$ or sLe$^x$ on poly-N-acetyllactosamine, an assay was developed to measure the binding of $^{125}$I-PSGL-1 to an immobilized monoclonal IgM antibody to sLe$^x$ (CSLEX-1) or Le$^x$ (LeuM1), or to an immobilized irrelevant IgM mAb (MOPC104E). PSGL-1 bound to CSLEX1 but not to MOPC104E, confirming previous immunoblotting data that the glycoprotein expressed sLe$^x$. Greater than 85% of the $^{125}$I-PSGL-1 molecules bound to a CSLEX-1 affinity column, indicating that virtually all molecules contained sLe$^x$. PSGL-1 also bound to LeuM1, indicating that it contained Le$^x$, although it is possible that desialylation generated this structure during purification of the glycoprotein. Treatment of PSGL-1 with sialidase eliminated binding to CSLEX-1 and increased binding to LeuM1, consistent with the known specificities of these antibodies. Treatment of PSGL-1 with fucosidase had no effect on binding to CSLEX-1, in keeping with the inhibition of this enzyme by terminal sialic acid (Sano, et al., (1992) *J. Biol. Chem.* 267, 1522–1527; Maemura, K. and Fukuda, M. (1992) *J. Biol. Chem.* 267, 24379–24386). In contrast, the fucosidase eliminated the binding of PSGL-1 to LeuM1.

After establishing the specificity of the assay, it was determined whether treatment of PSGL-1 with endo-β-galactosidase affected the expression of Le$^x$ or sLe$^x$. This enzyme abolished binding of PSGL-1 to immobilized LeuM1 and decreased binding to CSLEX-1 by 64±14% (mean±SD, n=4). These data clearly indicated that poly-N-acetyllactosamine cleaved by endo-β-galactosidase carried some, and perhaps all, of the Le$^x$ as well as a portion of the sLe$^x$ on PSGL-1. The remaining sLe$^x$ structures may be on branched or substituted poly-N-acetyllactosamine that was resistant to the enzyme or on chains that lacked poly-N-acetyllactosamine.

In contrast to the effects of endo-β-galactosidase, PNGaseF did not affect binding of PSGL-1 to immobilized LeuM1 or CSLEX-1, indicating that few, if any, Le$^x$ or sLe$^x$ structures were present on PNGaseF sensitive N-linked oligosaccharides. In conjunction with the other data, this observation indicated that O-linked oligosaccharides carried most, and perhaps all, of the Le$^x$ and sLe$^x$ structures. Furthermore, at least some of these structures were on O-linked poly-N-acetyllactosamine.

Effects of Glycosidases on Binding of PSGL-1 to P-selectin. The effects of the glycosidases on binding of $^{125}$I-PSGL-1 to immobilized tPS were then determined. Treatment with sialidase, which eliminated binding to the anti-sLe$^x$ antibody but enhanced binding to the anti-Le$^x$ antibody, completely prevented binding of PSGL-1 to tPS. In contrast, treatment with fucosidase, which eliminated binding to the anti-Le$^x$ antibody but not to the anti-sLe$^x$ antibody, had no effect on the interaction of PSGL-1 with tPS. These data are consistent with previous results from other assays that high-affinity binding of P-selectin to myeloid cells or to PSGL-1 required sialic acid on the ligand.

Treatment of PSGL-1 with endo-β-galactosidase resulted in only a modest reduction in binding to immobilized tPS. In four independent experiments, endo-β-galactosidase reduced binding by 25±11% (mean±SD, n=4). These data suggested that some, but not all, of the sialylated chains required for P-selectin recognition were on poly-N-acetyllactosamine that were sensitive to the enzyme. The remaining glycans required for recognition might be on poly-N-acetyllactosamine that were resistant to endo-β-galactosidase or on oligosaccharides that lacked poly-N-acetyllactosamine. Endo-β-galactosidase inhibited binding of PSGL-1 to the anti-sLe$^x$ antibody more than it inhibited binding to tPS. The levels of sLe$^x$ with the interaction with tPS could not be accurately correlated, since it is not known how many sLe$^x$ structures were required for PSGL-1 to bind to either the antibody or to tPS in these assays.

Treatment of PSGL-1 with PNGaseF did not affect its ability to bind to tPS, supporting the conclusion that N-linked oligosaccharide played little if any role in P-selectin recognition.

The structure and function of PSGL-1 from human neutrophils was further characterized using assays with the purified, radioiodinated glycoprotein. The results suggest that this molecule presents an array of sialylated and fucosylated, O-linked poly-N-acetyllactosamine that creates high-affinity binding structures for P-selectin.

Although the great majority of the oligosaccharides on PSGL-1 are O-linked, there are a few N-linked glycans which were determined to be heterogeneous. All PSGL-1 molecules contained PNGaseF-sensitive N-linked oligosaccharides, but only 42% of the glycoprotein molecules bound to Con A, a lectin that binds well to high mannose N-linked glycans and less well to complex biantennary and hybrid N-linked chains. Based on the reductions in apparent molecular weight observed in SDS gels, PNGaseF removed at least two of the three possible N-linked glycans from both the Con A-bound and Con A-bound fractions of PSGL-1. One chain on the Con A-unbound fraction of PSGL-1 may be resistant to PNGaseF, since the Con A-unbound material still migrated slightly slower in SDS gels than the Con A-bound material following treatment with PNGaseF. Alternatively, PNGaseF may have removed all the N-linked chains from both the Con A-bound and Con A-unbound fractions, in which case the mobility difference may reflect heterogeneous O-linked glycosylation. The PNGaseF-sensitive N-linked glycans carried little or no $Le^x$ and $sLe^x$ and did not contribute measurably to the binding interaction with P-selectin. These results strongly suggest that the O-linked glycans display the relevant structures that P-selectin recognizes. It is highly improbable that a single PNGaseF-resistant N-linked glycan on a subpopulation of PSGL-1 is responsible for P-selectin recognition.

Because at least some of the O-linked oligosaccharides on PSGL-1 carry ($\beta$2-3)sialic acid and ($\alpha$1-3)fucose, they must have relatively large, branched structures. In agreement with this prediction, PSGL-1 was found to carry few of the Ser/Thr-linked Gal$\beta$1-3GalNAc core 1 disaccharides that endo-$\alpha$-N-acetylgalactosaminidase cleaves following removal of terminal sialic acids. These data are consistent with previous observations that less than 10% of the $^3$H-labeled O-linked oligosaccharides released by $\beta$-elimination from PSGL-1 were small as assessed by gel filtration.

The O-linked glycans on PSGL-1 include a heterogeneous group of poly-N-acetyllactosamine. As measured by mobility on SDS gels and by binding to tomato lectin, endo-$\beta$-galactosidase cleaved some of the poly-N-acetyllactosamine at the internal $\beta$1-4 linkage between the Gal and GlcNAc. Treatment with this enzyme also reduced the amount of $Le^x$ and $sLe^x$, indicating that some of these structures were on poly-N-acetyllactosamine. As measured by binding to tomato lectin, endo-$\beta$-galactosidase cleaved other poly-N-acetyllactosamine only after treatment with sialidase and fucosidase, demonstrating that they had sialic acid and fucose moieties at or near their terminus that prevented access to endo-$\beta$-galactosidase. Because a significant portion of the PSGL-1 molecules still bound to tomato lectin after treatment with all three enzymes, there may be other O-linked poly-N-acetyllactosamine chains that remained resistant to endo-$\beta$-galactosidase because of branching or additional internal substitutions. Such structures might be responsible, at least in part, for the ability of PSGL-1 to bind to immobilized tPS after digestion with endo-$\beta$-galactosidase.

Previous studies have shown that human myeloid cells express poly-N-acetyllactosamine on some O-linked glycans. These structures occur almost exclusively on the branch attached to the C-6 of GalNAc as part of a core 2 O-linked oligosaccharide (Fukuda, et al., (1986) *J. Biol. Chem.* 261, 12796–12806; Hanisch, et al., (1989) *J. Biol. Chem.* 264, 872–883). Of the approximately 80 O-linked glycans on the major sialomucin of human myeloid cells, leukosialin (CD43), only one or two contain poly-N-acetyllactosamine, and approximately half of these have a terminal $sLe^x$ moiety. In contrast, PSGL-1 from neutrophils appears to contain a higher percentage of core 2, poly-N-acetyllactosamine. Direct structural analysis will be required to determine the specific monosaccharides, linkages, and modifications that constitute the O-linked glycans of PSGL-1. However, the current data suggest that some of these glycans may differ from those in leukosialin, implying that human myeloid cells can differentially glycosylate the polypeptide backbones of two distinct sialomucins. This differential glycosylation is functionally important, because P-selectin binds with high affinity to PSGL-1, but not to leukosialin.

The selectins require sialylation and fucosylation of most carbohydrate ligands for recognition. Similarly, PSGL-1 requires sialic acid and fucose to interact with P-selectin. Although PSGL-1 expresses the terminal $sLe^x$ tetrasaccharide, it is not clear whether it requires this structure per se for recognition. A simple model is that PSGL-1 presents many terminal $sLe^x$ moieties that increase the avidity with which it interacts with P-selectin. However, previous observations indicate that high concentrations of cell surface $sLe^x$ are not sufficient to confer optimal interactions with P-selectin. It is more likely that additional modifications on each oligosaccharide chain are essential for optimal recognition. Specific features of several oligosaccharides in proximity may also present a clustered saccharide patch that promotes high affinity binding to P-selectin.

Sako et al. (1993) generated a recombinant form of PSGL-1 that bound to P-selectin when expressed in COS cells co-transfected with an $\alpha$1-3/4 fucosyltransferase (FTIII), but not in COS cells lacking the fucosyltransferase. The relative molecular mass of the recombinant molecule was similar to that of PSGL-1 in human myeloid HL-60 cells, and the authors apparently concluded that the structure and function of recombinant PSGL-1 were equivalent to those of the native molecule. However, the specific oligosaccharide structures attached to native PSGL-1 and the glycosyltransferases required to construct these structures are unknown. Moreover, the $\alpha$1-3/4 fucosyltransferase (FTIII) expressed in the COS cells to generate recombinant PSGL-1 differs from the fucosyltransferases in human myeloid cells (Goelz, et al. (1990) *Cell* 63, 1349–1356; Sasaki, et al. (1994) *J. Biol. Chem.* 269, 14730–14737). Thus, it is not clear that the glycosylation, and hence the function, of recombinant PSGL-1 is identical to that of the native glycoprotein in human myeloid cells. Indeed, following sialidase digestion of recombinant PSGL-1, addition of endo-$\alpha$-N-galactosaminidase caused a substantial increase in mobility of the glycoprotein, indicating that recombinant PSGL-1 expressed in COS cells with FTIII, in contrast to the native glycoprotein, contains many simple O-linked core 1 Gal$\beta$1-3GalNAc disaccharides that are susceptible to this enzyme.

Sako et al. found that recombinant PSGL-1 no longer bound to P-selectin after treatment with sialidase and endo-$\beta$-N-galactosaminidase, and concluded that O-linked oligosaccharides were important for recognition by P-selectin. Based on the data presented here, this conclusion appears to be correct. However, the experiment of Sako et al. cannot be used to support a role for O-linked glycans in recognition. Prolonged digestion with sialidase is required to eliminate binding to native PSGL-1, and the conditions for sialidase digestion of recombinant PSGL-1 used by Sako et al. reduced, but did not eliminate, binding of P-selectin. The loss of P-selectin binding after addition of endo-$\alpha$-N-galactosaminidase, which releases only non-sialylated core 1 Gal$\beta$1-3GalNAc disaccharides, was more likely due to the previously observed contamination of this enzyme with sialidase, which would remove the remaining sialic acids required for recognition.

Sako et al. also suggested that the N-linked oligosaccharides contributed to binding to P-selectin, because recombinant P-selectin did not reprecipitate all of the PNGaseF-treated recombinant PSGL-1. However, these authors did not demonstrate whether the reprecipitation assay was quantitative by testing whether additional precipitation steps increased recovery of PSGL1. The same group also concluded that N-linked glycosylation was important for P-selectin recognition because they observed that myeloid HL-60 cells treated with tunicamycin, an inhibitor of N-linked glycosylation, did not adhere to P-selectin-expressing cells (Larsen, et al., (1992) *J. Biol. Chem.* 267, 11104–11110). However, tunicamycin exerts indirect effects on cells, such as inhibiting the exit of some proteins from the endoplasmic reticulum, that make it difficult to interpret its effects on cell adhesion. The studies in this application provide no evidence that the N-linked glycans of PSGL-1 from human neutrophils play a role in recognition by P-selectin.

EXAMPLE 2

Expression of PSGL-1 in CHO Cells Transfected with cDNA Encoding Fucosyltransferase III and a core 2 β1-6-N-acetylglucosaminyltransferase.

A functional, recombinant form of PSGL-1 that has many of the properties of native PSGL-1 purified from human neutrophils has been expressed. The study demonstrates that PSGL-1, in order to bind P-selectin, requires sialylated and fucosylated O-linked oligosaccharides containing the branched core 2 structure.

PSGL-1 was expressed in Chinese hamster ovary (CHO) cells, which were selected because the N- and O-linked oligosaccharide structures on these cells are very well characterized. In particular, the Ser/Thr-linked oligosaccharides on secreted and surface glycoproteins are simple, core 1, mono- and disialylated derivatives of Galβ1-3GalNAcα1-Ser/Thr (Sasaki et al., *J. Biol. Chem.* 262:12059–12076, 1987; Seguchi et al., *Arch. Biochem. Biophys.* 284: 245–256, 1991). DHFR-minus CHO cells were stably transfected with the cDNA encoding fucosyltransferase III (FTIII) (Kukowska-Latallo, et al., 1990), with the cDNA encoding the core 2 β1-6-N-acetylglucosaminyltransferase (Bierhuizen and Fukuda, *Proc. Natl. Acad. Sci. USA* 89:9326–933), 1992; Bierhuizen et al., *J. Biol. Chem.* 269:4473–4479, 1994), or with both cDNAs. The cDNAs were ligated into the pRc/RSV or pCDNA3 expression vectors (Invitrogen). Following transfection with the calcium phosphate precipitation method, stably transfected clones were selected in medium containing G418. Stable clones expressing either or both glycosyltransferases were identified using specific glycosyltransferase assays performed on cell lysates. Cells expressing FTIII also expressed high levels of the sialyl Lewis x antigen (NeuAcα2-3Galβ1-4[Fucα1-3]GlcNAcβ1-4-R) on their surfaces, as measured by binding of the CSLEX1 monoclonal antibody (Fukushiina et al., *Cancer Res.* 44:5279–5285, 1984).

A cDNA encoding a full-length form of PSGL-1 (Moore et al., *J. Cell Biol.* 128: 661–671, 1995) was inserted into the pZeoSV expression vector (Invitrogen). CHO cells expressing the glycosyltransferases were transfected with the PSGL-1 cDNA using the Lipofectamine reagent (Gibco BRL Life Technologies). In transient expression analysis, cells were analyzed by flow cytometry 48 h after transfection. Stable clones were selected in medium containing both G418 and Zeocin (Invitrogen). Analysis of cell-bound antibodies by flow cytometry was performed as described in Moore et al, (1995). Analysis of cell-bound platelet-derived P-selectin by flow cytometry was performed as described by Moore and Thompson, *Biochem. Biophys. Res. Commun.* 186:173–181 (1992).

In transient expression studies, PSGL-1 was co-expressed on the majority of transfected cells expressing FTIII, the core 2 β1-6-N-acetylglucosaminyltransferase, or both glycosyltransferases. Co-expression was documented by strong binding of anti-PSGL-1 monoclonal antibodies PL1 or PL2 (Moore, et al. 1995) as measured by flow cytometry. In contrast, flow cytometric analysis indicated that P-selectin bound only to CHO cells expressing FTIII, the core 2 β1-6-N-acetylglucosaminyltransferase and PSGL-1. P-selectin did not bind to CHO cells expressing either or both glycosyltransferases, in the absence of PSGL-1. P-selectin also failed to bind to CHO cells expressing either FTIII or the core 2 β1-6-N-acetylglucosaminyltransferase, even in the presence of PSGL-1. Thus, a functional form of PSGL-1 capable of binding P-selectin was expressed only on CHO cells that also expressed FTIII and the core 2 β1-6-N-acetylglucosaminyltransferase.

CHO cell clones were also selected that stably expressed FTIII and the core 2 β1-6-N-acetylglucosaminyltransferase. These cells expressed high levels of PSGL-1 as detected by binding of PLI and PL2 by flow cytometry. P-selectin also bound well to these stably selected cells. Thus, high affinity binding of P-selectin to CHO cells required the simultaneous expression of FTIII, the core 2 β1-6-N-acetylglucosaminyltransferase, and PSGL-1 by the cells. For cells expressing PSGL-1 either transiently or stably, binding of P-selectin was specific, as it was blocked by an inhibitory monoclonal antibody to P-selectin, G1, but not by a noninhibitory monoclonal antibody to P-selectin, S12 (Geng et al., *Nature* 343:757–760, 1990). Binding was also $Ca^{2+}$-dependent, consistent with the requirement for $Ca^{2+}$ for selectins to bind carbohydrate ligands. P-selectin also bound specifically to PSGL-1 on the cells: PL1, but not PL2, completely blocked binding of P-selectin. Furthermore, the anti-42–56 serum, discussed below, but not control rabbit serum, blocked binding of P-selectin.

These data indicate that CHO cells can be genetically engineered to express a recombinant form of PSGL-1 that binds specifically and with high affinity to P-selectin as does native PSGL-1 from human leukocytes. The inhibition of P-selectin binding by PL1 and by the anti-42–56 serum indicates that P-selectin binds to the same region on recombinant PSGL-1 and on native PSGL-1 from human leukocytes. The requirement for the core 2 enzyme in the CHO cells indicates that a critical component of the P-selectin recognition site on PSGL-1 consists of branched, core 2 O-linked oligosaccharide(s) with a Galβ1-3(Galβ1-4GlcNAcβ1-6)GalNAc-Ser/Thr backbone. Sialylation and fucosylation of PSGL-1 is also required for high affinity binding to P-selectin; these modifications must occur on the critical core 2 O-linked glycans.

EXAMPLE 3

Determination of a Sulfated Tyrosine Containing Region in PSGL-1 Critical for P-selectin Binding.

PSGL-1 has an extracellular domain of 308 residues. The first 18 residues constitute a signal peptide. Residues 19–41 constitute a putative propeptide that is predicted to be cleaved following synthesis, probably in the trans-Golgi network. Therefore, the putative N-terminus of the mature protein begins at residue 42. The three tyrosines within the consensus sequence for tyrosine sulfation are at residues 46, 48, and 51, near the N-terminus. A rabbit polyclonal antiserum to a synthetic residue encoding residues 42–56 completely blocks binding of PSGL-1 to P-selectin, suggesting that a least part of the critical recognition site for P-selectin lies in this region. All references to residue number refer to Sequence Listing ID No. 1.

Two IgG monoclonal antibodies to PSGL-1, termed PL1 and PL2, were previously described in Moore et al, *J Cell Biol.* 128:661–671 (1995)). PL1, but not PL2, completely blocks binding of PSGL-1 to P-selectin, and abolishes adhesion of leukocytes to P-selectin under both static and shear conditions. To map the regions on PSGL-1 where the epitopes for PL1 and PL2 are located, a series of fusion proteins containing overlapping regions of the extracellular domain of PSGL-1 were expressed in bacteria. The PSGL-1 sequences in the fusion proteins were as follows: Fragment 1, residues 18–78; Fragment 2, residues 63–123; Fragment 3, residues 109–168; Fragment 4, residues 154–200; Fragment 5, residues 188–258; and Fragment 6, residues 243–308. The DNA encoding each fragment was fused in frame to the DNA encoding dihydrofolate reductase and a 6X His tag, in the expression vector pQE-40 (Qiagen). Each fragment was expressed in bacteria and purified on a nickel affinity column which bound to the 6X His tag. The reactivity of each fusion protein with the antibodies was assessed by Western blotting under reducing conditions.

PL1 bound strongly to Fragment 1, but not to any of the other fragments. This indicates that the PLI epitope is located within residues 18–78. Assuming proteolytic removal of the propeptide from native mature PSGL-1, the epitope is located within residues 42–78. Since PL1 does not bind Fragment 2 (residues 63–123), the epitope is likely located within residues 42–70. Thus, PL1 binds to an N-terminal epitope that is near the epitopes for the polyclonal anti-42–56 serum. This result further suggests that a critical component of the P-selectin recognition site resides within a small region at the N-terminus of PSGL-1. In contrast, the nonblocking monoclonal antibody PL2 bound to Fragments 5 and 6 (but not the other fragments), suggesting that it recognizes an epitope within residues 243–258, which are present in both fragments.

These results demonstrate that P-selectin binds to a specific region on both native and recombinant PSGL-1. This region resides near the N-terminus of the mature molecule. High affinity binding of PSGL-1 to P-selectin requires both tyrosine sulfation and sialylated, fucosylated, core 2 branched O-linked oligosaccharides. Fragments of PSGL-1, or derivatives thereof, can be constructed that contain the binding site for P-selectin. Such fragments may be as short as that encoding residues 42–58; this fragment contains the three tyrosines that are capable of being sulfated as well as two threonines that may be attachment sites for core 2, O-linked oligosaccharides. Longer fragments extending from residue 42 should also bind with high affinity to P-selectin.

Experimental Procedures

Chemicals and reagents. Carrier Free [$^{35}$S]sulfate (1100–1600 Ci/mmol) was purchased from Dupont/NEN (Wilmington, De.). Emphaze® affiity support resin was purchased from Pierce Biochemicals (Rockford, Ill.). *Aerobacter aerogenes* arylsulfatase, *Arthrobacter ureafaciens* neuraminidase, and sulfated monosaccharides were obtained from Sigma Chemical Co. (St. Louis, Mo.). Recombinant peptide:N-glycosidase F was purchased from Boehringer Mannheim (Indianapolis, Ind.). All cell culture reagents were obtained from GIBCO/BRL (Grand Island, N.Y.). Authentic tyrosine sulfate standard was synthesized as described (Huttner, (1984) *Meth. Enzymol.* 107, 200–224) using concentrated $H_2SO_4$ and tyrosine. Other chemicals were ACS grade or better and were obtained from Fisher Scientific.

Isolation of radiolabeled PSGL-1. PSGL-1 was purified from human neutrophils and radiolabeled with Na$^{125}$I as described by Moore, et al., (1994). HL-60 cells (1–2×10$^6$ cells/ml) were labeled for 48 h with 100 μCi/ml [$^{35}$]sulfate at 37° C. in sulfate-deficient medium (S-MEM) containing 10% dialyzed fetal bovine serum. $^{35}$S-PSGL-1 was purified using affinity chromatography in a column containing recombinant soluble P-selectin (Ushiyama, et al., (1993) *J. Biol. Chem.* 268, 15229–15237) coupled to Emphaze® at a density of 5 mg/ml (Moore, et al. (1994)). The enriched EDTA-eluted sample was rechromatographed on the P-selectin column after dialysis into $Ca^{2+}$-containing buffer. Purified $^{35}$S-PSGL-1 was treated with reducing or nonreducing SDS sample buffer and electrophoresed in a 7.5% polyacrylamide gel (Laemmli (1970)). Gels were dried and then exposed to Fuji RX x-ray film at −80° C.

Detection of tyrosine sulfate. Tyrosine sulfation of PSGL-1 was determined by base hydrolysis of $^{35}$S-PSGL-1. Following identification of $^{35}$S-PSGL-1 by autoradiography, the dried gel was aligned with the exposed x-ray film and the band from the nonreducing lane was subjected to strong base hydrolysis in 1.0 M NaOH at 110° C., for 24 h as described (Hortin, et al., *J. Biol. Chem.* 261, 15827–15830 (1986). The hydrolysate was passed over. a Dowex 50 (H$^+$) column washed with water, lyophilized, and analyzed by anion exchange chromatography using a Varian AX-5 column (4 mm×30 cm) that was eluted with a gradient of $NaH_2PO_4$, pH 3.0.

Enzymatic treatment of PSGL-1. All arylsulfatase digestions were performed with *Aerobacter aerogenes* arylsulfatase (EC 3.1.6.1) (Fowler and Rammler (1964) *Biochemistry* 3, 230–237) in approximately 500 μl of 0.01 M Tris-HCl, pH 7.5, overnight at 37° C. Following digestion, the enzyme reactions were terminated by boiling for 15 in. Sham digestions were performed with 1000 mU of boiled enzyme. $^{35}$S-tyrosine sulfate from $^{35}$S-PSGL-1 was prepared by base hydrolysis as described above. The base hydrolysate was treated with 50 mU or 1000 mU of active arylsulfatase, or with 1000 mU of boiled arylsulfatase, then analyzed by anion exchange chromatography.

The specificity of the *A. aerogenes* arylsulfatase was determined for the sulfated monosaccharides GlcNAc-6-sulfate, Gal-6-sulfate, GalNAc-6-sulfate, and GalNAc-4-sulfate. Each of the sulfated monosaccharides (100 mmol) was separately treated with 1000 mU of boiled or active enzyme. After overnight incubation, the reaction mixtures were boiled for 15 min, lyophilized, resuspended in water and analyzed by high pH anion exchange chromatography with a Dionex CarboPac PA-1 column and PAD detection as described (Shilatifard and Cummings (1995) *Glycobiology* 5, 291–297.

Intact $^{35}$S-PSGL-1 or $^{125}$I-PSGL-1 was treated with *A. aerogenes* arylsulfatase as described above. The [$^{35}$S]sulfate released from $^{35}$S-PSGL-1 by arylsulfatase was quantified by $BaSO_4$ precipitation, in which 100 μl saturated $Na_2SO_3$ as a carrier (Shilatifard, et al., (1993) *J. Virol.* 67, 943–945). In the graphic representation of the data, the sulfate released from the sham-treated sample was adjusted setting the sham-treated sample equal to 0%. The actual percentage of radioactivity released from the sham-treated samples ranged from 1.3–5.0%.

In a control experiment, $^{125}$-PSGL-1 was treated with 1000 mU of *Arthrobacter ureafaciens* neuraminidase in 0.05

M sodium acetate, pH 5.0 overnight at 37° C. prior to application to a CSLEX-1 antibody column. Chromatography on CSLEX-1 was performed as described previously (Moore, et al, 1994).

$^{35}$S-PSGL-1 was treated with peptide:N-glycosidase F as described Shilatifard, et al., (1993). $^{35}$S-PSGL-1 was denatured by boiling 5 min in 50 µl of 50 mM sodium phosphate, pH 7.5, 50 mM 2-mercaptoethanol, 0.5% SDS. The SDS was then diluted to a fmal concentration of 0.2% with 1.5% NP40. 10 U of enzyme was added to the denatured $^{35}$S-PSGL-1 and incubated overnight at 37° C.

Rebinding of Arylsulfatase-treated PSGL-1 to P-selectin.

Arylsulfatase-treated PSGL-1 was applied to a P-selectin affinity column in $Ca^{2+}$-containing buffer, and the bound radioactivity was eluted with EDTA. The percentage of $^{125}$I-PSGL-1 eluted from the column with EDTA was corrected setting the sham-treated sample equal to 100% (actual rebinding ranged from 87–99%).

Immunoprecipitation and P-selectin Binding Assays.

Immunoprecipitation of $^{35}$S-PSGL-1 was performed as described by Moore, et al., (1994), using a rabbit antiserum (Moore, et al., (1995), Moore, et al., 1994)) to a peptide corresponding to residues 42–56 (QATEYEYLDYDFLPE) of PSGL-1 (Sako, et al., (1993)) (anti-42–56) or normal rabbit serum (NRS). The immunoprecipitates were analyzed by SDS-PAGE under nonreducing conditions, followed by autoradiography. The solid phase P-selectin binding assay was performed as described by Moore, et al., 1994). Briefly, $^{125}$I-PSGL-1 was incubated in the presence of NRS or the antiserum directed against residues 42–56 of PSGL-1 (anti-42–56) in microtiter plates containing immobilized recombinant soluble P-selectin (50 µl, 10 µg/ml) or human serum albumin (HSA) (50 µl, 1% HSA). Binding of platelet-derived P-selectin to HL-60 cells was measured by flow cytometry as described in the presence of 20% NRS or 20% anti-42–56 serum.

Results and Discussion

To determine if PSGL-1 is post-translationally sulfated, human promyelocytic leukemia HL-60 cells were metabolically-labeled with [$^{35}$S]sulfate, and PSGL-1 was purified from lysates of these cells by affinity chromatography on a P-selectin column. An [$^{35}$S]sulfate-labeled protein was detected that migrated in SDS gels with a relative molecular mass of 120,000 under reducing conditions and 240,000 under nonreducing conditions.

These mobilities are consistent with the disulfide-linked homodimeric structure of PSGL-1 (Moore, et al., 1992). Furthermore, the [$^{35}$S]sulfate-labeled protein was immunoprecipitated with a specific rabbit antiserum generated against a synthetic peptide encoding residues 42–56 of the extracellular domain of PSGL-1. Analysis of the sup ematants showed that anti-42–56 precipitated all of the $^{35}$S-PSGL-1, whereas normal rabbit serum (NRS) precipitated none of the $^{35}$S-PSGL-1. These results demonstrate that PSGL-1 is post-translationally sulfated.

Sulfate can be incorporated into eukaryotic glycoproteins as tyrosine sulfate (Huttner, et al. (1988) *Mod. Cell Biol.* 6, 97–140) or as sulfated carbohydrates (Fiete, et al., (1991) *Cell* 65, 1103–1110; Kjellen and Lindahl, (1991) *Ann. Rev. Biochem.* 60, 443–475). In preliminary studies, sulfated carbohydrates were not detected on PSGL-1, using techniques that detected such structures on other glycoproteins (Shilatifard, et al. (1995, 1993)). The cDNA sequence of PSGL-1 predicts four extracytoplasmic tyrosine residues, three of which are clustered at positions 46, 48 and 51 within a predicted consensus sequence for tyrosine sulfation (Huttner and Baeuerle (1988)). To determine if PSGL-1 has tyrosine sulfate, the gel slice containing the 240 kDa $^{35}$S-PSGL-1 was hydrolyzed with strong base and analyzed by anion exchange chromatography. A single radioactive peak was recovered that co-eluted with tyrosine sulfate but not with sulfated sugar standards (FIG. 1A).

Tyrosine sulfate was then tested for importance for binding of PSGL-1 to P-selectin. Although the functions of tyrosine sulfate within proteins are not clear, some proteins require this modification for optimal activity (Pittman, et al. (1992) *Biochemistry* 31, 3315–3325; Dong, et al., (1994) *Biochemistry* 33, 13946–13953). The usual approach for assessing the importance of tyrosine sulfate is to prevent sulfation of newly synthesized proteins with chemical inhibitors or to replace tyrosine with phenylalanine by site-directed mutagenesis. An alternative approach in which sulfate was enzymatically removed from tyrosine on intact PSGL-1 was tested. The ability of an arylsulfatase from Aerobacter aerogenes to release sulfate from $^{35}$S-tyrosine sulfate was also determined. As little as 50 mU of this arylsulfatase quantitatively released [$^{35}$S]sulfate from $^{35}$S-tyrosine sulfate derived from PSGL-1 (FIGS. 1B, 1C). This cleavage was specific, since 1000 mU of the enzyme did not release any sulfate from Gal-6-sulfate, GlcNAc-6-sulfate, GalNAc-4-sulfate, and GalNAc-6-sulfate.

The ability of the arylsulfatase to release sulfate from intact $^{35}$S-PSGL-1 was examined. [$^{35}$S]sulfate released by the enzyme was quantified by precipitation as insoluble $BaSO_4$. Up to 50% of the [$^{35}$S]sulfate on PSGL-1 was released by 500 mU of arylsulfatase; increasing amounts of enzyme did not release more radioactivity (FIG. 2).

The functional importance of the tyrosine sulfate on PSGL-1 was assessed by treating $^{125}$I-PSGL-1 with arylsulfatase and measuring the rebinding of the treated ligand to a P-selectin column. Binding of arylsulfatase-treated $^{125}$I-PSGL-1 to P-selectin was reduced in a dose-dependent manner; the decreased binding was inversely related to the amount of sulfate released from $^{35}$S-PSGL-1 (FIG. 2). The reduced binding of PSGL-1 to P-selectin following arylsulfatase treatment was not due to general release of sialic acid and/or fucose by contaminating exoglycosidases, because PSGL-1 treated with 1000 mU of arylsulfatase bound quantitatively to any affinity column containing CSLEX-1, a monoclonal antibody of sLe$^x$.

Arylsulfatase released approximately 50% of the [$^{35}$S] sulfate from $^{35}$S-PSGL-1 and decreased rebinding of $^{125}$I-PSGL-1 to P-selectin by the same degree. The possibility was considered that the fraction of $^{35}$S-PSGL-1 that rebound to P-selectin following treatment with arylsulfatase retained critical tyrosine sulfate residues, whereas the fraction that did not rebind to P-selectin had lost tyrosine sulfate. $^{35}$S-PSGL-1 was treated with 1000 mU of arylsulfatase and then applied to a P-selectin column. The bound and unbound fractions were analyzed by SDS-PAGE. A band corresponding to $^{35}$S-PSGL-1 was observed in the bound fractions, whereas no band was seen in the unbound fractions. The radioactivity in the unbound fractions represented free sulfate. When the band of $^{35}$S-PSGL-1 in the bound fractions was hydrolyzed, radioactivity was recovered in tyrosine sulfate. In the control experiment, $^{125}$I-PSGL-1 was treated with 1000 mU of arylsulfatase and then applied to the P-selectin column. SDS-PAGE analysis revealed that intact $^{125}$I-PSGL-1 was recovered in both the unbound and bound fractions. Thus, arylsulfatase removed sulfate quantitatively from a subset of PSGL-1, which no longer. bound P-selectin, but the enzyme did not otherwise degrade PSGL-1.

The tyrosine sulfate remaining in the P-selectin-bound-subset of PSGL-1 may be resistant to arylsulfatase because of its inaccessibility or because of some other feature of PSGL-1 that blocks action of the enzyme. When $^{35}$S-PSGL-1 was partly deglycosylated by treatment with peptide:N-glycosidase F and *Arthrobacter ureafaciens* neuraminidase, subsequent treatment with arylsulfatase released up to 70% of the radioactivity as [$^{35}$S]sulfate. Since neuraminidase also eliminates binding of PSGL-1 to P-selectin, it could not be determined whether the increased removal of [$^{35}$S]sulfate further reduced binding of PSGL-1 to P-selectin. These results suggest that the extensive glycosylation of PSGL-1 may account for the inaccessibility of some tyrosine sulfate sites to arylsulfatase.

To further demonstrate the importance of tyrosine sulfation for the function of PSGL-1, the antiserum to the peptide encoding residues 42–56 of the extracellular domain of PSGL-1 was used. As noted above, this region contains the three potential tyrosine sulfation sites at residues 46, 48, and 51. The antiserum inhibited binding of $^{125}$I-PSGL-1 to immobilized P-selectin (FIG. 3A), and also abolished binding of P-selectin to HL-60 cells, as measured by flow cytometry (FIG. 3B). Thus, antiserum to the 42–56 peptide binds to native PSGL-1 and effectively blocks its recognition by P-selectin.

These results demonstrate that PSGL-1 contains tyrosine sulfate that is required for high affinity binding to P-selectin. It has been shown previously that PSGL-1 contains the sLe$^x$ determinant on O-linked oligosaccharides and that both sialic acid and fucose are required for binding of PSGL-1 to P-selectin. Tyrosine sulfate may be important because it promotes appropriate presentation of the glycans that bind directly to P-selectin. Alternatively, tyrosine sulfate may directly interact with P-selectin. This latter possibility seems more likely, since sulfatide and sulfated oligosaccharides are known to bind P-selectin. Sulfate is also a critical determinant for the binding of GlyCAM-1 to L-selectin, but GlyCAM-1 contains sulfate in Gal-6-sulfate and GlcNAc-6-rather than on monosaccharides.

The results suggest a model in which PSGL-1 presents both carbohydrate and tyrosine sulfate as components of a critical recognition site for P-selectin. It is hypothesized that this site is located at the N-terminal, membrane-distal region of PSGL-1, near the three potentially sulfated tyrosine residues. Consistent with this hypothesis, PL1, a monoclonal antibody that recognizes a membrane-distal epitope on PSGL-1, blocks binding of fluid-phase P-selectin to leukocytes and abolished adhesion of neutrophils to P-selectin under both static and shear conditions. In contrast, PL2, a monoclonal antibody that recognizes a membrane-proximal epitope on PSGL-1, does not inhibit binding to P-selectin. The concept that P-selectin recognizes a localized site on a mucin-like glycoprotein is distinct from a model in which a selectin recognizes multiple, clustered O-linked glycans attached along the entire polypeptide (Lasky, et al., (1992) *Cell* 69, 927–938; Baumheuter, et al., (1993) *Science* 262, 436–438).

EXAMPLE 4

Determination of O-glycan Structures on PSGL

The structures of the O-glycans on PSGL-1 synthesized by HL-60 cells metabolically-radiolabeled with $^3$H-sugar precursors were determined. The glycosylation of PSGL-1 was compared with that of CD43 to determine whether two sialomucins expressed by the same cells are O-glycosylated differently. The HL-60 cell line was used in these studies because the post-translational modifications known to be important for binding to P-and E-selectin on both HL-60 and neutrophil PSGL-1 are comparable.

The studies demonstrate that the majority of O-glycans of PSGL-1 are disialylated or neutral forms of the core-2 tetrasaccharide. Only a few of the O-glycans are fucosylated and these contain the structural determinant for the sLe$^x$ antigen. These results demonstrate that PSGL-1 is glycosylated differently from CD43 and that PSGL-1 contains unique O-glycans that are likely to be critical for high affinity interactions with P- and E-selectin.

The abbreviations used are: sLe$^x$, sialyl Lewis x; NDV, Newcastle disease virus; CHO, Chinese hamster ovary; GlcN, glucosamine; GalN, galactosamine; GaINOH, galactosaminitol; GalNAcOH, N-acetylgalactosaminitol; FT, fucosyltransferase; C2GnT, core 2 β1,6 N-acetylglucosaminyltransferase; HPAEC, high pH anion exchange chromatography.

I. Experimental Procedures

Materials—Protein A-Sepharose, QAE-Sephadex, *Arthrobacter ureafaciens* neuraminidase, jack bean β-galactosidase, jack bean β-N-acetylhexosaminidase, and Galβ1→3GalNAc were obtained from Sigma. Pronase and TPCK-treated trypsin were purchased from Worthington Biochemicals. *Escherichia freundii* endo-β-galactosidase was obtained from V-labs. Streptomyces sp.142 α1,3/4-fucosidase was purchased from Takara. Newcastle Disease Virus neuraminidase was obtained from Oxford Glycosystems. D-[6-$^3$H]glucosamine hydrochloride (20–45 Ci/mmol), D-[2-$^3$H]mannose (20–30 Ci/mmol), and L-[6-$^3$H]fucose (70–90 Ci/mmol) were purchased from Dupont/NEN and NaB[$^3$H]$_4$ (40–60 Ci/mmol) was purchased from ARC. Rabbit anti-mouse IgGl was purchased from Zymed. Emphaze™ affinity support resin was obtained from Pierce Biochemicals. Bio-Gel P-4 and P-10 resins and molecular weight markers were obtained from BioRad. All cell culture reagents were obtained from GIBCO/BRL. Other chemicals were ACS grade or better and were obtained from Fisher Scientific.

Isolation of Metabolically-radiolabeled PSGL-1-$^3$H-GlcN, $^3$H-Man, and $^3$H-Fuc metabolic-radiolabeling of HL-60 cells was performed essentially as described by Moore, et al. (1992) *J. Cell. Biol.* 118, 445–456; Wilkins, et al. (1995) *J. Biol. Chem.* 270, 22677–22680. $^3$H-PSGL-1 was purified from cell extracts using affinity chromatography on a column of immobilized, recombinant soluble P-selectin (Ushiyama, et al. (1993) *J. Biol. Chem.* 268, 15229–15237) coupled to Emphaze™ at a density of 5 mg/ml (1.0 ml bed volume) (Moore, et al. (1994) *J. Biol. Chem.* 269, 23318–23327). The enriched EDTA-eluted samples were re-chromatographed on the P-selectin column after dialysis into a Ca$^{2+}$-containing buffer. Purified $^3$H-PSGL-1 was treated with reducing or nonreducing SDS sample buffer [Laemmli, U. K., (1970) *Nature* 227, 680–685] and electrophoresed in a 7.5% polyacrylamide gel. Gels were dried and then autoradiographed by exposure to Fuji RX X-ray film at −80° C. The approximately 250 kDa $^3$H-PSGL-1 in gel slices from nonreducing lanes was analyzed.

Immunoprecipitation of CD43—CD43 was immunoprecipitated from $^3$H-sugar-labeled HC-60 cells using a CD43-specific mAb, H5H5 (IgGl). The H5H5 hybridoma cell line was produced by Dr. T. August and obtained LO from the Developmental hybridoma Bank (The Johns Hopkins University School of Medicine). CD43 was immunoprecipitated by first preloading 50 μl Protein A-Sepharose beads with 100 μg of a rabbit anti-mouse IgGI antibody at 37° C. for 1 h. After washing, the CD43 specific antibody was absorbed to the beads by adding 500 μl of undiluted HSH5 culture media at 37° C. for 1 h. After washing, the preloaded beads were added to the $^3$H-sugar-labeled HC-60 cell extract and incubated at 4° C. overnight. The beads were washed 5× with Hanks balanced salt solution, boiled 5 min in nonreducing SDS sample buffer and analyzed in a 10% SDS-polyacrylamide gel. The purified CD43 of 120 kDa in gel slices identified after autoradiography was excised and analyzed.

β-Elimination of Radiolabeled O-Glycans from $^3$H-PSGL-1 and $^3$H-CD43 and Chromatography of Glycans on Bio-Gel and QAE-Sephadex—The gel slices containing radiolabeled PSGL-1 and CD43 were directly treated with mild base/borohydride as described [Iyer, et al. (1971) Arch. Biochem. Biophys. 142, 101–105; Cummings, et al. (1983) J. Biol. Chem. 258, 15261–15273]. Released radiolabeled glycans were desalted by chromatography on a column of Dowex 50 (H$^+$ form) and the glycans were further analyzed. Chromatography was performed on Bio-Gel P-4 (medium mesh) in a 1×90 cm column and on Bio-Gel P-10 (medium mesh) in a 1×48 cm column in 0.1 M pyridyl/acetate buffer, pH 5.5 and 1 ml fractions were collected. The anionic character and sialylation of glycans was assessed partly by chromatography on column of QAE-Sephadex, with step elution in 2 mM Tris-base containing 20, 70, 140, 200, and 250 mM NaCl.

Preparation of Radiolabeled O-Glycan Standards—The simple core-1 O-glycan Galβ1→3GalNAc was radiolabeled by reduction in the presence of NaB[$^3$H]$_4$ to form Galβ1→3GalNAcOH[$^3$H] [Li, et al. (1978) J. Biol. Chem. 253, 7762–777]. A set of $^3$H-GlcN-labeled standard glycans was prepared from $^3$H-GlcN-labeled HL-60 cell total glycoproteins following previously described procedures [Carlsson, et al. (1986) J. Biol. Chem. 261, 12787–12795]. The standards included the disialylated core-2 hexasaccharide NeuAcβ2→3Galβ1→4GlcNAcβ1→6 (NeuAcα2→3Galβ1→3)GalNAcOH, the neutral core-2 tetrasaccharide Galβ1→4GlcNAcβ1→6(3Galβ1→3) GalNAcOH, and the trisaccharide GlcNAcβ1→6 (Galβ1→3)GalNAcOH. To prepare these standards, the $^3$H-GlcN-labeled cell extracts were dialyzed against 0.01 M NaHCO$_3$, pH 7.5 and treated with 100 μg/ml TPCK-treated trypsin overnight at 37° C. The dried tryptic digest was treated with mild base/borohydride to effect β-elimination and the released O-glycans were size-fractionated on a column of Bio-Gel P4. Pooled fractions corresponding to the peaks of radioactivity were analyzed for charge distribution by QAE-Sephadex column chromatography. The structure of each glycan was then confirmed by sensitivity to Arthrobacter neuraminidase, β-galactosidase and β-N-acetylhexosaminidase, as determined by descending paper chromatography as described below.

The core-2 fucosylated pentasaccharide standard Galβ1→4(Fucα1→3)GlcNAcβ1→6(Galβ1→3)GalNAcOH was prepared by incubating the $^3$H-GlcN-tetrasaccharide Galβ1→4GlcNAcβ1→6(Galβ1→3)GalNacOH with unlabeled GDP-Fuc (100 μM) in the presence of 50 μg of extract from COS7 cells stably transfected with the human FTIV gene. This α1,3FT adds Fuc in a α1,3 linkage to GlcNAc residues in acceptors containing terminal N-acetyllactosamine sequences [Goelz, et al. (1990) Cell 63, 1349–1356; Lowe, et al. (1991) J. Biol. Chem. 266, 21777–21783; Kumar, et al. (1991) J. Biol. Chem. 266, 21777–21783]. The product of the reaction migrated as a pentasaccharide, as expected, and was converted to the corresponding tetrasaccharide by treatment with the Streptomyces α1,3/4-fucosidase.

To define the Man:Fuc ratio and provide standard high mannose-type N-glycans, radiolabeled glycoproteins were prepared from [$^3$H]Man-labeled HL-60 cell extracts. For the preparation of glycopeptides, the cell extracts were precipitated with TCA and treated with Pronase as described by Cummings, et al. (1983) J. Biol. Chem. 258, 15261–15273. From these glycopeptides, high mannose-type N-glycan standards (Man$_9$GlcNAc$_1$, Man$_8$GlcNAc$_1$, Man$_7$GlcNAc$_1$, Man$_6$GlcNAc$_1$, Man$_5$GlcNAc$_1$) were prepared following treatment with endo-β-N-acetylglucosaminidase H [Cummings, R. D. (1993) Glycobiology: A Practical Approach (M. Fukuda and A. Kobata, eds), pp. 243–289, IRL Press at Oxford University Press, Oxford].

Relative Molar Ratios of Radiolabeled Monosaccharides in [$^3$H]GlcN-labeled Glycans—In the $^3$H-GlcN-labeled, disialylated hexasaccharide NeuAcα2→3Galβ1→4GlcNAcβ1→6 (NeuAcα2→3Galβ1→3)GalNAcOH, prepared from HL-60 cells, the NeuAc, GlcNAc and GalNAcOH residues are radiolabeled [Varki, A. (1994) Meth. Enzymol. 230, 16–32]. During equilibrium radiolabeling the relative molar ratios for these residues should be close to unity. To determine the relative molar ratio for GlcNAc and GalNAc residues, this $^3$H-GlcN-hexasaccharide was desialylated to generate a $^3$H-GlcN-tetrasaccharide; this tetrasaccharide was hydrolyzed in strong acid and the released radioactivity was identified by HPAEC as described below. All radioactivity was recovered in $^3$H-GlcN and $^3$H-GalNOH in the ratio of $^3$H-GlcN:$^3$H-GalNOH of 1.0:0.8. This ratio was used as a correction factor for calculating relative molar ratios of isolated glycans, i.e. the radioactivity recovered in $^3$H-GalN (OH) in a sample after hydrolysis was divided by 0.8. The relative molar ratio is consistent with other studies on HL-60 cells metabolically-radiolabeled with the $^3$H-GlcN precursor [Maemura, K. and Fukuda, M. (1992) J. Biol. Chem. 267, 24379–24386]. To determine the relative molar ratio for NeuAc and GlcNAc residues, the $^3$H-GlcN-hexasaccharide was desialylated with neuraminidase and the released radioactivity in NeuAc was determined. The radioactivity recovered in GlcN and NeuAc was in the ratio of 1.0:1.4, respectively. Since NeuAc radioactivity was derived from two residues of the disialylated hexasaccharide, this gave a final value for the relative molar ratio for GlcN:NeuAc of 1.0:0.7.

Determination of Monosaccharide Composition—The ratios of GlcN:GalN and Man:Fuc in PSGL-1 and CD43 were determined following strong acid hydrolysis of excised gel slices containing purified PSGL-1 and CD43. The gel slices were treated with 250 μl 2N trifluoroacetic acid (TFA) at 121° C. for 2 h. The released, radiolabeled monosaccharides in the hydrolysate were identified by a pH anion exchange chromatography (HPAEC) on a CarboPac PA-1 column (4×250 mm) in a Dionex system and elution with 16 mM NaOH for 30 min. Fractions (0.3 min) were collected and radioactivity was determined by scintillation counting. The radiolabeled monosaccharides were identified by their retention times compared to those of standard monosaccharides. The relative molar ratio for GlcN:GalN in glycans was calculated by dividing the radioactivity in the GlcN peak by the radioactivity in the GalN peak and correcting for differences in specific activity of $^3$H-GlcN versus $^3$H-GalN. The Man:Fuc ratio in $^3$H-Man-glycans was also determined following acid hydrolysis as described above, using a Man:Fuc ratio of 1.0:1.0, which is typically observed after equilibrium radiolabelling of cells with [2-$^3$H]Man.

Miscellaneous procedures—Enzymatic treatments of glycans with β-N-acetylhexosaminidase, β-galactosidase, Arthrobacter neuraminidase, Streptomyces α1,3/4-fucosidase and E. freundii endo-β-galactosidase were performed as described by Cummings, et al. (1989) *Methods in Cell Biol.* 32, 142–180; Srivatsan, et al. (1992) *J. Biol. Chem.* 267, 20196–20203.

Digestion with NDV-neuraminidase was performed in 20 µl 10 mM phosphate, pH 7.0 with 20 mU of enzyme for 24 h at 37° C., followed by addition of another 20 mU of enzyme and further incubation for 24 h. O-glycans were analyzed and purified by descending paper chromatography on w Whatman filter paper for the times noted using the pyridine/ethyl acetate/water/acetic acid (5:5:1:3) solvent system, as described by Cummings, R. D. (1993) *Glycobiology:*. Glycans were chemically defucosylated by treatment with 0.1 N TFA at 100° C. for 1 h as described by Spooncer, et al. (1984) *J. Biol. Chem.* 259, 4792–4801.

II. Results

Purification of PSGL-1 and CD43—PSGL-1 and CD43 were purified from HL-60 cells metabolically labeled with $^3$H-GlcN. PSGL-1 from $^3$HGlcN-labeled HL-60 cell extracts was purified by affinity chromatography on immobilized P-selectin, following by re-chromatography of the bound, EDTA-eluted fraction. Virtually all (90–99%) of the radiolabel in the 2×-purified material bound P-selectin. This two-step procedure was necessary to remove a contaminating glycoprotein of approximately 120 kDa under nonreducing conditions that remained after the first step. The purified PSGL-1 behaved as a dimer of approximately 250 kDa in nonreducing conditions and approximately 120 kDa in reducing conditions. The purified PSGL-1 was resolved by SDS-PAGE under reducing or nonreducing conditions in 7.5% polyacrylamide, and then analyzed by autoradiography.

CD43 $^3$H-GlcN-labeled HL-60 cell extracts were immunoprecipitated with a CD43-specific mAb plus a secondary rabbit anti-mouse IgG1 antibody or secondary antibody alone. The immunoprecipitates were electrophoresed under nonreducing conditions in a 10% acrylamide gel and then analyzed by autoradiography. A single band of 120 kDa for CD43. was observed in both reducing and in nonreducing conditions.

Composition of Radiolabeled Sugars in PSGL-1 and CD43—In the initial assessment of the glycosylation of PSGL-1 and CD43, the ratio of GlcN:GalN in the purified glycoproteins was determined. $^3$H-GlcN is metabolized by animal cells into radiolabeled GlcNAc, GalNAc and sialic acids. Gel slices containing the $^3$H-GlcN-glycoproteins were treated with strong acid (which results in destruction of sialic acids) and the radiolabeled GlcN and GalN were identified by Dionex HPAEC. The GlcN:GalN ratio was determined to be approximately 2:1 for PSGL-1 and approximately 1:1 for CD43. The GlcN:GalN ratio of approximately 1:1 for CD43 is consistent with published evidence that a majority of the glycans in CD43 iS have the simple core-2 motif Galβ1→4GlcNAcβ1→6 (Galβ1→3) GalNAcOH. These results demonstrate that the glycans of PSGL-1 contain higher amounts of GlcNAc relative to GalNAc than the glycans of CD43.

The presence of the sLe$^x$ determinant on PSGL-1 has led to expectations that PSGL-1 might be heavily fucosylated. The amount of Fuc present on PSGL-1 and CD43 isolated from HL-60 cells metabolically radiolabeled with [2-$^3$H] Man was assessed. This labeled precursor is metabolized by cells to 2-$^3$H-Fuc and the relative specific activity of Man and Fuc after equilibrium labeling is equivalent. $^3$H-Man-PSGL-1 and -CD43 were isolated by SDS-PAGE and autoradiography. The corresponding bands were subjected to strong acid hydrolysis and the released monosaccharides were separated by HPAEC on a Dionex system. The Man-:Fuc ratio was determined to be 3:5 for PSGL-1 and 3:2 for CD43. As a control, the Man:Fuc ratio was also determined for the total unpurified glycoproteins from HL-60 cells and found to be 3:1. The relative amounts of $^3$H-Man and $^3$H-Fuc in PSGL-1, CD43, and total HL-60 glycoproteins was determined after acid hydrolysis of $^3$H-Man-PSGL-1, $^3$H-Man-CD43, and total $^3$H-Man-labeled HL-60 cell glycoproteins. Acid hydrolysates were analyzed by HPAEC using a Carbo-Pac PA-1 column eluted with 16 mM NaOH. The total radioactivity in each shaded peak was determined. PSGL-1 contains more Fuc residues than CD43 and more Fuc residues than average glycoproteins in HL-60 cells.

Using this information it is possible to estimate the number of Fuc residues on PSGL-1. The cDNA sequence of PSGL-1 predicts that PSGL-1 has three potential N-glycosylation sites. PSGL-1 contains only complex-type N-glycans, each of which should have 3 Man residues. Thus, 3 complex-type N-glycans on PSGL-1 represent 9 Man residues per mol and, correspondingly, there are approximately 15 Fuc residues per mol of PSGL-1. In contrast, CD43 contains only a single N-linked glycan and has much less Fuc in comparison to PSGL-1. Taken together, the compositional analyses from $^3$H-Man-glycoproteins demonstrate that PSGL-1 is glycosylated differently than CD43.

β-Elimination of O-Glycans from PSGL-1 and CD43 and Chromatography on Bio-Gel P-4 and P-10—The O-glycans of PSGL-1 and CD43 were directly released by treating gel slices containing purified glycoproteins with mild base-borohydride to effect β-elimination and were fractionated on a column of Bio-Gel P-4. The released $^3$H-GlcN-glycans from both PSGL-1 and CD43 were recovered in three fractions represented 47%, 41% and 11% of the total radioactivity, respectively. Compared to CD43, PSGL-1 contains a high proportion of relatively large glycans.

The P-4-I samples from both PSGL-1 and CD43 were further purified by chromatography on a column of Bio-Gel P-10. Radioactivity in the P-4-I fraction from PSGL-1 separated into two major peaks on Bio-Gel P-10 designated P-10-1 and P-10-2. This population of glycans is larger in size than the disialylated core-2 hexasaccharide standard NeuAcα2→3 Galβ1→4GlcNAcβ1→6 (NeuAcα2→3Galβ1→3)GalNAcOH. The major material in the P-4-II fraction from PSGL-1 eluted on Bio-Gel P-10 in a position slightly smaller (designated P-10-3) than the disialylated core-2 hexasaccharide standard. In. contrast, most of the material in both the P-4-I and P-4-II fractions of CD43 eluted identically on Bio-Gel P-10 as the disialylated core-2 hexasaccharide standard.

The glycans recovered in P-4-I from CD43 were analyzed using exoglycosidase treatments and anion exchange chromatography. The glycans were shown to be the expected disialylated core-2 hexasaccharide. A small fraction of the P-4-I sample from CD43 was recovered in larger-sized glycans on Bio-Gel P-10, consistent with previous studies showing that a small fraction of O-glycans from CD43 have an extended polylactosamine structure on the core-2 motif. Since the structures of glycans in CD43 have been described, they were not further analyzed.

Compositional Analyses of P-10-1, P-10-2 and P-10-3 Glycans from PSGL-1—O-glycans released from Ser/Thr residues by β-elimination should contain $^3$H-GalNAcOH at the reducing terminus, which is recoverable as $^3$H-GalNOH following strong acid hydrolysis. To identify which glycans in the mixture from PSGL-1 represent the O-glycans, the GalNOH, GalN and GlcN content of each glycan from Bio-Gel P-10 was determined by HPAEC on a Dionex system following strong acid hydrolysis of the $^3$H-GlcN- PSGL-1 P-10-1, P-10-2, and P-10-3 fractions. Acid hydrolysates were analyzed by HPAEC using a Carbo-Pac PA-1 column eluted with 16 mM NaOH. The total radioactivity in each peak was determined. More than 95% of the total GalN(OH) in PSGL-1 P-10-2 and P-10-3 fractions was recovered as GalNOH, demonstrating that β-elimination was efficient and that the O-glycans of PSGL-1 are represented in these fractions. The glycans in P-10-1 lack GalNOH and do not represent O-glycans released by β-elimination. Instead, the P-10-1 fraction contains N-glycans still attached to the peptide. This was confirmed by the presence of $^3$H-Man recovered in these glycans from $^3$H-Man-PSGL-1. The small amount of GalN recovered in P-10-1 samples might arise from GalNAc residues present in N-glycans, or it could result from a small amount of residual O-glycans still linked to peptide and not released during β-elimination procedures.

Sialylation of P-10-1, P-10-2 and P-10-3 Glycans from PSGL-1—The sialylation patterns of the O-glycans in P-10-2 and P-10-3 and of the N-glycans in P-10-1 were determined by an anion-exchange column chromatography on QAE-Sephadex, before and after neuraminidase treatment. In this system, glycans with 1 negative charge (1 sialic acid) elute with 20 mM NaCl, those with 2 negative charges (2 sialic acids) elute with 70 mM NaCl, and those with 3 negative charges (3 sialic acids) elute with 140 mM NaCl [24,25]. $^3$H-GlcN-PSGL-1 P-10-1, P-10-2, and P-10-3 fractions were applied to columns of QAE-Sephadex and the columns were eluted with the indicated concentrations of NaCl (mM) either before or after treatment with Newcastle disease virus (NDV) neuraminidase. The glycans in the P-10-1 fraction were heterogeneously charged, consistent with the occurrence of N-glycans in glycopeptides in this fraction. Following treatment with NDV neuraminidase, the radioactivity eluted with 20 mM NaCl was analyzed by descending paper chromatography for 20 h. Authentic NeuAc migrated 25 cm. The P-10-2 glycans were mono-and disialylated species and the P-10-3 glycans were a mixture of neutral and monosialylated species.

To determine whether the anionic character of the glycans was due to sialic acid and to define the linkage of sialic acid, portions of the $^3$H-GlcN-labeled O-glycans were treated with neuraminidase from Newcastle Disease virus (NDV). This enzyme displays high specificity for α2,3-linked sialic acid residues and will not efficiently cleave sialic acid in other linkages [Paulson, et al. (1982) *J. Biol. Chem.* 257, 12734–12738]. After NDV-neuraminidase treatment, the glycans in P-10-1 were less charged, consistent with a loss of sialic acid. However, the presence of residually charged glycans is indicative of the profile expected for N-glycans in glycopeptides. In contrast, the glycans in P-10-2 and P-10-3 became neutral following NDV-neuraminidase treatment, demonstrating that all sialic acids in these glycans are α2,3-linked. The peak of material eluting with 20 mM NaCl following NDV-neuraminidase treatment was quantitatively recovered as free $^3$H-NeuAc, as shown by its co-elution with standard NeuAc on descending paper chromatography. It was previously established that the sialic acid on PSGL-1 from $^3$H-GlcN-labeled HL-60 cells is Neu5Ac. These results demonstrate that the O-glycans in P-10-2 are mono-and disialylated species and that the O-glycans in P-10-3 are a combination of neutral and sialylated species, with sialic acid in α2,3-linkage to glycans. Furthermore, these results demonstrate that the O-glycans of PSGL1 are not sulfated, since neutral species result following treatment with NDV-neuraminidase.

Descending Paper Chromatography of P-10-2 Glycans from PSGL-1—The glycans in P-10-2 were further purified using preparative descending paper chromatography and two major species were recovered. One peak contained larger-sized glycans that migrated slowly from the origin (designated P-10-2a). A small peak of faster migrating material (approximately 24 cm) was also observed, which represented some residual glycans derived from the P-4-II peak. Upon anion-exchange chromatography on QAE-Sephadex, the P-10-2a material eluted as monosialylated species, whereas the P-10-2b material eluted as disialylated species.

Exoglycosidase Treatments of P-10-2b Glycans—The smaller-sized, disialylated glycans in P-10-2b were desialylated by treatment with NDV-neuraminidase, and released sialic acid was removed by chromatography on QAE-Sephadex. The desialylated glycans were analyzed by descending paper chromatography before and after sequential exoglycosidase treatments (FIGS. 4A–E). Following treatment with neuraminidase, the desialylated P-10-2b glycans fractionated as two species (FIG. 4A). A minor peak (approximately 10%) co-migrated with the fucosylated pentasaccharide standard Galβ1→4(Fucβ1→3)GlcNAcβ1→6 (Galβ1→3)GalNAcOH and was designated P-10-2b$_1$. A major peak (approximately 90%) of material co-migrated with the standard core-2 tetrasaccharide Galβ1→4GlcNAcβ1→6(Galβ1→3)GalNAcOH and was designated P-10-2b$_2$.

The desialylated P-10-2b glycans were treated with β-N-acetylhexosaminidase. This treatment did not alter the migration of either species in the sample, indicating that the glycans lack terminal GlcNAc residues. However, when the desialylated P-10-2b mixture was treated with β-galactosidase, P-10-2b$_1$ glycans were unaffected, whereas P-10-2b$_2$ glycans were degraded and co-migrated with the standard trisaccharide GlcNAcβ1→6(Galβ1→3)GalNAcOH (FIG. 4B). The Galβ1→3GalNAcOH structure is resistant to jack bean β-galactosidase, since the enzyme does not efficiently cleave terminal galactosyl residues in β1,3 linkage [Li, et al. (1975) *J. Biol Chem.* 250, 6786–6791]. This was confimed in control studies, in which no cleavage of the standard disaccharide Galβ1→3GalNAcOH occurred with the concentrations of jack bean β-galactosidase used in these analyses. Since the P-10-2b$_2$ glycans are derived from disialylated species, these results demonstrate that the P-10-2b$_2$ glycans are derived from the core-2 hexasaccharide NeuAcα2→3Galβ1→4GlcNAcβ1→6 (NeuAcα2→3Galβ1→3)GalNAcOH.

When the disialylated $^3$H-GlcN-P-10-2b glycans were treated with the Streptomyces α1,3/4-fucosidase, the P-10-2b$_1$ glycans were lost and all recovered glycans co-migrated with the core-2 tetrasaccharide standard Galβ1→4GlcNAcβ1→6(Galβ1→3)GalNAcOH (FIG. 4C). Combined treatment of the desialylated P-10-2b glycans with Streptomyces α1,3/4-fucosidase, β-N-acetylhexosaminidase and β-galactosidase resulted in complete degradation of both P-10-2b, and P-10-2b$_2$ glycans to free $^3$H-GlcNAc and the $^3$H-disaccharide Galβ1→3GalNAcOH (FIG. 4D). These results demonstrate that the P-10-2b$_1$ glycans have the fucosylated pentasaccharide structure Galβ1→4(Fucα1→3)GlcNAcβ1→6 (Galβ1→3)GalNAcOH. Since the original P-10-2b glycans are disialylated species, the P-10-2b$_1$ glycans contain the sLe$^x$ antigen NeuAcα2→3Galβ1→4(Fucα1→3)GlcNAcβ1→R and have the heptasaccharide structure NeuAcα2→3Galβ1→4(Fucα1→3)GlcNAcβ1→6 (NeuAcα2→3Galβ1→3)GalNAcOH (FIG. 7).

To further confim the presence of fucose in these glycans and to facilitate the identification of Fuc in other glycans, HL-60 cells were metabolically radiolabeled with [$^3$H-Fuc]. The $^3$H-Fuc-labeled O-glycans were recovered by β-elimination as described for the $^3$H-GlcN-glycans, following the same procedures described above. The $^3$H-Fuc recovered in the desialylated P-10-2b fraction co-migrated with the desialylated $^3$H-GlcN-P-10-2b$_1$ glycans (FIG. 4E). Taken together, these results demonstrate that the P-10-2b$_1$ glycans from PSGL-1 are fucosylated and contain the sLe$^x$ structure.

Endo- and Exoglycosidase Treatments of P-10-2a Glycans—Because of their relatively large size, the possibility that the P-10-2a glycans contain polylactosamine [3Galβ1→4GlcNAcβ1-]$_n$ was considered. To assess this possibility, the P-10-2a glycans were desialylated and the sialic acid was removed by QAE-Sephadex chromatography. The resulting neutral glycans were treated with endo-β-galactosidase, an enzyme that cleaves internal β1→4 galactosyl residues within a type 2 polylactosamine [Kobata and Takasaki (1993) *Glycobiology: A Practical Approach* (M. Fukuda and A. Kobata, eds), pp. 165–185, IRL Press at Oxford University Press, Oxford]. The glycans were resistant to this treatment (FIG. 5A). The desialylated P-10-2a glycans were also resistant to combined treatment with β-galactosidase and β-N-acetylhexosaminidase (FIG. 5A). The possibility that the P-10-2a glycans might contain a polylactosamine backbone in which all internal GlcNAc residues are fucosylated was then considered. Such polyfucosylated, polylactosamine structures are resistant to endo-β-galactosidase [Fukuda, et al. (1984) *J. Biol. Chem.* 259, 10925–10935]. Complete defucosylation is necessary before endo-β-galactosidase can digest the chains.

The desialylated P-10-2a glycans were chemically defucosylated and then treated with endo-β-galactosidase. After defucosylation, the enzyme quantitatively digested the P-10-2a glycans to release three major compounds in an approximate equimolar ratio identified as the trisaccharide Galβ1→4GlcNAcβ1→3Gal, the residual core-2 trisaccharide GlcNAcβ1→6(Galβ1→3)GalNAcOH, and the disaccharide GlcNAcβ1→3Gal (FIG. 5B). The generation of such products from the specific action of endo-β-galactosidase is predicted for a glycan with the backbone structure:

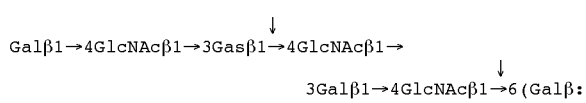

where the arrows indicate specific cleavage sites for endo-β-galactosidase of a defucosylated polylactosamine-containing glycan [Kobata and Takasaki (1993) *Glycobiology*]. The length of the polylactosamine chain can be deduced from the radioactivity recovered in the disaccharide GlcNAcβ1→3Gal relative to the other fragments. The recovery of the trisaccharide GlcNAcβ1→6(Galβ1→3)GalNAcOH following endo-β-galactosidase treatment demonstrates that the polylactosamine is extended from the GlcNAc in β1-6 linkage to the GalNAcOH residue. The recovery of the Galβ1→4GlcNAcβ1→3Gal demonstrates that Gal residues are present in the nonreducing terminus of the polylactosamine. As expected, treatment of the desialylated and defucosylated P-10-2a glycans with a combination of β-galactosidase and β-N-acetylhexosaminidase resulted in complete digestion to free $^3$H-GlcNAc and the $^3$H-disaccharide Galβ1→3GalNAcOH (FIG. 4B).

The resistance of the desialylated P-10-2a glycans to endo-β-galactosidase prior to defucosylation is consistent with the possibility that each GlcNAc residue within the glycan contains an α1,3-linked fucosyl residue in the structure Galβ1→4(Fucα1→3)GlcNAcβ1→3Galβ1→4(Fucβ1→3)GlcNAcβ1→3Galβ1→4(Fucα1→3)GlcNAcβ1→6(Galβ1→3)GalNAcOH. O-glycans containing incompletely fucosylated polylactosamines are sensitive to endo-β-galactosidase.

To confirm the fucosylation pattern predicted for the P-10-2a glycans, the $^3$H-Fuc-P-10-2a glycans were prepared from $^3$H-Fuc-PSGL-1. Following treatment with neuraminidase, the desialylated $^3$H-Fuc-glycans co-migrated with the desialylated $^3$H-GlcN-P-10-2a glycans. When the desialylated $^3$H-Fuc-P-10-2a glycans were treated with the Streptomyces α1,3/4 fucosidase, approximately one-third of the radioactive Fuc was released. This result is predicted based on the postulated glycan structure and on the specificity of the Streptomyces α1,3/4 fucosidase, which can remove Fuc only from penultimate GlcNAc residues within a polyfucosylated glycan [Maemura and Fukuda (1992) *J. Biol. Chem.* 267, 24379–24386, Sano, et al. (1992) *J. Biol. Chem.* 267, 1522–1527]. Taken together, these data demonstrate that the P-10-2a glycans contain three Fuc residues, one of which is in the terminal lactosaminyl unit.

The P-10-2a glycans are monosialylated and could have one of two possible structures (a or b) shown below:

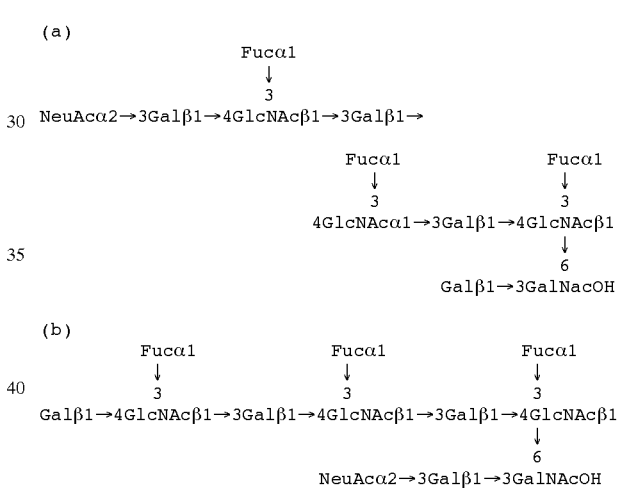

To distinguish between these possibilities, the $^3$H-GlcN-P-10-2a sialylated glycans were treated with a mixture of β-galactosidase, β-N-acetylhexosaminidase, and Streptomyces α1,3/4 fucosidase with or without neuraminidase. It was predicted that structure (a) would require neuraminidase in addition to the other enzymes for complete digestion, whereas structure (b) would be degraded by the exoglycosidases in the absence of neuraminidase. Treatment of the $^3$H-GlcN-P-10-2a with neuraminidase alone, released radiolabeled NeuAc. When the glycans were treated with a mixture of β-galactosidase, β-N-acetylhexosaminidase, and Streptomyces α1,3/4 fucosidase, in the absence of neuraminidase, no radioactivity was released. Inclusion of neuraminidase with other exoglycosidases resulted in complete degradation of the glycans to free $^3$H-NeuAc, free $^3$H-GlcNAc and the $^3$H-disaccharide Galβ1→3GalNAcOH. Taken together, these results demonstrate that the single sialic acid residue on the P-10-2a glycans is present in a terminal position on the polylactosamine chain, shown in structure (a), and that these glycans have the sLe$^x$ structure (FIG. 7).

Endo- and Exoglycosidase Treatments of P-10-3 Glycans—The P-10-3 glycans were primarily neutral or monosialylated species. the predominant species (approximately 80% of the radioactivity) was non-sialylated. The P-10-3 fraction was treated with neuraminidase, and released sialic acid was removed by chromatography on the QAE-Sephadex. Approximately 90% of the desialylated species co-migrated with the standard core-2 tetrasaccharide Galβ1→4GlcNAcβ1→6 (Galβ1→3)GalNAcOH and the remainder co-migrated with the core-1 disaccharide Galβ1→3GalNAcOH (FIG. 6). Treatment of the desialylated P-10-3 glycans with β-galactosidase caused a shift in the migration of the major peak to that of the expected trisaccharide standard (FIG. 6). Treatment with a combination of β-galactosidase and β-N-acetylhexosaminidase generated free $^3$H-GlcNAc and $^3$H-Galβ1→3GalNAcOH (FIG. 6). Approximately 20% of the radiolabel in the P-10-3 glycans was found in predominately monosialylated species that were converted to neutral species by neuraminidase treatment. These results demonstrate that the P-10-3 glycans are primarily neutral core-2 tetrasaccharides and some monosialylated core-2 pentasaccharides (FIG. 7). In addition, some of the neutral glycans have the core-2 disaccharide structure (FIG. 7).

Relative Percentages of O-Glycans In PSGL-1 from HL-60 Cells—The relative percentages of O-Glycans in PSGL-1 can be calculated from the amount of radioactivity recovered in each O-glycan and from the relative molar ratio for $^3$H-GlcN:$^3$H-GalNOH:$^3$H-NeuAc of 1.0:0.8:0.7 (FIG. 7). The majority of O-glycans in PSGL-1 contain the core-2 structure. A minority of the glycans, recovered in P-10-2b, and P-10-2a, contain the sLe$^x$ determinant.

III. Conclusions.

This study demonstrates that PSGL-1 from human HL-60 cells contains O-glycans with a core-2 motif. A majority of the glycans are not fucosylated and are mixtures of neutral and sialylated species. A minority of the O-glycans (approximately 14%) are fucosylated and contain the terminal sLe$^x$ structure. Two types of fucosylated O-glycans are present; one type is a disialylated heptasaccharide lacking polylactosamine and the other is a unique monosialylated, tri-fucosylated glycan containing polylactosamine. The presence of core-2 O-glycans on PSGL-1 from HL-60 cells is consistent with results of studies on the glycosylation of PSGL-1 from human neutrophils. Desialylated PSGL-1 from both human neutrophils and HL-60 cells is resistant to treatment with endo-α-N-acetylgalactosaminidase (O-glycanase), which cleaves only desialylated core-1 glycans. The direct demonstration of sLe$^x$ determinants and polylactosamine on O-glycans of HL-60-derived PSGL-1 reinforces indirect evidence that these structures are present on O-glycans from neutrophil-derived PSGL-1.

Significant differences were observed in the O-glycans on PSGL-1 and CD43 from HL-60 cells. Although both proteins have primarily core-2 O-glycans, PSGL-1 has many neutral core-2 tetrasaccharides, whereas CD43 has mostly disialylated, core-2 hexasaccharides. The core-2 structure is a precursor for polylactosamine synthesis in O-glycans, but only PSGL-1 has significant amounts of polylactosamine. This indicates that the core-2 structure is necessary but not sufficient for polylactosamine addition. Furthermore, CD43 lacks the two species of fucosylated O-glycans found in PSGL-1. Although a monofucosylated O-glycan was identified in CD43, this species represents only 0.5% of the O-glycans in CD43. The tri-fucosylated monosialylated O-glycan identified on PSGL-1 is not found on CD43.

As discussed above, P-selectin can bind weakly to a variety of sulfated glycans and these glycans inhibit binding of P-selectin to human myeloid cells. However, the O-glycans of PSGL-1 are not sulfated. Instead, PSGL-1 contains tyrosine sulfate that is required for interactions with P-selectin but not with E-selectin. Three consensus sites for tyrosine sulfation occur at the amino terminus of PSGL-1 at residues 46, 48 and 51. PL1, a mAb to PSGL-1, blocks binding to P-selectin and recognizes an epitope spanning residues 49–62 that overlaps the tyrosine sulfation sites. Near the tyrosine sulfation sites are two Thr residues that represent potential O-glycosylation sites at residues 44 and 57. Mutations in these residues reduce binding of PSGL-1 to P-selectin when PSGL-1 is co-expressed in COS cells with either FTIII or FTVII. These results suggest that only one or two O-glycans in conjunction with tyrosine sulfate residues may be sufficient to promote high affinity binding of PSGL-1 to P-selectin. However, O-glycans in other regions of the molecule may also contribute to interactions with P- and E-selectin.

It was originally suggested that mucin-like glycoproteins act as convenient scaffolds upon which many O-glycans can be clustered for recognition by selectins. However, this data, in conjunction with other studies, indicate that mucin-like glycoproteins are differentially glycosylated.

Modifications and variations of the present invention, methods for modulating binding reactions involving P-selectin using carbohydrate derived from or forming a portion of the P-selectin ligand, or antibodies to the ligand, will be obvious to those skilled in the art from the foregoing detailed description. Such modifications and variations are intended to come within the scope of the appended claims.

We claim:

1. A purified O-glycan selected from the group consisting of a disialylated, monofucosylated glycan:

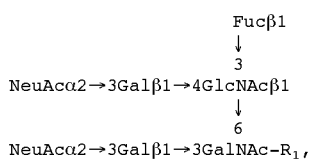

wherein $R_1$ is an H, a sugar or an aglycone, and a monosialylated, trifucosylated glycan having a polylactosamine backbone:

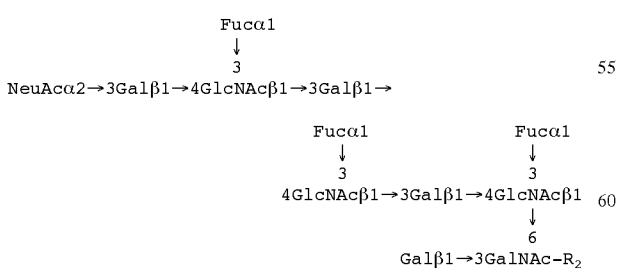

wherein $R_2$=H, OH, a sugar or an aglycone and with the proviso that $R_1$ is not an OH.

2. A composition comprising the O-glycan of claim 1 and a pharmaceutically acceptable carrier.

3. A method for inhibiting inflammation mediated by P-selectin binding comprising administering to an individual in need thereof an effective amount of an O-glycan sufficient to inhibit said inflammation, the O-glycan selected from the group consisting of a disialylated, monofucosylated glycan:

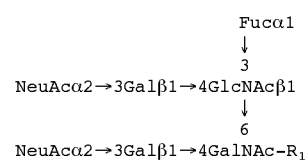

wherein $R_1$ is an H, a sugar or an aglycone, and a monosialylated, trifucosylated glycan having a polylactosamine backbone:

NeuAcα2→3Galβ1→4GlcNAcβ1→3Galβ1→

Fucα1        Fucα1
                ↓           ↓
                3            3
            4GlcNAcβ1→3Galβ1→4GlcNAcβ1
                                ↓
                                6
                         Galβ1→3GalNAc-$R_2$ wherein $R_2$=H, OH, a sugar or an aglycone.

* * * * *

UNITED STATES PATENT AND TRADEMARK OFFICE
CERTIFICATE OF CORRECTION

PATENT NO. : 6,124,267
DATED : September 26, 2000
INVENTOR(S) : Rodger P. McEver, Richard D. Cummings and Kevin L. Moore It is certified that error appears in the above-identified patent and that said Letters Patent is hereby corrected as shown below:

Title page,
Item [73], Assignee, delete "Southpac Trust Internationals, Inc." and substitute
-- The Board of Regents of the University of Oklahoma -- therefor.

Column 51,
Line 42, delete "Fucβ1" and substitute -- Fucα1 -- therefor.

Signed and Sealed this

Twenty-fifth Day of May, 2004

JON W. DUDAS
*Acting Director of the United States Patent and Trademark Office*